US008557812B2

(12) United States Patent
Wang et al.

(10) Patent No.: US 8,557,812 B2
(45) Date of Patent: Oct. 15, 2013

(54) SMALL MOLECULE INHIBITORS OF ANTI-APOPTOTIC BCL-2 FAMILY MEMBERS AND THE USES THEREOF

(75) Inventors: Shaomeng Wang, Saline, MI (US); Guoping Wang, Ann Arbor, MI (US); Guozhi Tang, Ann Arbor, MI (US); Renxiao Wang, Ann Arbor, MI (US); Zaneta Nikolovska-Coleska, Ann Arbor, MI (US); Dajun Yang, Rockville, MD (US); Liang Xu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1960 days.

(21) Appl. No.: 11/209,998

(22) Filed: Aug. 22, 2005

(65) Prior Publication Data

US 2006/0084647 A1    Apr. 20, 2006

Related U.S. Application Data

(60) Provisional application No. 60/603,411, filed on Aug. 20, 2004.

(51) Int. Cl.
*C07D 401/02* (2006.01)
*A61K 31/47* (2006.01)

(52) U.S. Cl.
USPC ............. 514/235.2; 514/252.14; 514/307; 514/308; 514/604; 514/618; 546/139; 546/140; 564/64; 564/162; 564/170; 544/128; 544/295

(58) Field of Classification Search
None
See application file for complete search history.

(56) References Cited

U.S. PATENT DOCUMENTS

| | | | |
|---|---|---|---|
| 2,686,123 | A | 8/1954 | Campbell |
| 4,394,389 | A | 7/1983 | Van't Riet et al. |
| 5,573,759 | A | 11/1996 | Blank |
| 6,114,397 | A | 9/2000 | Flack |
| 6,201,028 | B1 | 3/2001 | Shiff |
| 6,395,720 | B1 | 5/2002 | Kreutz |
| 7,064,124 | B2 * | 6/2006 | Suzuki et al. ............... 514/239.5 |

FOREIGN PATENT DOCUMENTS

| | | |
|---|---|---|
| CA | 2410816 | 10/2002 |
| JP | 60-163812 | 8/1985 |
| WO | WO 02076918 A1 * 10/2002 ............... C07C 65/24 |

OTHER PUBLICATIONS

Whalley et al, Journal of the Chemical Society, 1951, pp. 665-671.*
Karrer et al, Helvetica Chimica Acta, 1919, 2, pp. 466-81.*
Buu-Hoi, Journal of Organic Chemistry (1953), 18, pp. 1723-1729.*
Karrer et al, Helvetica Chimica Acta, 1919, 2, pp. 466-481, (English Translation).*
Wu et al., Toxicology, 236, pp. 1-6, 2007.*
Hisaeda et al, Journal of the Chemical Society, Perkin Transactions 2: Physical Organic Chemistry (1992), (4), 595-604.*
Baine et al., "A Study of the Kolbe-Schmitt Reaction. II. The Carbonation of Phenols," Journal of Organic Chemistry 19:510-514 (1954).
Orndorff, et al., "Thymolsulfonephthalein, The Intermediate Acid, 4'-Hydorxy—3' Isopropyl—6' Methyl—Benzoyl-Benzene-2-Sulfonic Acid and Some of Their Derivatives," Journal of the American Chemical Society 48:981-993 (1926).
Gardner et al., "Trihydroxy-Methyl-Anthraquinones. II," Journal of the American Chemical Society 45:2455-62 (1923).
Adams, Jerry M., et al., "The Bcl-2 Protein Family: Arbiters of Cell Survival," Science, vol. 281, Aug. 28, 1998, pp. 1322-1326.
Cai, Mengli, et al., "An efficient and cost-effective isotope labeling protocol for proteins expressed in *Escherichia coli*," Journal of Biomolecular NMR, 11: pp. 97-102 (1998).
Delaglio, Frank, "NMRPipe: A multidimensional spectral processing system based on UNIX pipes," Journal of Biomolecular NMR, 6 (1995) pp. 277-293.
Garrett, Daniel S., "A Common Sense Approach to Peak Picking in Two-, Three-, and Four-Dimensional Spectra Using Automatic Computer of Contour Diagrams," Journal of Magnetic Resonance, 95, pp. 214-220 (1991).
Grzesiek, Stephan, et al., "The Importance of Not Saturating H20 in Protein NMR. Application to Sensitivity Enhancement and NOE Measurements," J. Am. Chem. Soc. (1993), 115, pp. 12593-12594.
Jansson, Magnus, et al., "High-level production of uniformly 15N- and 13C-enriched fusion proteins in *Escherichia coli*," Journal of Biomolecular NMR, 7 (1996), pp. 131-141.
Lowe, Scott W., et al., "Apoptosis in Cancer," Carciogenesis, vol. 21, No. 3, pp. 485-495 (2000).
Nicholson, Donald W., "From bench to clinic with apoptosis-based therapeutic agents," Nature, vol. 407, Oct. 12, 2000, pp. 810-816.
Ponder, Bruce A.J., "Cancer Genetics," Nature, vol. 411, pp. 336-341, May 17, 2001.
Reed John C., et al., "BCL-2 Family Proteins: Regulators of Cell Death Involved in the Pathogenesis of Cancer and Resistance to Therapy," Journal of Cellular Biochemistry 60 (1996), pp. 23-32.
Reed, John C., "Bcl-2 Family Proteins: Strategies for Overcoming Chemoresistance in Cancer," Advances in Pharmacology, vol. 41, (1997), pp. 501-532.
Sheppard et al., Abstracts of Papers of the Amer. Chem. Soc. 213:81 (1997).
Singapore Patent Application No. 200701168-7 Search Report and Written Opinion, conducted by Australian Office dated Apr. 24, 2008.
EP Search, EP Patent Application No. 05806407.2, dated Jul. 8, 2009.
Amolak Chnd Jain, "Synthesis of Some Naturally Occurring Acetylchromoenes," Bulletin of the Chemical Society of Japan, vol. 52(4), 1203-1204 (1979).

(Continued)

*Primary Examiner* — Zinna Northington Davis
(74) *Attorney, Agent, or Firm* — Casimir Jones SC

(57) ABSTRACT

The invention relates to small molecules which function as inhibitors of anti-apoptotic Bcl-2 family member proteins (e.g., Bcl-2 and Bcl-xL). The invention also relates to the use of these compounds for inducing apoptotic cell death and sensitizing cells to the induction of apoptotic cell death.

7 Claims, 10 Drawing Sheets

(56) References Cited

OTHER PUBLICATIONS

Figure 1:
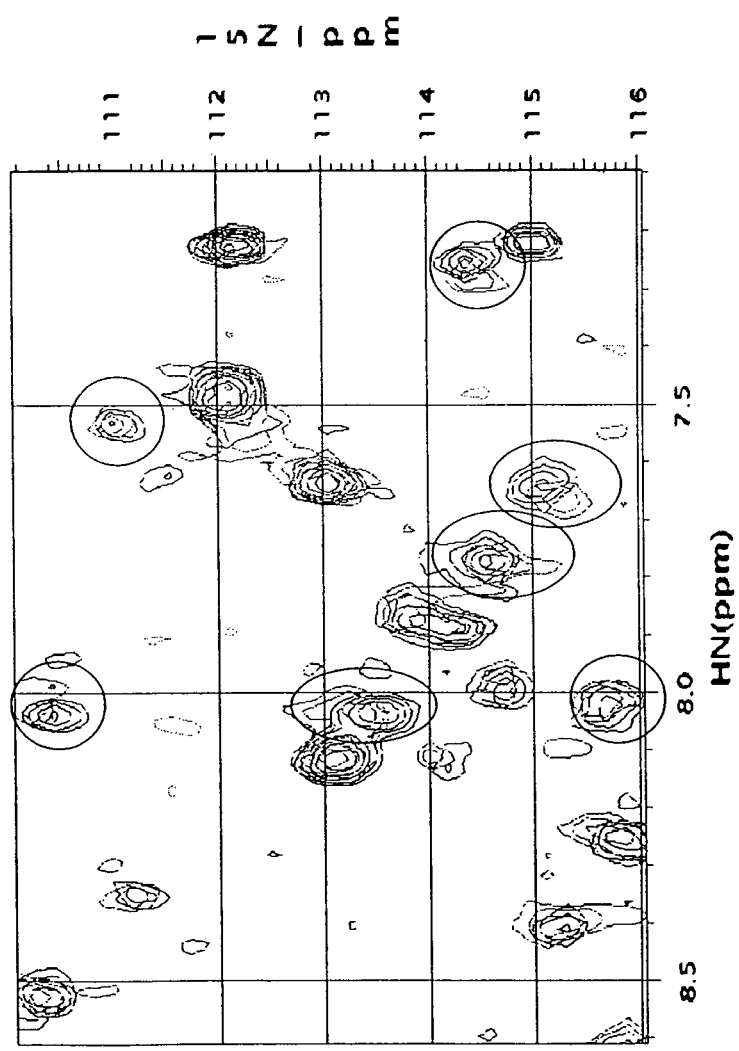

Schill, Gottfried, E. Logemann, "4,6-Di-n-alkylpyrogallol-trimethylatherlll" (English abstract not available), Chemische Berichte, vol. 106, 1973, pp. 2910-2917.

Sutter, M.C., "The pharmacology of isolated veins", British Journal of Pharmacology and Chemotherapy, vol. 24, No. 3 (1965), pp. 742-751.

Korean Patent Application No. 10-2007-7006335 Office Action dated Mar. 19, 2009.

Brevitt and Tan, "Synthesis and in Vitro Evaluation of Two Progressive Series of Bifunctional Polyhydroxybenzamide Catechol-O-methyltransferase Inhibitors," J. Med. Chem. 1997, 40, 2035-2039.

CA Patent Application No. 2,577,752 Office Action dated Sep. 22, 2009, 4 pages.

* cited by examiner

SMALL MOLECULE INHIBITORS OF ANTI-APOPTOTIC BCL-2 FAMILY MEMBERS AND THE USES THEREOF

This application claims priority to U.S. Provisional Application Ser. No. 60/603,411, filed Aug. 20, 2004, herein incorporated by reference in its entirety.

BACKGROUND OF THE INVENTION

1. Field of the Invention

This invention is in the field of medicinal chemistry. In particular, the invention relates to small molecules which function as inhibitors of anti-apoptotic Bcl-2 family member proteins (e.g., Bcl-2 and Bcl-xL). The invention also relates to the use of these compounds for inducing apoptotic cell death and sensitizing cells to the induction of apoptotic cell death.

Field of the Invention

This invention is in the field of medicinal chemistry. In particular, the invention relates to small molecules which function as inhibitors of anti-apoptotic Bcl-2 family member proteins (e.g., Bcl-2 and Bcl-xL). The invention also relates to the use of these compounds for inducing apoptotic cell death and sensitizing cells to the induction of apoptotic cell death.

2. Related Art

The aggressive cancer cell phenotype is the result of a variety of genetic and epigenetic alterations leading to deregulation of intracellular signaling pathways (Ponder, Nature 411:336 (2001)). The commonality for all cancer cells, however, is their failure to execute an apoptotic program, and lack of appropriate apoptosis due to defects in the normal apoptosis machinery is a hallmark of cancer (Lowe et al., Carcinogenesis 21:485 (2000)). Most of the current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., Carcinogenesis 21:485 (2000); Nicholson, Nature 407: 810 (2000)). Accordingly, current and future efforts towards designing and developing new molecular target-specific anti-cancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class of negative regulators of apoptosis is the inhibitor of apoptosis proteins (IAPs) (Deveraux et al., Genes Dev. 13:239 (1999); Salvesen et al., Nat. Rev. Mol. Cell. Biol. 3:401 (2002)). IAP proteins potently suppress apoptosis induced by a large variety of apoptotic stimuli, including chemotherapeutic agents, radiation, and immunotherapy in cancer cells.

The second class of central negative regulators is the Bcl-2 family of proteins, as exemplified by two potent anti-apoptotic molecules, Bcl-2 and Bcl-xL proteins (Adams et al., Science 281:1322 (1998); Reed, Adv. Pharmacol. 41:501 (1997); Reed et al., J. Cell. Biochem. 60:23 (1996)). The Bcl-2 family of proteins now includes both anti-apoptotic molecules such as Bcl-2 and Bcl-xL and pro-apoptotic molecules such as Bax, Bak, Bid, and Bad. Therapeutic strategies for targeting the anti-apoptotic Bcl-2 family members, such as Bcl-2 and Bcl-xL, in cancer to restore cancer cell sensitivity and overcome resistance of cancer cells to apoptosis have been extensively reviewed (Adams et al., Science 281:1322 (1998); Reed, Adv. Pharmacol. 41:501 (1997); Reed et al., J. Cell. Biochem. 60:23 (1996)). Currently, Bcl-2 antisense therapy is in several Phase III clinical trials for the treatment of solid and non-solid tumors. Several laboratories are interested in designing small molecule inhibitors of Bcl-2 and Bcl-xL.

SUMMARY OF THE INVENTION

It is generally accepted that the inability of cancer cells or their supporting cells to undergo apoptosis in response to genetic lesions or exposure to inducers of apoptosis (such as anticancer agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is increased expression and accumulation of IAPs.

The present invention contemplates that exposure of animals suffering from cancer to therapeutically effective amounts of drug(s) (e.g., small molecules) that inhibit the function(s) of anti-apoptotic Bcl-2 family members will kill cancer cells or supporting cells outright (those cells whose continued survival is dependent on the overactivity of anti-apoptotic Bcl-2 family members) and/or render such cells as a population more susceptible to the cell death-inducing activity of cancer therapeutic drugs or radiation therapies. The present invention contemplates that inhibitors of anti-apoptotic Bcl-2 family members satisfy an unmet need for the treatment of multiple cancer types, either when administered as monotherapy to induce apoptosis in cancer cells dependent on anti-apoptotic Bcl-2 family member function, or when administered in a temporal relationship with other cell death-inducing cancer therapeutic drugs or radiation therapies so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent or radiation produces a greater tumor response and clinical benefit in such animals compared to those treated with the compound or anticancer drugs/radiation alone. Put another way, because the compounds lower the apoptotic threshold of all cells that express anti-apoptotic Bcl-2 family members, the proportion of cells that successfully execute the apoptosis program in response to the apoptosis inducing activity of anticancer drugs/radiation is increased. Alternatively, the compounds of the present invention can be used to allow administration of a lower, and therefore less toxic and more tolerable, dose of an anticancer agent and/or radiation to produce the same tumor response/clinical benefit as the conventional dose of the anticancer agent/radiation alone. Since the doses for all approved anticancer drugs and radiation treatments are known, the present invention contemplates the various combinations of them with the present compounds. Also, since the compounds of the present invention may act at least in part by inhibiting anti-apoptotic Bcl-2 family members, the exposure of cancer cells and supporting cells to therapeutically effective amounts of the compounds should be temporally linked to coincide with the attempts of cells to execute the apoptosis program in response to the anticancer agent or radiation therapy. Thus, in some embodiments, administering the compositions of the present invention in connection with certain temporal relationships, provides especially efficacious therapeutic practices.

The present invention relates to compounds that are useful for inhibiting the activity of anti-apoptotic Bcl-2 family members and increasing the sensitivity of cells to inducers of apoptosis. In one particular embodiment, the compounds have formula I:

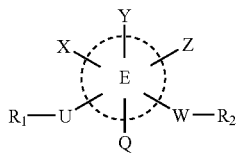

I or a pharmaceutically acceptable salt or prodrug thereof, wherein:
E is phenyl or a heteroaromatic group;
X, Y, and Z are independently H, OH, carboxylic acid, amide, sulfonic acid, sulfonamide, sulfinic acid, sulfinamide, aldehyde, phosphoric acid, phosphonamide, alkyl, alkoxy, or aryl, or one of X and Y or Y and Z form a heterocyclic ring, and at least one of X, Y, and Z is OH, carboxylic acid, amide, sulfonic acid, sulfonamide, sulfinic acid, sulfinamide, aldehyde, phosphoric acid, or phosphonamide;
U and W are independently CO, SO, $SO_2$, $(CH_2)_n$, S, NH, NHCO, P, PO, or $PO_2$;
n is 0 or 1;
Q is H, alkyl, alkenyl, alkynyl, or halogen; or
Q forms a ring with U and/or W;
$R_1$ and $R_2$ are independently hydrogen, alkyl, alkenyl, alkynyl, cycloalkyl, aryl, heteroaryl, partially saturated heterocycle, heterocycle; $NR_3R_4$, $OR_3$, $SR_3$, or $CR_3R_4R_5$, anyone of which may be optionally substituted; and
$R_3$-$R_5$ are independently alkyl, alkenyl, alkynyl, cycloalkyl, aryl, aralkyl, heteroaryl, heteroaralkyl, heterocycle or form a ring, anyone of which may be optionally substituted.

In one embodiment, at least one of X, Y, and Z is OH.

The invention relates to compounds represented by Formula I, which are inhibitors of anti-apoptotic Bcl-2 family members. The invention relates to the use if the compounds of the invention to induce apoptosis in cells. The invention also relates to the use of the compounds of the invention for sensitizing cells to inducers of apoptosis. The compounds are useful for the treatment, amelioration, or prevention of disorders responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those which are chemoresistant, radiation resistant, hormone resistant, and the like). In other embodiments, the compounds can be used to treat hyperproliferative diseases characterized by overexpression of anti-apoptotic Bcl-2 family members.

The present invention provides pharmaceutical compositions comprising a compound of Formula I in a therapeutically effective amount to induce apoptosis in cells or to sensitize cells to inducers of apoptosis.

The invention further provides kits comprising a compound of Formula I and instructions for administering the compound to an animal. The kits may optionally contain other therapeutic agents, e.g., anticancer agents, apoptosis modulating agents.

The invention also provides methods of making compounds of Formula I.

BRIEF DESCRIPTION OF THE DRAWINGS/FIGURES

Figure 2:
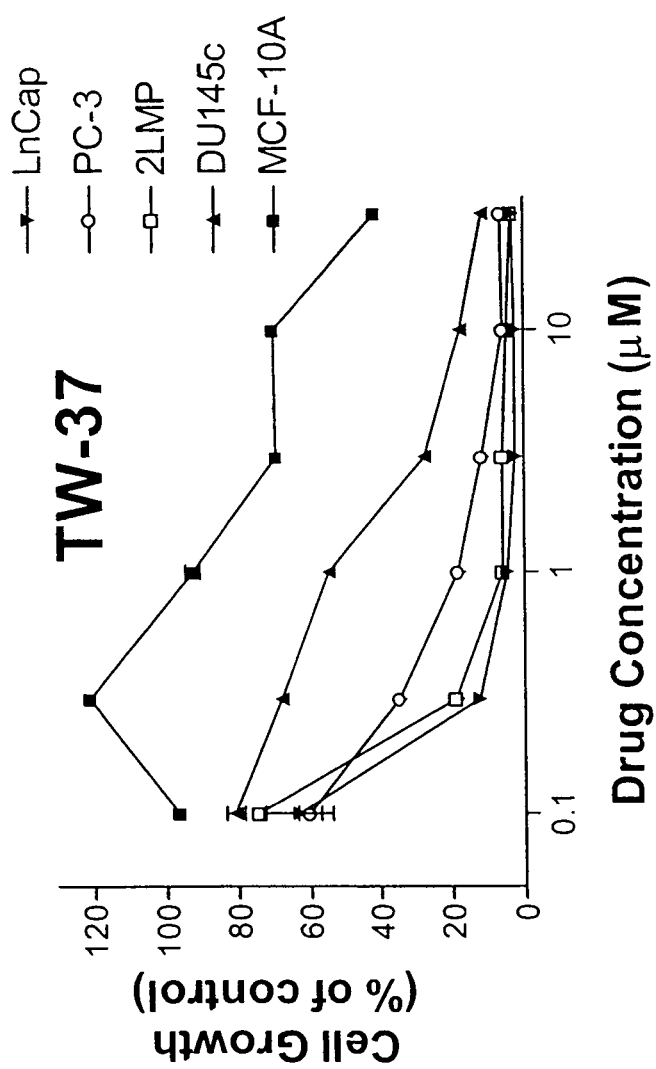
Figure 3:
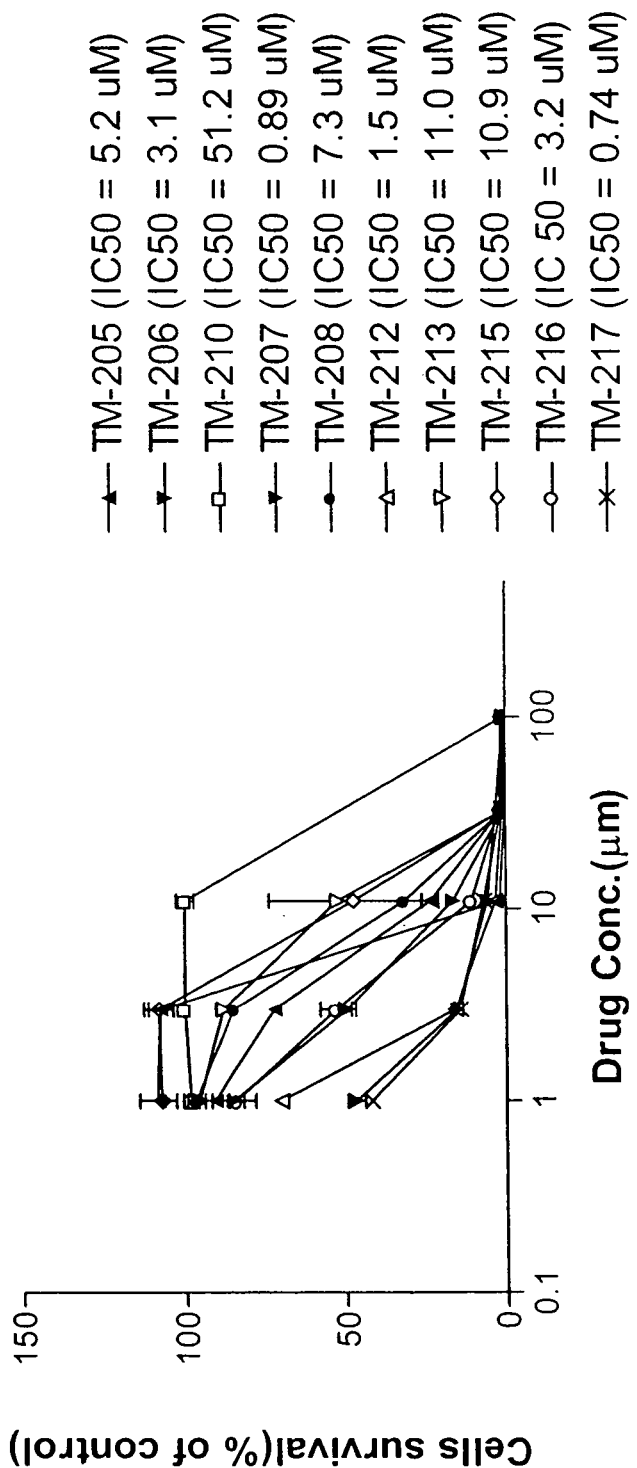
Figure 4:
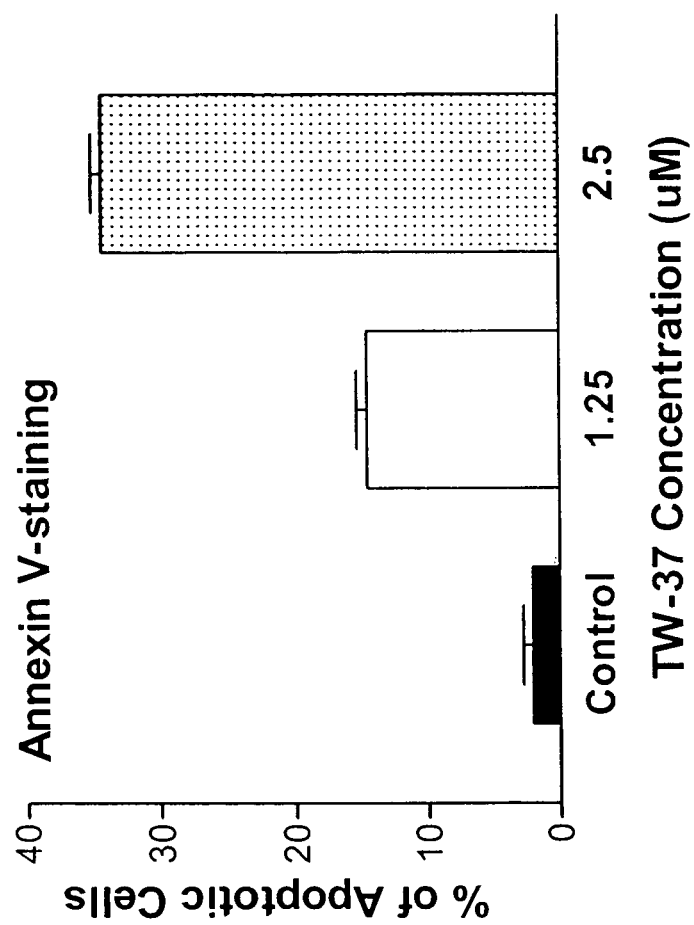
Figure 5:
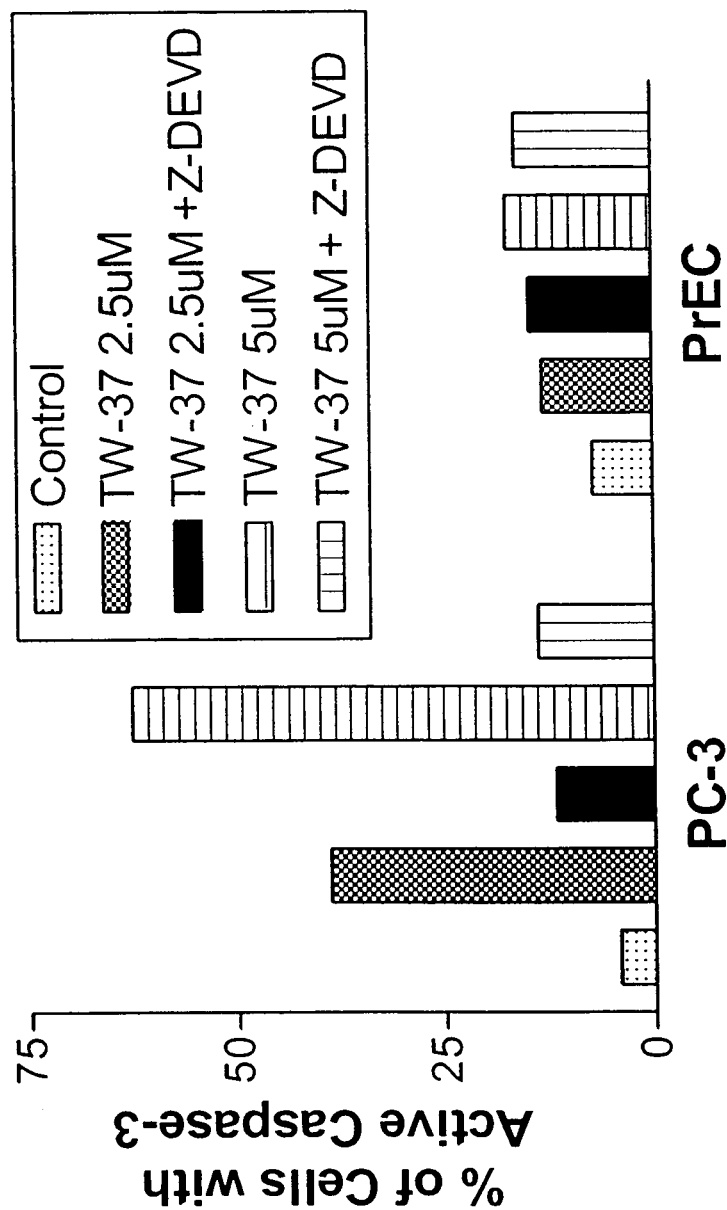
Figure 6:
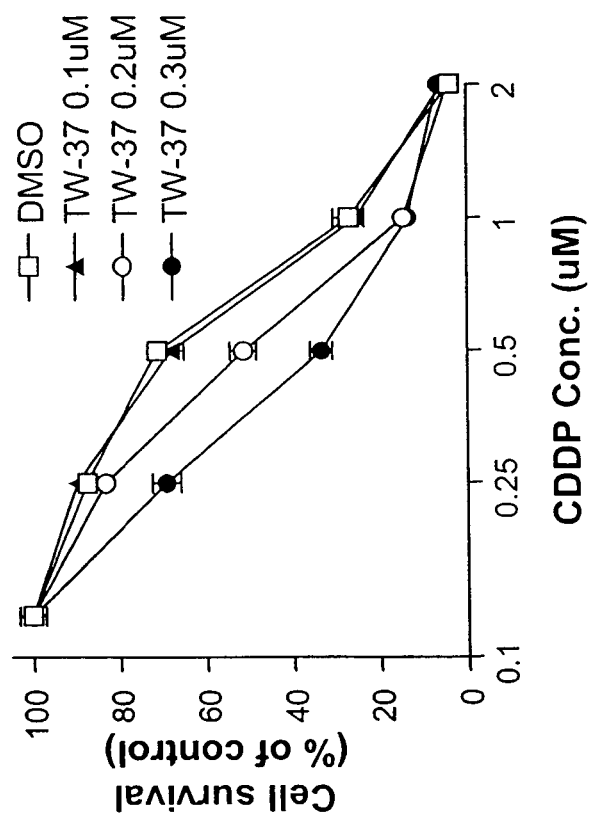
Figure 7:
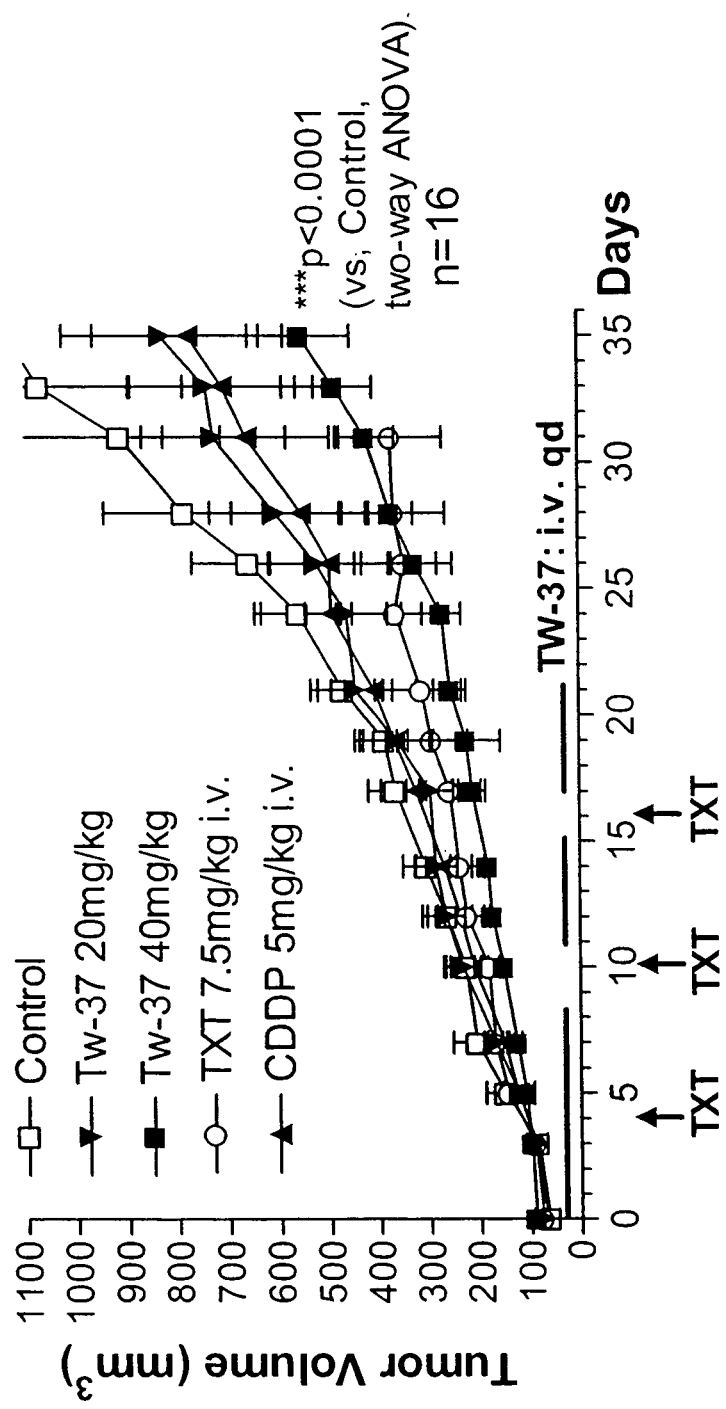
Figure 8:
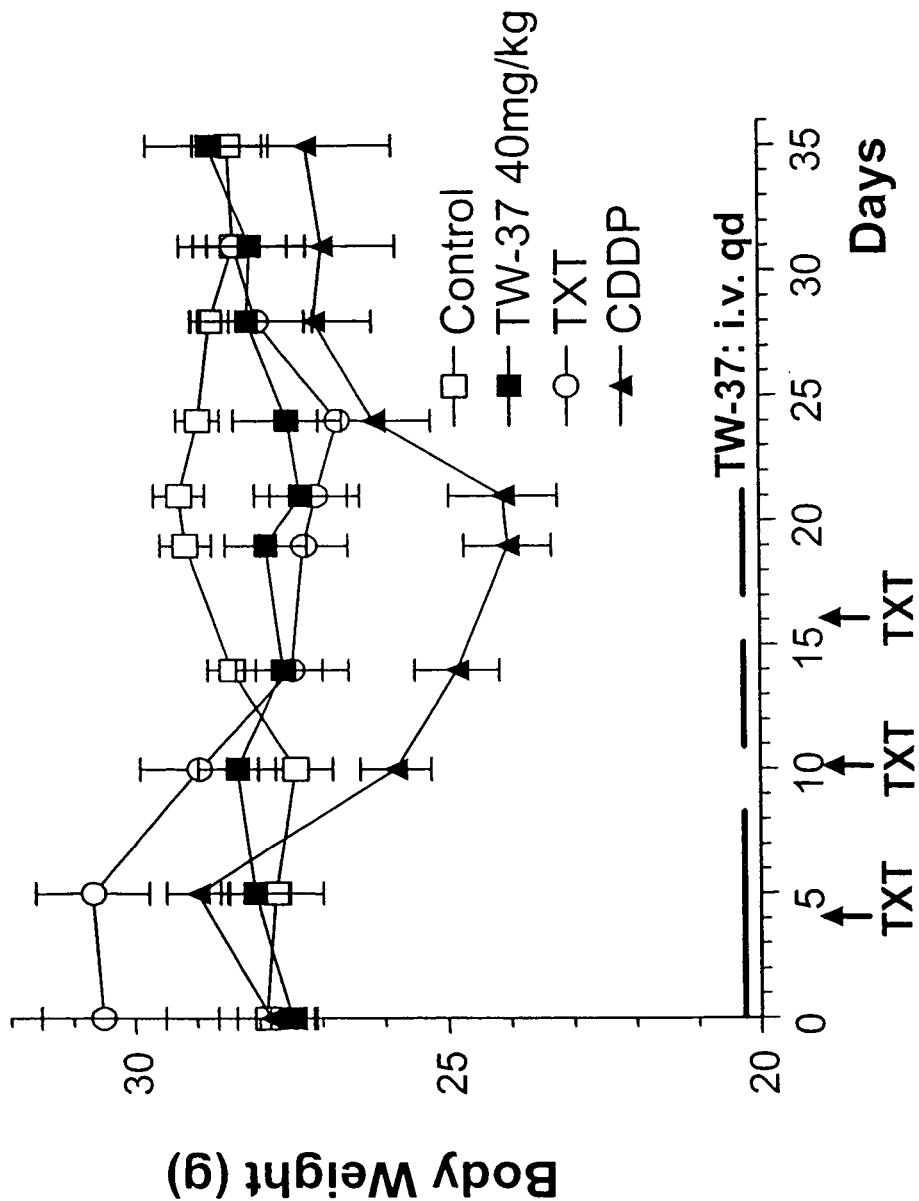
Figure 9:
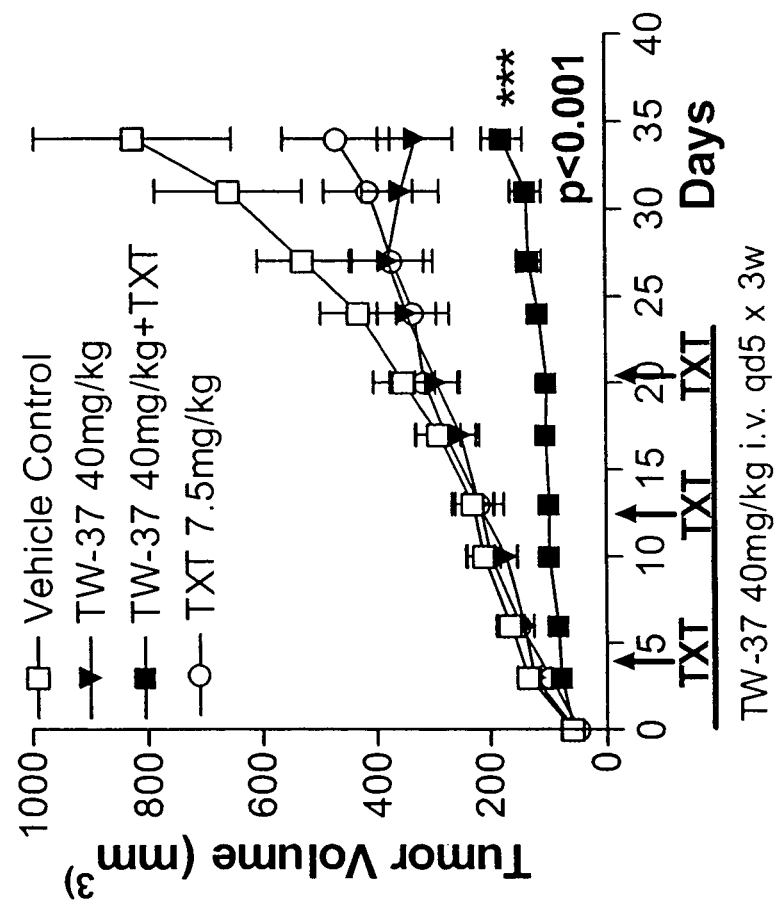
Figure 10:
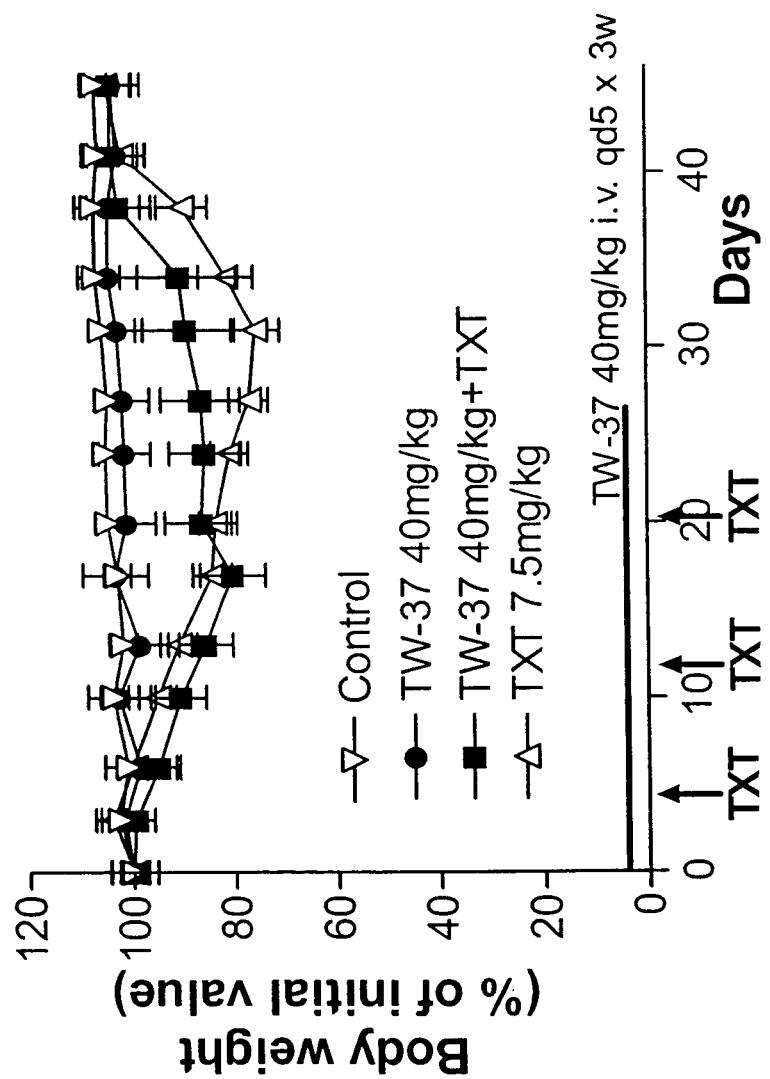

FIG. 1 shows the binding of TW-37 to Bcl-2 by NMR analysis.
FIG. 2 shows the inhibition of cell growth in cancer cells in response to TW-37.
FIG. 3 shows the inhibition of cell growth in cancer cells in response to several compounds.
FIG. 4 shows the induction of apoptosis in PC-3 cells in response to TW-37.
FIG. 5 shows the activation of caspase-3 in PC-3 and PrEC cells in response to TW-37.
FIG. 6 shows the enhancement of cisplatin cytotoxicity by TW-37 in MDA-231 cells.
FIG. 7 shows the inhibition of tumor growth in mice in response to TW-37.
FIG. 8 shows the effect of TW-37, TAXOTERE, and cisplatin on body weight in mice.
FIG. 9 shows the inhibition of tumor growth in mice in response to TW-37 and TAXOTERE alone and in combination.
FIG. 10 shows the effect of TW-37 and TAXOTERE alone and in combination on body weight in mice.

DETAILED DESCRIPTION OF THE INVENTION

The present invention relates to compounds represented by Formula I, which function as inhibitors of anti-apoptotic Bcl-2 family members. By inhibiting anti-apoptotic Bcl-2 family members, these compounds sensitize cells to inducers of apoptosis and, in some instances, themselves induce apoptosis. Therefore, the invention relates to methods of sensitizing cells to inducers of apoptosis and to methods of inducing apoptosis in cells, comprising contacting the cells with a compound of Formula I alone or in combination with an inducer of apoptosis. The invention further relates to methods of treating, ameliorating, or preventing disorders in an animal that are responsive to induction of apoptosis comprising administering to the animal a compound of Formula I and an inducer of apoptosis. Such disorders include those characterized by a dysregulation of apoptosis and those characterized by overexpression of anti-apoptotic Bcl-2 family members.

The term "anti-apoptotic Bcl-2 family members," as used herein, refers to any known member of the Bcl-2 family of proteins which has anti-apoptotic activity, including, but not limited to, Bcl-2, Bcl-xL, Mcl-1, Al/BFL-1, BOO-DIVA, Bcl-w, Bcl-6, Bcl-8 and Bcl-y.

The term "overexpression of anti-apoptotic Bcl-2 family members," as used herein, refers to an elevated level (e.g., aberrant level) of mRNAs encoding for an anti-apoptotic Bcl-2 family member protein(s), and/or to elevated levels of anti-apoptotic Bcl-2 family member protein(s) in cells as compared to similar corresponding non-pathological cells expressing basal levels of mRNAs encoding anti-apoptotic Bcl-2 family member proteins or having basal levels of anti-apoptotic Bcl-2 family member proteins. Methods for detecting the levels of mRNAs encoding anti-apoptotic Bcl-2 family member proteins or levels of anti-apoptotic Bcl-2 family member proteins in a cell include, but are not limited to, Western blotting using anti-apoptotic Bcl-2 family member protein antibodies, immunohistochemical methods, and methods of nucleic acid amplification or direct RNA detection. As important as the absolute level of anti-apoptotic Bcl-2 family member proteins in cells is to determining that they overexpress anti-apoptotic Bcl-2 family member proteins, so also is the relative level of anti-apoptotic Bcl-2 family member proteins to other pro-apoptotic signaling molecules (e.g., pro-apoptotic Bcl-2 family proteins) within such cells. When the balance of these two are such that, were it not for the levels of the anti-apoptotic Bcl-2 family member proteins, the pro-apoptotic signaling molecules would be sufficient to cause the cells to execute the apoptosis program and die, said cells would be dependent on the anti-apoptotic Bcl-2 family member proteins for their survival. In such cells, exposure to an inhibiting effective amount of an anti-apoptotic Bcl-2 family member protein inhibitor will be sufficient to cause the cells to execute the apoptosis program and die. Thus, the term "overexpression of an anti-apoptotic Bcl-2 family member protein" also refers to cells that, due to the relative levels of pro-apoptotic signals and anti-apoptotic signals, undergo apoptosis in response to inhibiting effective amounts of compounds that inhibit the function of anti-apoptotic Bcl-2 family member proteins.

The terms "anticancer agent" and "anticancer drug," as used herein, refer to any therapeutic agents (e.g., chemotherapeutic compounds and/or molecular therapeutic compounds), radiation therapies, or surgical interventions, used in the treatment of hyperproliferative diseases such as cancer (e.g., in mammals).

The term "prodrug," as used herein, refers to a pharmacologically inactive derivative of a parent "drug" molecule that requires biotransformation (e.g., either spontaneous or enzymatic) within the target physiological system to release, or to convert (e.g., enzymatically, mechanically, electromagnetically) the prodrug into the active drug. Prodrugs are designed to overcome problems associated with stability, toxicity, lack of specificity, or limited bioavailability. Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a compound of Formula I), an animal or a cell within an animal more susceptible, or more responsive, to the biological effects (e.g., promotion or retardation of an aspect of cellular function including, but not limited to, cell growth, proliferation, invasion, angiogenesis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, including for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type I diabetes, ulcerative colitis, vitiligo, and the like.

The term "neoplastic disease," as used herein, refers to any abnormal growth of cells being either benign (non-cancerous) or malignant (cancerous).

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "apoptosis modulating agents," as used herein, refers to agents which are involved in modulating (e.g., inhibiting, decreasing, increasing, promoting) apoptosis. Examples of apoptosis modulating agents include proteins which comprise a death domain such as, but not limited to, Fas/CD95, TRAMP, TNF RI, DR1, DR2, DR3, DR4, DR5, DR6, FADD, and RIP. Other examples of apoptotic modulating agents include, but are not limited to, TNFα, Fas ligand, antibodies to Fas/CD95 and other TNF family receptors, TRAIL, antibodies to TRAILR1 or TRAILR2, Bcl-2, p53, BAX, BAD, Akt, CAD, PI3 kinase, PP1, and caspase proteins. Modulating agents broadly include agonists and antagonists of TNF family receptors and TNF family ligands. Apoptosis modulating agents may be soluble or membrane bound (e.g. ligand or receptor). Preferred apoptosis modulating agents are inducers of apoptosis, such as TNF or a TNF-related ligand, particularly a TRAMP ligand, a Fas/CD95 ligand, a TNFR-1 ligand, or TRAIL The inhibitors of anti-apoptotic Bcl-2 family members of the present invention are compounds having the general Formula I:

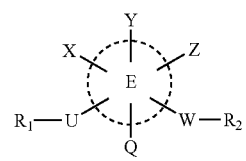

or a pharmaceutically acceptable salt or prodrug thereof, wherein:

E is phenyl or a heteroaromatic group;

X, Y, and Z are independently H, OH, carboxylic acid, amide, sulfonic acid, sulfonamide, sulfinic acid, sulfinamide, aldehyde, phosphoric acid, phosphonamide, alkyl, alkoxy, or aryl, or one of X and Y or Y and Z form a heterocyclic ring, and at least one of X, Y, and Z is OH, carboxylic acid, amide, sulfonic acid, sulfonamide, sulfinic acid, sulfinamide, aldehyde, phosphoric acid, or phosphonamide;

U and W are independently CO, SO, $SO_2$, $(CH_2)_n$, S, NH, NHCO, P, PO, or $PO_2$;

n is 0 or 1;

Q is H, alkyl, alkenyl, alkynyl, or halogen; or

Q forms a ring with U and/or W;

$R_1$ and $R_2$ are independently hydrogen, alkyl, alkenyl, alkynyl, cycloalkyl, aryl, heteroaryl, partially saturated heterocycle, heterocycle; $NR_3R_4$, $OR_3$, $SR_3$, or $CR_3R_4R_5$, anyone of which may be optionally substituted; and $R_3$-$R_5$ are independently alkyl, alkenyl, alkynyl, cycloalkyl, aryl, aralkyl, heteroaryl, heteroaralkyl, heterocycle or form a ring, anyone of which may be optionally substituted.

In one embodiment, at least one of X, Y, and Z is OH.

Useful alkyl groups include straight-chained or branched $C_{1-8}$ alkyl groups, especially methyl, ethyl, propyl, isopropyl, t-butyl, sec-butyl, 3-pentyl, adamantyl, norbornyl, and 3-hexyl groups.

Useful alkenyl groups include straight-chained or branched $C_{2-18}$ alkyl groups, especially ethenyl, propenyl, isopropenyl, butenyl, isobutenyl, and hexenyl.

Useful alkynyl groups are $C_{2-18}$ alkynyl groups, especially ethynyl, propynyl, butynyl, and 2-butynyl groups Useful cycloalkyl groups are $C_{3-8}$ cycloalkyl. Typical cycloalkyl groups include cyclopropyl, cyclobutyl, cyclopentyl, cyclohexyl and cycloheptyl.

Useful aryl groups include $C_{6-14}$ aryl, especially phenyl, naphthyl, phenanthrenyl, anthracenyl, indenyl, azulenyl, biphenyl, biphenylenyl, and fluorenyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Optional substituents include one or more alkyl; halo; haloalkyl; cycloalkyl; aryl optionally substituted with one or more lower alkyl, lower alkoxy, methylenedioxy, halo, haloalkyl, aminosulfonyl, aryl, or heteroaryl groups; aryloxy optionally substituted with one or more lower alkyl, lower alkoxy, methylenedioxy, halo, haloalkyl, aminosulfonyl, aryl, or heteroaryl groups; aralkyl; heteroaryl optionally substituted with one or more lower alkyl, lower alkoxy, methylenedioxy, halo, haloalkyl, aminosulfonyl, aryl, or heteroaryl groups; heteroaryloxy optionally substituted with one or more lower alkyl, lower alkoxy, methylenedioxy, halo, haloalkyl, aminosulfonyl, aryl, or heteroaryl groups; alkoxy; alkylthio; arylthio; amido; amino; aminosulfonyl; sulfonamide; arylsulfonyl optionally substituted with one or more lower alkyl, lower alkoxy, methylenedioxy, halo, haloalkyl, aminosulfonyl, aryl, or heteroaryl groups; acyloxy; arylacyloxy optionally substituted with one or more lower alkyl, lower alkoxy, methylenedioxy, halo, haloalkyl, aminosulfonyl, aryl, or heteroaryl groups; diphenylphosphinyloxy optionally substituted with one or more lower alkyl, lower alkoxy, methylenedioxy, halo, haloalkyl, aminosulfonyl, aryl, or heteroaryl groups; heterocyclo optionally substituted with one or more lower alkyl, lower alkoxy, methylenedioxy, halo, haloalkyl, aminosulfonyl, aryl, heteroaryl, amino acid substituted sulfonyl, or amino acid derivative substituted sulfonyl groups and lower alkyl and aralkyl esters thereof; heterocycloalkoxy optionally substituted with one or more lower alkyl, lower alkoxy, methylenedioxy, halo, haloalkyl, aminosulfonyl, aryl, or heteroaryl groups; partially unsaturated heterocycloalkyl optionally substituted with one or more lower alkyl, lower alkoxy, methylenedioxy, halo, haloalkyl, aminosulfonyl, aryl, or heteroaryl groups; or partially unsaturated heterocycloalkyloxy optionally substituted with one or more lower alkyl, lower alkoxy, methylenedioxy, halo, haloalkyl, aminosulfonyl, aryl, or heteroaryl groups.

Useful amino acid residues include those derived from D and L alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, and histidine. Amino acid derivatives include the amide derivatives.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful alkylaryl and alkylheteroaryl groups include any of the above-mentioned $C_{1-18}$ alkyl groups substituted by any of the above-mentioned $C_{6-14}$ aryl groups or heteroaryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above. Also included are the sulfoxides and sulfones of such alkylthio groups.

Useful amido groups include carbonylamido (i.e., carbonyl bonded to an amino group) as well as any optionally substituted $C_{1-6}$ acyl (alkanoyl) attached to an amino nitrogen, e.g., acetamido, haloacetamido such as trifluoroacetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g., formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g., 2,6-dichlorobenzoyloxy, 2,6-difluorobenzoyloxy and 2,6-di-(trifluoromethyl)-benzoyloxy groups.

Useful amino groups include —NH$_2$, —NHR$_{11}$, and —NR$_{11}$R$_{12}$, wherein R$_{11}$ and R$_{12}$ are alkyl, aminoalkyl, optionally substituted aryl, optionally substituted arylalkyl, or cycloalkyl groups as defined above or where R$_{11}$ and R$_{12}$ form a $C_5$-$C_6$ heterocyclic ring such as piperidinyl, pyrrolidinyl, pyrazinyl, or morpholino optionally substituted by a heteroaryl or an acyl group on the nitrogen.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl, tetramoyl, or tetrahydroisoquinolinyl groups.

Certain of the compounds of the present invention may exist as stereoisomers including optical isomers. The invention includes all stereoisomers and both the racemic mixtures of such stereoisomers as well as the individual enantiomers that may be separated according to methods that are well known to those of skill in the art.

In one embodiment, the compounds of the present invention have the have formula II, wherein the variables are as defined above and at least one of X, Y, and Z is OH.

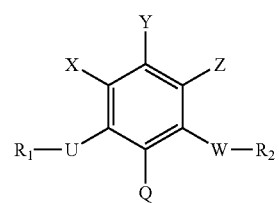

II

Another embodiment of the invention is compounds having formula III, wherein the variables are as defined above and at least one of X, Y, and Z is OH.

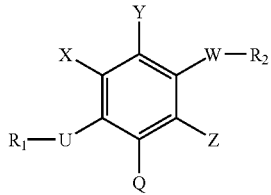
III

In one embodiment, the compounds of the present invention are of formula IV, wherein the variables are as defined above and at least one of X, Y, and Z is OH.

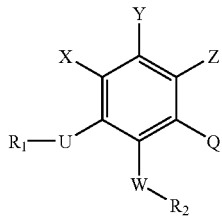
IV

In one embodiment, the compounds of the present invention are of formula V, wherein the variables are as defined above and at least one of X, Y, and Z is OH.

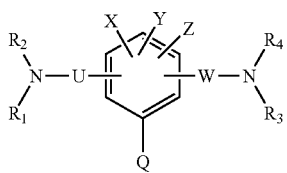
V

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reagents and agents in the syntheses shown below.

Scheme 1

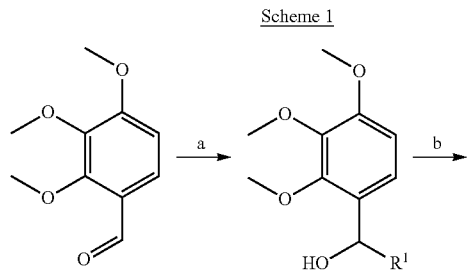

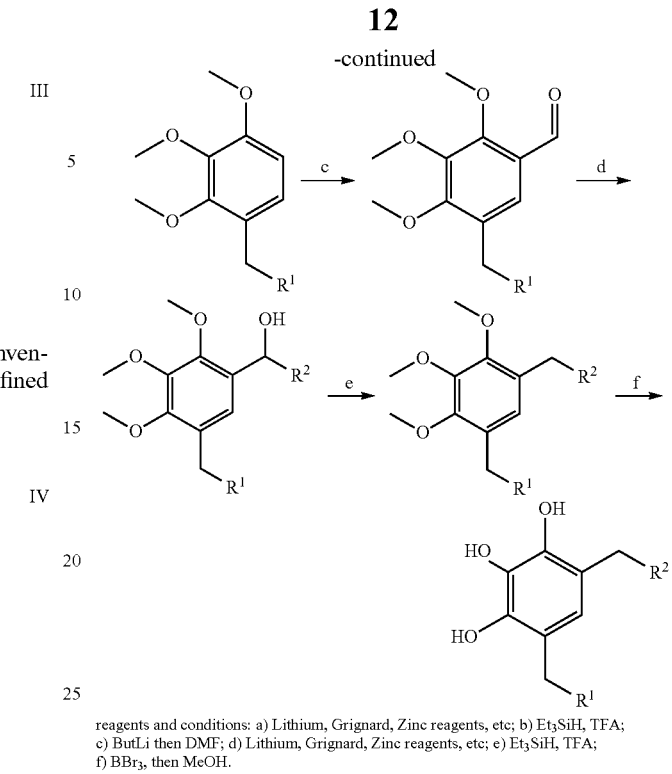

reagents and conditions: a) Lithium, Grignard, Zinc reagents, etc; b) Et₃SiH, TFA; c) ButLi then DMF; d) Lithium, Grignard, Zinc reagents, etc; e) Et₃SiH, TFA; f) BBr₃, then MeOH.

Multi-substituted phenol analogues may be synthesized as shown in Scheme 1. Disubstituted pyrogallol analogues are prepared from commercially available 2,3,4-trimethoxybenzaldehyde. The addition reaction between aldehyde and nucleophilic Grignard, lithium, or zinc reagents gives a secondary alcohol with quantitative yield. The hydroxyl group is then removed by triethylsilane in trifluoroacetic acid solvent. Following a two-step protocol, an aldehyde is made regioselectively by the ortho-inducing effect of methoxyl group. The second alkyl, aryl, or heteroaryl group is introduced by repeating the same procedure. The final products are obtained by boron tribromide (BBr₃) demethylation, which is quenched by methanol. Based on the protective groups used in the intermediates, either hydrogenation or acidic hydrolysis is effective for the removal of benzyl or methoxylmethyl groups.

Scheme 2

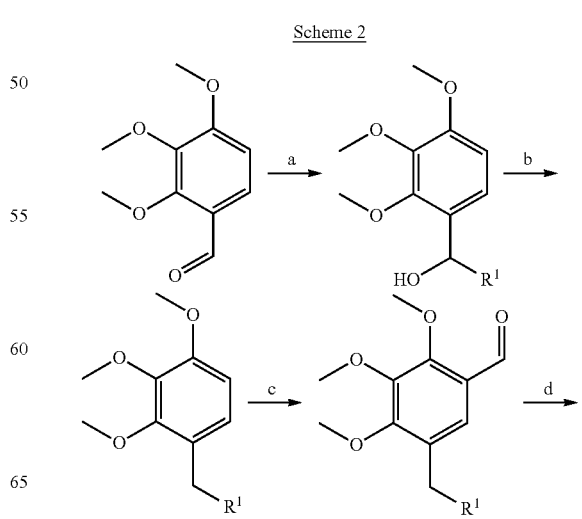

-continued

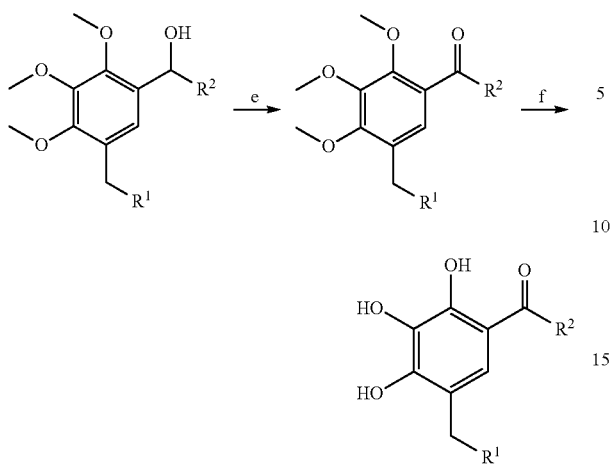

reagents and conditions: a) Lithium, Grignard, Zinc reagents, etc; b) Et₃SiH, TFA; c) ButLi then DMF; d) Lithium, Grignard, Zinc reagents, etc; e) Dess-Martin Periodinane, DCM; f) BBr₃, then MeOH.

The synthesis of mono-ketone substituted phenols, shown in Scheme 2, is largely the same as that of Scheme 1. However, the secondary alcohol can be oxidized to ketone by Dess-Martin periodinane, a mild oxidant proved much more effective than PCC, activated MnO₄ for this class of compounds. The same protective group removal strategy is used to get the final acylated phenol analogues.

Scheme 3

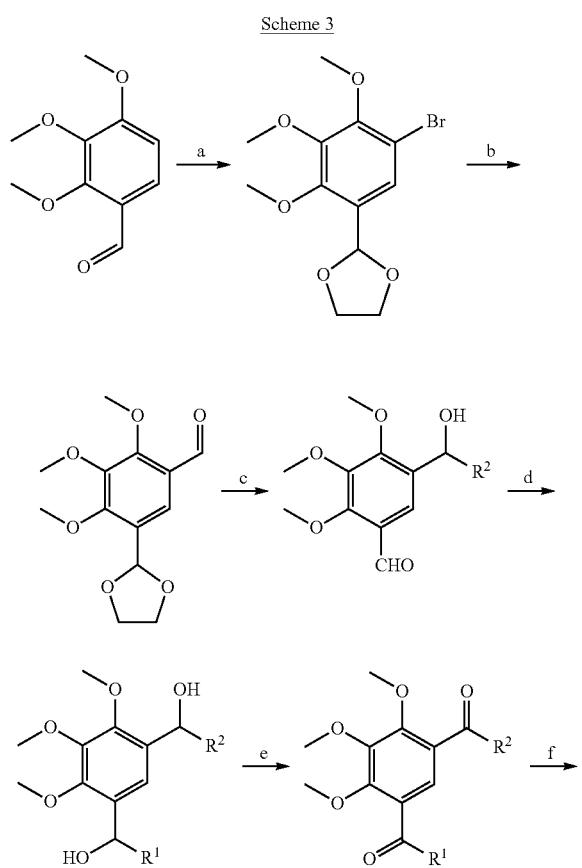

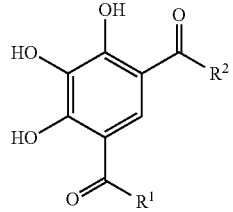

reagents and conditions: a) 1. Br₂, AcOH; 2. TsOH, ethylene glycol; b) BuTLi then DMF; c) 1. Lithium, Grignard, Zinc reagents, etc; 2. TsOH, acetone; d) Lithium, Grignard, Zinc reagents, etc; e) Dess-Martin Periodinane, DCM; f) BBr₃, then MeOH.

The diacyl substituted phenols are prepared from simple aldehydes as shown in Scheme 3. First, methoxybenzaldehyde is brominated regioselectively by bromine in acetic acid. After converting the active aldehyde group to 1,3-dioxolane, the second aldehyde group is introduced by bromine-metal exchange reaction. The first alkyl or aryl groups are incorporated into the molecule by addition reaction with one of the aldehyde groups protected. By using p-toluenesulfonic acid as a catalyst, the aldehyde protective group is removed in acetone very quickly (longer reaction time will lead to the decomposition of the secondary alcohol). The two alcohol groups are oxidized to diketone with moderate yield. By using BBr₃ or HBr/HOAc, the protective groups are removed to give clean final products.

Scheme 4

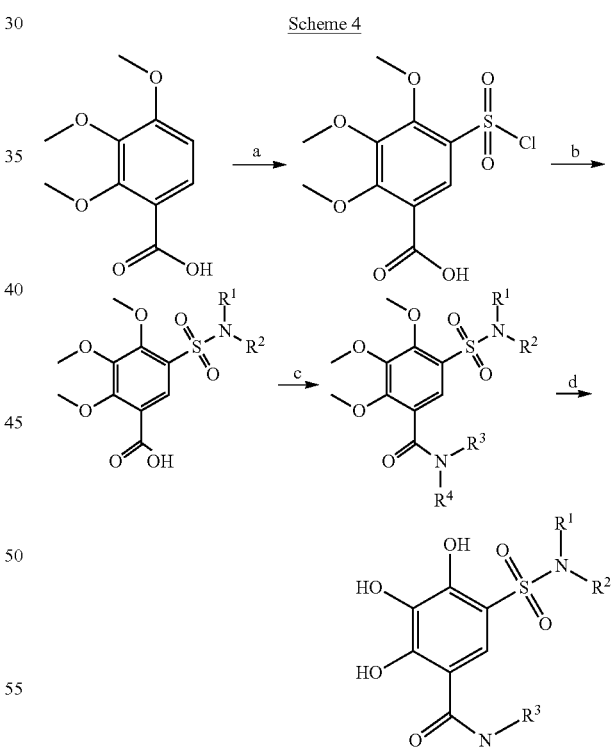

reagents and conditions: a) chlorosulfonic acid; b) NHR₁R₂, NEt₃; c) NHR₃R₄, EDCI, HOBt, NEt₃; d) BBr₃, then MeOH.

The synthesis of aminosulfonyl phenols is based on simple amide coupling reactions as shown in Scheme 4. Using commercially available methoxybenzoic acid, the sulfonyl chloride is made with excellent regioselectivity, thanks to the positioning effects from the methoxyl and carboxylic groups.

The sulfonamide is made by stirring of the sulfonyl chloride with amine under basic conditions. By performing the classic EDCI/HOBt coupling reaction, the amide is obtained. Different amines are used in both amide bond formation reactions to achieve molecular diversity. The final phenols are obtained by using either BBr$_3$ or hydrogenation based on the properties of protective groups.

Additional compounds of the present invention can be synthesized using the following schemes. The compounds can be synthesized from acyl chlorides and aniline. Schemes V, VI, and VII provide different methodologies for the synthesis of various of acyl chlorides.

butyl lithium at low temperature (−78° C.). The lithium reagent is reacted with commercially available substituted benzene aldehyde to obtain compound 2 in high yield. Removal of the hydroxyl group in 2 in a H$_2$ atmosphere and in presence of a Pd—C catalyst yields 3, which is brominated with Br$_2$ to afford 4. This reaction is regio-selective. Using butyl lithium again to exchange bromine in 4 generates another lithium reagent, which is treated with dry ice to afford acids 5. Compound 5 is easily transformed to acyl chlorides 6 with SOCl$_2$ in benzene using DMF as the catalyst.

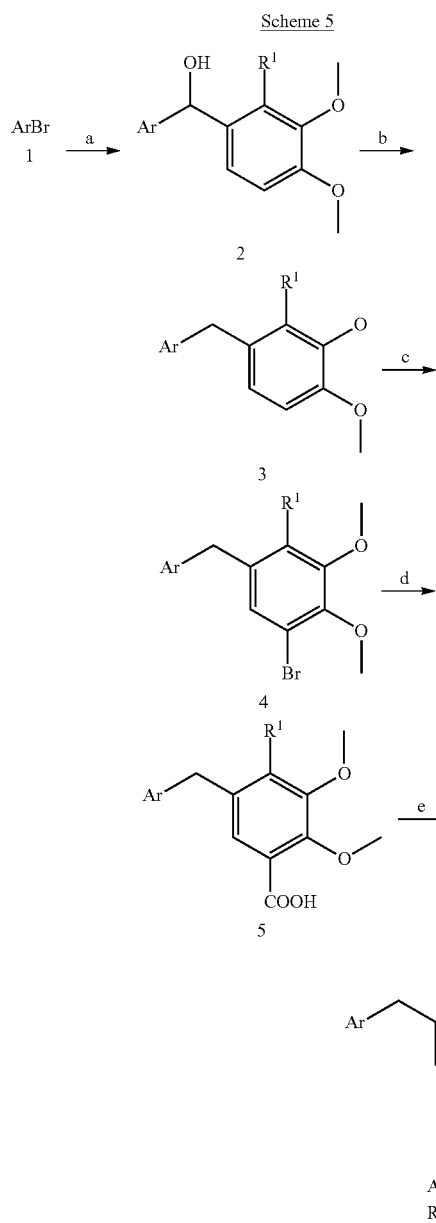

Scheme 5

Ar: Aryl
R$^1$: alkyl reagents and conditions : a. n-buLi/-78° C./THF then substituted benzenealdehyde; b. H$_2$/Pd—C/EtOAc; c. Br$_2$/-60° C./CHCl$_3$; d. n-buLi/-78° C./THF then CO$_2$; e. SOCl$_2$/DMF (cat)/benzene/70° C.

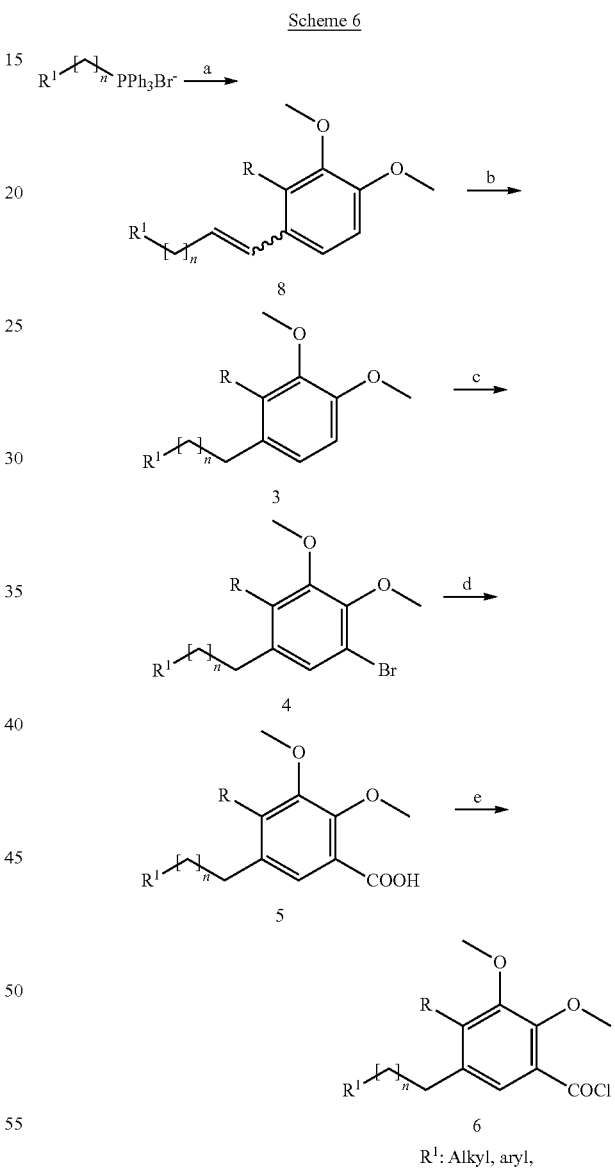

Scheme 6

R$^1$: Alkyl, aryl,
R: methoxyl, H,
n = 0, 1, 2, 3, reagents and conditions : a. n-buLi/-78° C./THF then substituted benzenealdehyde; b. H$_2$/Pd—C/EtOAc; c. Br$_2$/-60° C./CHCl$_3$; d. n-buLi/-78° C./THF then CO$_2$; e. SOCl$_2$/DMF (cat)/benzene/70° C.

Scheme 5 presents a method to synthesis acyl chlorides with one or more than one carbon linker in 5-position. Aromatic bromide can be transformed to aromatic lithium with In Scheme 6 the synthesis is the same as in Scheme 5 but the starting material is triphenylphosphate, which is reacted with substituted benzenealdehyde via Wittig reaction to afford 8. The double bond is reduced to generate 3.

Scheme 7

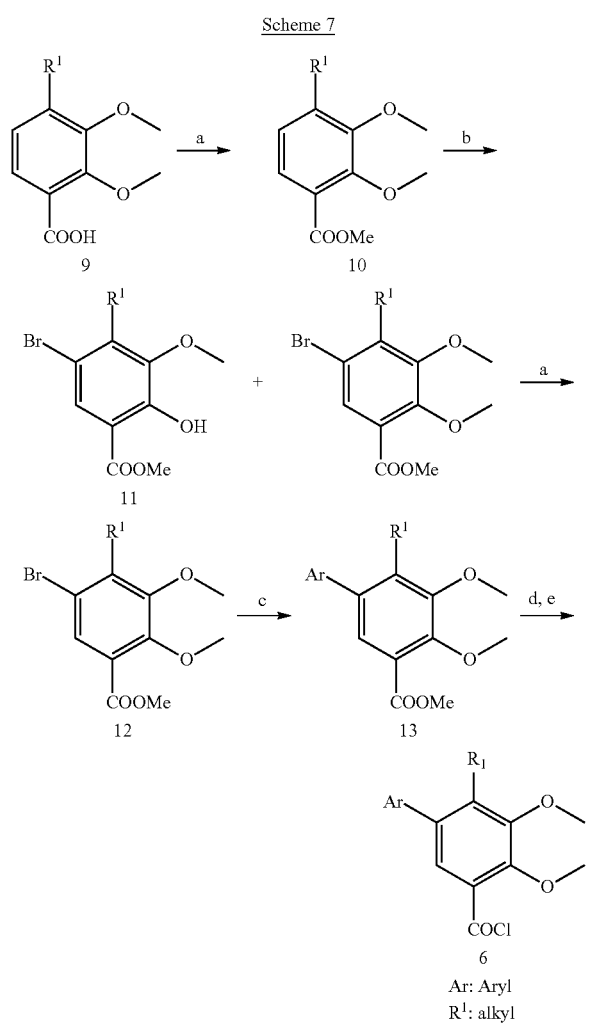

reagents and conditions: a. $H_2CO_3/CH_3I/DMF$; b. $Br_2/CH_2Cl_2/rt$;
c. $Pd(PPh_3)_4$ (10 mol %)/$Na_2CO_3$/DEG-$H_2O$/aromic boronic acid/100° C.;
d. MeOH/KOH/$H_2O$/80° C.; e. $SOCl_2$/DMF (cat)/benzene/70° C.

Scheme 7 discloses a method for the synthesis of acyl chlorides without carbon linker in 5-position. Compounds 12 may be afforded in two steps from commercially available compound 9 in high yield. Any compound 10 having a methyl group removed by the bromide to produce compound 11 may be transformed to compound 12 with methylation. The Suzuki coupling reaction may be used to generate 13. Compounds 13 may be hydrolyzed in a MeOH/KOH system, and then acylated with $SOCl_2$ to afford acyl chloride in high yield.

Scheme 8

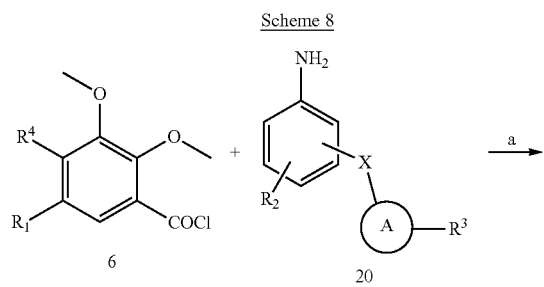

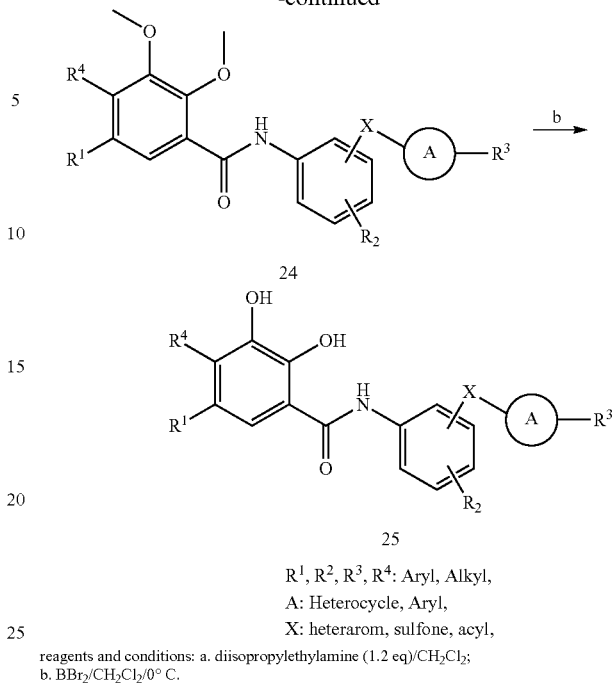

$R^1$, $R^2$, $R^3$, $R^4$: Aryl, Alkyl,
A: Heterocycle, Aryl,
X: heterarom, sulfone, acyl, reagents and conditions: a. diisopropylethylamine (1.2 eq)/$CH_2Cl_2$;
b. $BBr_3$/$CH_2Cl_2$/0° C.

In Scheme 8, condensation of acyl chlorides 6 with anilines 20 under standard conditions followed by removal of the protective methyl groups directly with $BBr_3$ affords the final target molecules 25.

An important aspect of the present invention is that compounds of Formula I induce apoptosis and also potentiate the induction of apoptosis in response to apoptosis induction signals. Therefore, it is contemplated that these compounds sensitize cells to inducers of apoptosis, including cells that are resistant to such inducers. The anti-apoptotic Bcl-2 family member inhibitors of the present invention can be used to induce apoptosis in any disorder that can be treated, ameliorated, or prevented by the induction of apoptosis. Thus, the present invention provides compositions and methods for targeting animals characterized as overexpressing an anti-apoptotic Bcl-2 family member protein. In some of the embodiments, the cells (e.g., cancer cells) show elevated expression levels of anti-apoptotic Bcl-2 family member proteins as compared to non-pathological samples (e.g., non-cancerous cells). In other embodiments, the cells operationally manifest elevated expression levels of anti-apoptotic Bcl-2 family member proteins by virtue of executing the apoptosis program and dying in response to an inhibiting effective amount of a compound of Formula I, said response occurring, at least in part, due to the dependence in such cells on anti-apoptotic Bcl-2 family member protein function for their survival.

In another embodiment, the invention pertains to modulating an apoptosis associated state which is associated with one or more apoptosis modulating agents. Examples of apoptosis modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAILR1 or TRAILR2, Bcl-2, p53, BAX, BAD, Akt, CAD, PI3 kinase, PP1, and caspase proteins. Other agents involved in the initiation, decision and degradation phase of apoptosis are also included. Examples of apoptosis modulating agents include agents, the activity, presence, or change in concentration of which, can modulate apoptosis in a subject. Preferred apoptosis modulating agents are inducers of apoptosis, such as TNF or a TNF-related ligand, particularly a TRAMP ligand, a Fas/CD95 ligand, a TNFR-1 ligand, or TRAIL.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents.

In some embodiments, infections suitable for treatment with the compositions and methods of the present invention include, but are not limited to, infections caused by viruses, bacteria, fungi, mycoplasma, prions, and the like.

Some embodiments of the present invention provide methods for administering an effective amount of a compound of Formula I and at least one additional therapeutic agent (including, but not limited to, chemotherapeutic antineoplastics, apoptosis modulating agents, antimicrobials, antivirals, antifungals, and anti-inflammatory agents) and/or therapeutic technique (e.g., surgical intervention, and/or radiotherapies).

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In preferred embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAILR1 or TRAILR2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of Formula I and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |

TABLE 1-continued

| | | |
|---|---|---|
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzene-butanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetra-hydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by Streptomyces parvullus, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexo-pyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenyliso-serine, N-tert-butyl ester, 13-ester | Taxotere | Aventis Pharmaceuticals, Inc., |

TABLE 1-continued

| | | |
|---|---|---|
| with 5b-20-epoxy-12a,4,7b,10b,13a-hexahydroxytax-11-en-9-one 4-acetate 2-benzoate, trihydrate) | | Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-pentafluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)[6],Azgly[10]LHRH; pyro-Glu-His-Trp-Ser-Tyr-D-Ser(But)-Leu-Arg-Pro-Azgly-NH2 acetate [$C_{59}H_{84}N_{18}O_{14}.(C_2H_4O_2)_x$] | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino] benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |

TABLE 1-continued

| | | |
|---|---|---|
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O']platinum) | Eloxatin | Sanofi Synthelabo, Inc., NY, NY |
| Paclitaxel (5β, 20-Epoxy-1,2a,4,7β,10β,13a-hexahydroxytax-11-en-9-one 4,10-diacetate 2-benzoate 13-ester with (2R, 3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethylamine)butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[[(methylnitrosoamino)carbonyl] amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1"-phosphino-thioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyl-adriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxy]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Preferred conventional anticancer agents for use in administration with the present compounds include, but are not limited to, adriamycin, 5-fluorouracil, etoposide, camptothecin, actinomycin D, mitomycin C, cisplatin, docetaxel, gemcitabine, carboplatin, oxaliplatin, bortezomib, gefitinib, and bevacizumab. These agents can be prepared and used singularly, in combined therapeutic compositions, in kits, or in combination with immunotherapeutic agents, and the like.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of Formula I with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (ludR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to an animal preferably is about 0.01 Gray (Gy) to about 100 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of Formula I and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2 3, 4, 5, 10, 12, or 18 hours, 1, 2, 3, 4, 5, or 6 days, 1, 2, 3, or 4 weeks prior to the administration of the therapeutic or anticancer agent. In some embodiments, the compound is administered after the therapeutic or anticancer agent, e.g., 0.5, 1, 2 3, 4, 5, 10, 12, or 18 hours, 1, 2, 3, 4, 5, or 6 days, 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. Preferably, about 0.01 to about 10 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 1000 mg, preferably about 0.1 to about 100 mg of the compound. The unit dose may be administered one or more times daily as one or more tablets or capsules each containing from about 0.1 to about 10, conveniently about 0.25 to 50 mg of the compound or its solvates.

In a topical formulation, the compound may be present at a concentration of about 0.01 to 100 mg per gram of carrier. In a preferred embodiment, the compound is present at a concentration of about 0.07-1.0 mg/ml, more preferably, about 0.1-0.5 mg/ml, most preferably, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

Synthesis of Compounds of Formula I

General Methods: NMR spectra were acquired at a proton frequency of 300 MHz. $^1$H chemical shifts are reported with $CD_3COCD_3$ or $CDCl_3$ as internal standards. $^{13}$C chemical shifts are reported with $CD_3COCD_3$ or $CDCl_3$ as internal standards.

The following compounds (Tables 2-4) were synthesized and their structures analyzed by the general procedures described above.

TABLE 2

| Name | Compound |
| --- | --- |
| TM-103 | (structure: benzene ring with OH, HO, HO, $C_6H_{13}$, and isopropyl substituents) |
| TM-104 | (structure: benzene ring with OH, HO, HO, isopropyl, and C(=O)$C_5H_{11}$ substituents) |
| TM-105 | (structure: benzene ring with OH, HO, HO, $C_{11}H_{23}$, and isopropyl substituents) |
| TM-106 | (structure: benzene ring with OH, HO, HO, isopropyl, and C(=O)$C_{10}H_{21}$ substituents) |

TABLE 2-continued

| Name | Compound |
|---|---|
| TM-107 | 2-(2,3,4-trihydroxy-5-isopropylphenyl)ethyl-naphthalene |
| TM-108 | 1-(2,3,4-trihydroxy-5-isopropylphenyl)-2-(naphthalen-2-yl)ethanone |
| TM-109 | 3-pentadecyl-6-isopropylbenzene-1,2,4-triol (C₁₅H₃₁ chain) |
| TM-110 | 1-(2,3,4-trihydroxy-5-isopropylphenyl)pentadecan-1-one (C₁₄H₂₉ chain) |
| TM-111 | methoxy/hydroxy variant with C₁₅H₃₁ chain and isopropyl |
| TM-121 | 3-undecyl-6-benzylbenzene-1,2,4-triol (C₁₁H₂₃ chain) |

TABLE 2-continued
| Name | Compound |
|---|---|
| TM-122 | 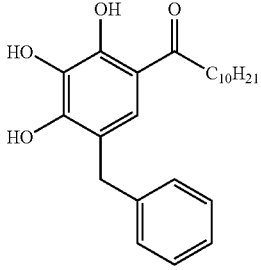 |
| TM-123 | 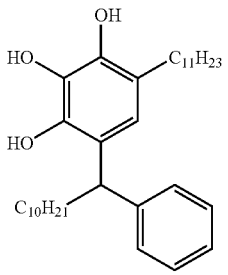 |
| TM-124 | 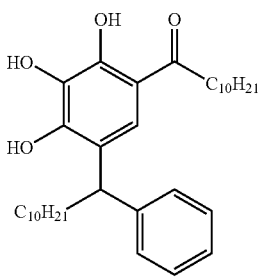 |
| TM-125 | 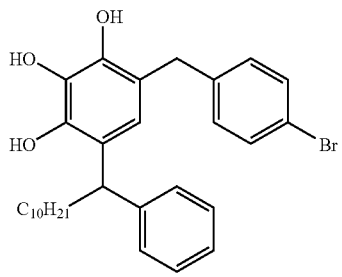 |
| TM-126 | 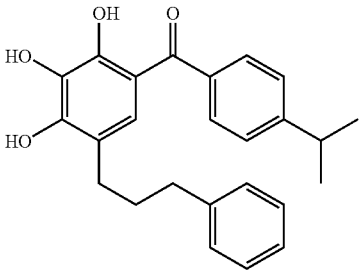 [SMILES: CC(C)c1ccc(C(=O)c2cc(CCCc3ccccc3)c(O)c(O)c2O)cc1] |

TABLE 2-continued
| Name | Compound |
|---|---|
| TM-127 | 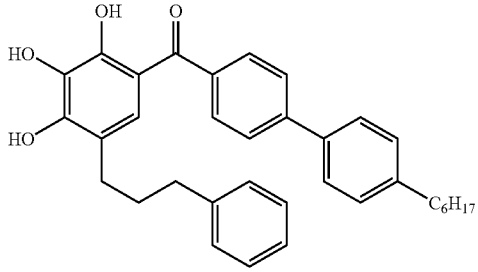 |
| TM-128 | 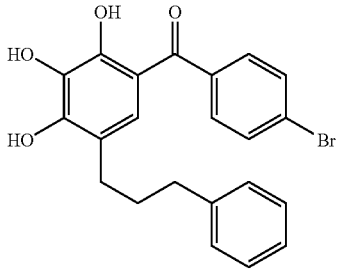 [SMILES: O=C(c1ccc(Br)cc1)c1cc(CCCc2ccccc2)c(O)c(O)c1O] |
| TM-129 | 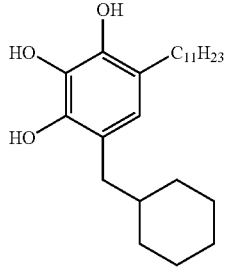 |
| TM-130 | 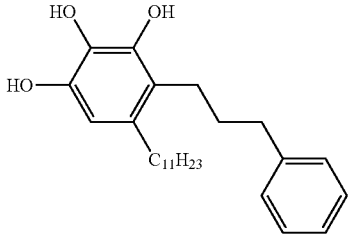 |
| TM-132 | 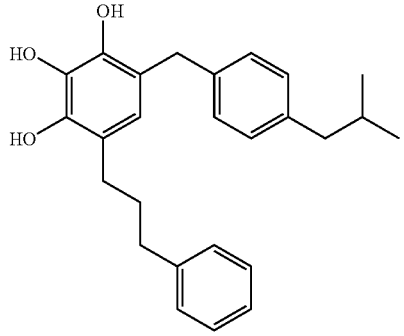 [SMILES: CC(C)Cc1ccc(Cc2cc(CCCc3ccccc3)c(O)c(O)c2O)cc1] |

TABLE 2-continued
| Name | Compound |
|---|---|
| TM-133 | 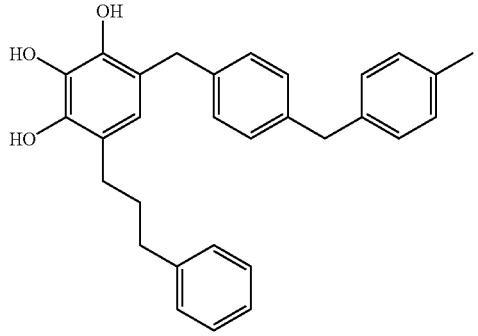 [SMILES: Cc1ccc(Cc2ccc(Cc3cc(CCCc4ccccc4)c(O)c(O)c3O)cc2)cc1] |
| TM-134 | 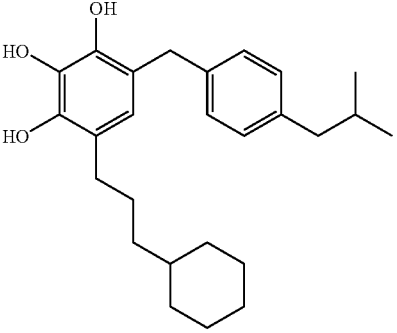 [SMILES: CC(C)Cc1ccc(Cc2cc(CCCC3CCCCC3)c(O)c(O)c2O)cc1] |
| TM-135 | 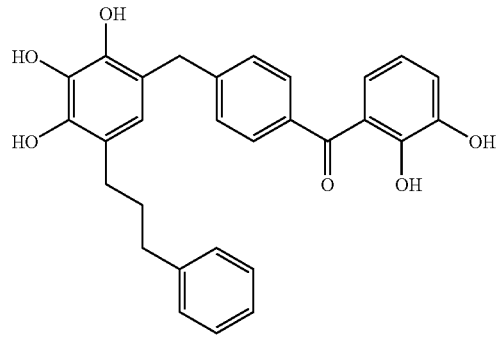 [SMILES: O=C(c1ccc(Cc2cc(CCCc3ccccc3)c(O)c(O)c2O)cc1)c1cccc(O)c1O] |
| TM-136 | 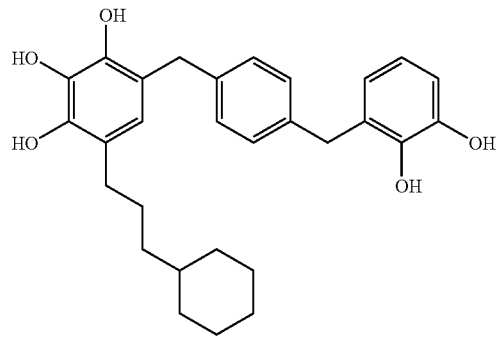 [SMILES: Oc1cccc(Cc2ccc(Cc3cc(CCCC4CCCCC4)c(O)c(O)c3O)cc2)c1O] |

TABLE 2-continued

| Name | Compound |
|------|----------|
| TM-137 | |
| TM-140 | |
| TM-141 | |
| TM-142 | |
| TM-143 | |

TABLE 2-continued
| Name | Compound |
|---|---|
| TM-144 | 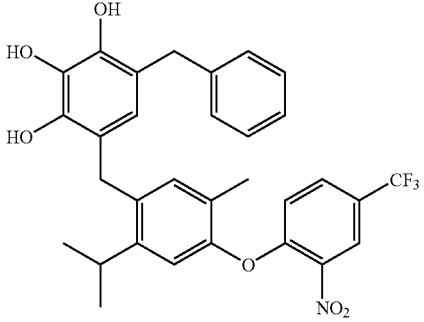 [SMILES: Cc1cc(Cc2cc(Cc3ccccc3)c(O)c(O)c2O)c(C(C)C)cc1Oc1ccc(C(F)(F)F)cc1[N+](=O)[O-]] |
| TM-145 | 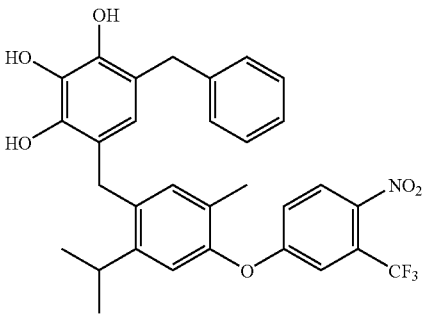 [SMILES: Cc1cc(Cc2cc(Cc3ccccc3)c(O)c(O)c2O)c(C(C)C)cc1Oc1ccc([N+](=O)[O-])c(C(F)(F)F)c1] |
| TM-146 | 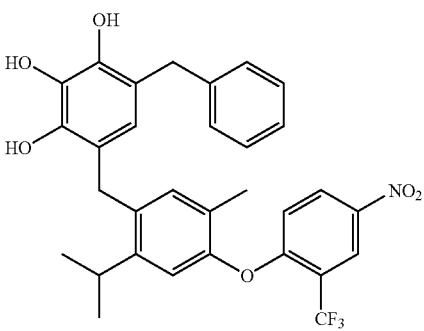 [SMILES: Cc1cc(Cc2cc(Cc3ccccc3)c(O)c(O)c2O)c(C(C)C)cc1Oc1ccc([N+](=O)[O-])cc1C(F)(F)F] |
| TM-147 | 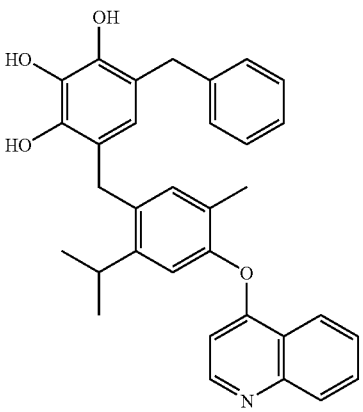 [SMILES: Cc1cc(Cc2cc(Cc3ccccc3)c(O)c(O)c2O)c(C(C)C)cc1Oc1ccnc2ccccc12] |

TABLE 2-continued

| Name | Compound |
|---|---|
| TM-148 | |
| TM-149 | |
| TM-150 | |
| TM-152 | |

| Name | Compound |
|---|---|
| TM-153 | (structure: 3,4,5-trihydroxy benzyl-substituted phenyl linked via methylene to 2-isopropyl-4-(quinolin-2-yloxy)phenyl) |
| TM-154 | (structure: 3,4,5-trihydroxy benzyl-substituted phenyl linked via methylene to 2-isopropyl-4-(quinolin-4-yloxy)phenyl) |
| TM-155 | (structure: 3,4,5-trihydroxy benzyl-substituted phenyl linked via methylene to 2-isopropyl-4-(2-trifluoromethyl-4-nitrophenoxy)phenyl) |
| TM-156 | (structure: 3,4,5-trihydroxy benzyl-substituted phenyl linked via methylene to 2-isopropyl-4-((2-methylquinolin-4-yl)oxy)phenyl) |
| TM-157 | (structure: 2,3,4-trihydroxyphenyl-CH$_2$-(4-phenoxyphenyl)) |

TABLE 2-continued

| Name | Compound |
|---|---|
| TM-158 | *5-bromo-3-(4-phenoxybenzyl)benzene-1,2,3-triol* |
| TM-159 | *5-isopropyl-3-(4-phenoxybenzyl)benzene-1,2,3-triol* |
| TM-160 | *5-isobutyl-3-(4-phenoxybenzyl)benzene-1,2,3-triol* |
| TM-161 | *3-(2,2-dimethylpropyl)-5-(4-phenoxybenzyl)benzene-1,2,3-triol* |
| TM-162 | *5-(4-phenoxybenzyl)-6-(2-phenylethyl)benzene-1,2,3-triol* |
| TM-163 | *5-(4-phenoxybenzyl)-6-(3-phenylpropyl)benzene-1,2,3-triol* |

TABLE 2-continued
| Name | Compound |
|---|---|
| TM-164 | 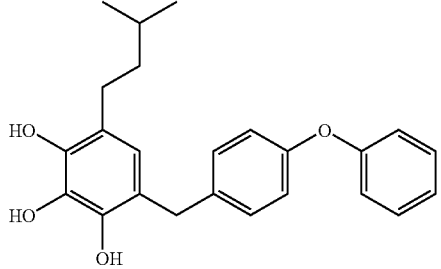 [SMILES: CC(C)CCc1cc(Cc2ccc(Oc3ccccc3)cc2)c(O)c(O)c1O] |
| TM-165 | 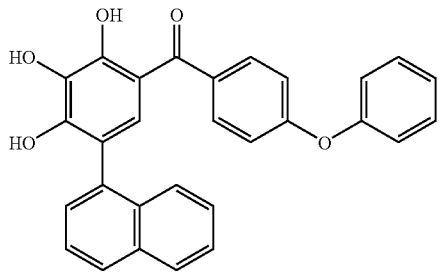 [SMILES: O=C(c1ccc(Oc2ccccc2)cc1)c1cc(-c2cccc3ccccc23)c(O)c(O)c1O] |
| TM-166 | 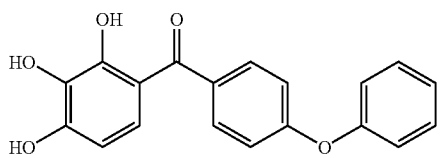 [SMILES: O=C(c1ccc(Oc2ccccc2)cc1)c1ccc(O)c(O)c1O] |
| TM-167 | 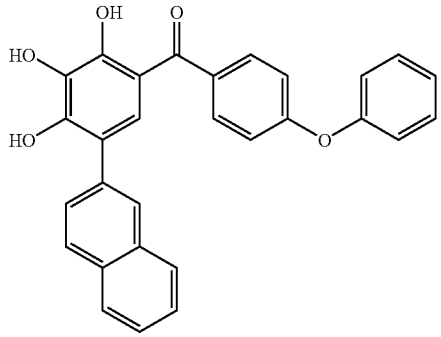 [SMILES: O=C(c1ccc(Oc2ccccc2)cc1)c1cc(-c2ccc3ccccc3c2)c(O)c(O)c1O] |
| TM-168 | 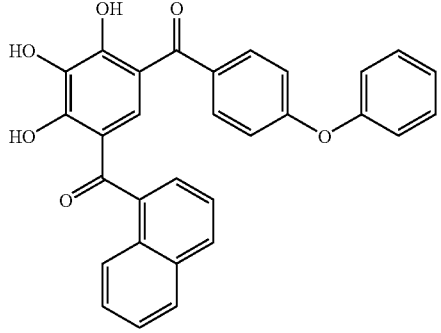 [SMILES: O=C(c1ccc(Oc2ccccc2)cc1)c1cc(C(=O)c2cccc3ccccc23)c(O)c(O)c1O] |

TABLE 2-continued
| Name | Compound |
|---|---|
| TM-169 | 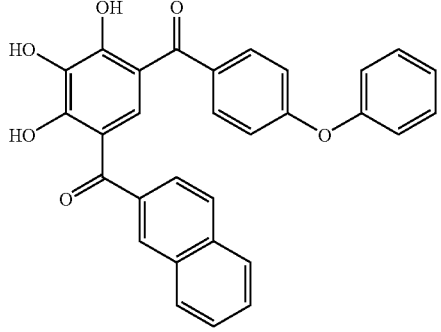 [SMILES: O=C(c1ccc(Oc2ccccc2)cc1)c1cc(C(=O)c2ccc3ccccc3c2)c(O)c(O)c1O] |
| TM-170 | 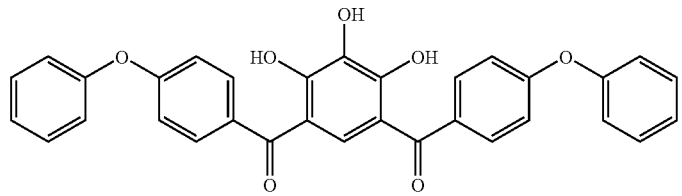 [SMILES: O=C(c1ccc(Oc2ccccc2)cc1)c1cc(C(=O)c2ccc(Oc3ccccc3)cc2)c(O)c(O)c1O] |
| TM-171 | 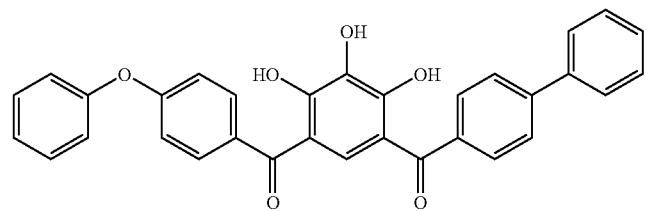 [SMILES: O=C(c1ccc(Oc2ccccc2)cc1)c1cc(C(=O)c2ccc(-c3ccccc3)cc2)c(O)c(O)c1O] |
| TM-172 | 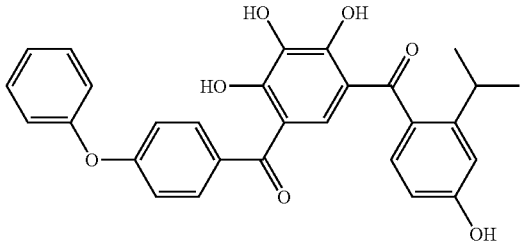 [SMILES: CC(C)c1cc(O)ccc1C(=O)c1cc(C(=O)c2ccc(Oc3ccccc3)cc2)c(O)c(O)c1O] |
| TM-173 | 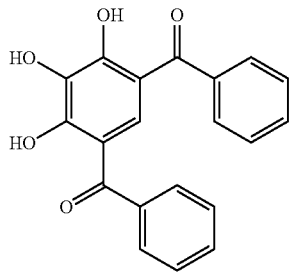 [SMILES: O=C(c1ccccc1)c1cc(C(=O)c2ccccc2)c(O)c(O)c1O] |
| TM-174 | 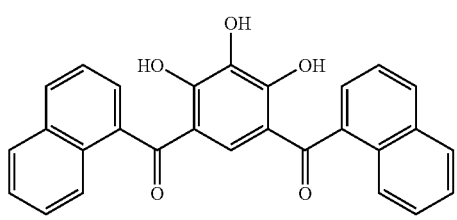 [SMILES: O=C(c1cc(C(=O)c2cccc3ccccc23)c(O)c(O)c1O)c1cccc2ccccc12] |

TABLE 2-continued

| Name | Compound |
|---|---|
| TM-175 | |
| TM-176 | |
| TM-177 | |
| TM-178 | |
| TM-179 | |
| TM-180 | |
| TM-183 | |

TABLE 2-continued

| Name | Compound |
|---|---|
| TM-190 | |
| TM-191 | |
| TM-192 | |
| TM-193 | |
| TM-194 | |

TABLE 2-continued

| Name | Compound |
|---|---|
| TM-195 | |
| TM-196 | |
| TM-197 | |
| TM-198 | |
| TM-199 | |

TABLE 2-continued

| Name | Compound |
|---|---|
| TM-200 (1200) | |
| TM-1201 | |
| TM-1202 | |
| TM-1203 | |
| TM-1205 | |

TABLE 2-continued
| Name | Compound |
|---|---|
| TM-1206 | 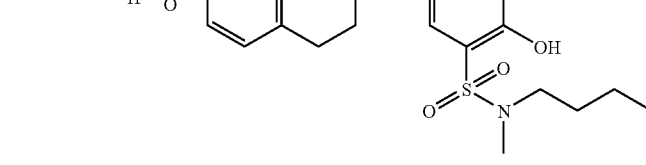 |
| TM-1207 | 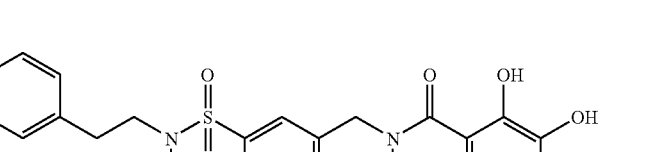 |
| TM-1208 | 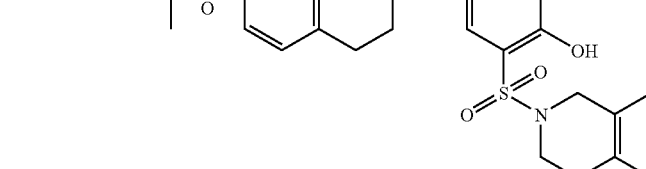 |
| TM-1209 | 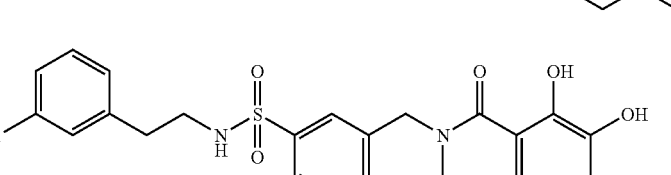 |
| TM-1210 | 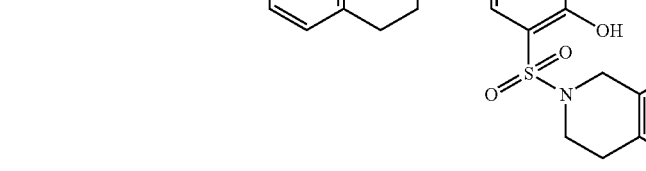 |

TABLE 2-continued

| Name | Compound |
|---|---|
| TM-1211 | |
| TM-1212 | |
| TM-1213 | |
| TM-1214 | |
| TM-1215 | |

TABLE 2-continued
| Name | Compound |
|---|---|
| TM-1216 | 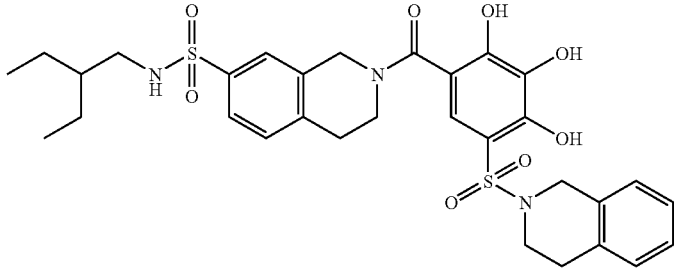 [SMILES: CCC(CC)CNS(=O)(=O)c1ccc2c(c1)CN(C(=O)c1cc(S(=O)(=O)N3CCc4ccccc4C3)c(O)c(O)c1O)CC2] |
| TM-1217 | 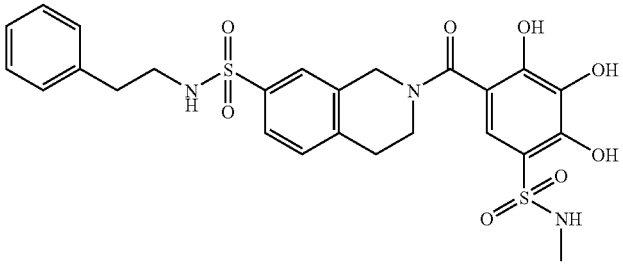 [SMILES: CNS(=O)(=O)c1cc(C(=O)N2CCc3ccc(S(=O)(=O)NCCc4ccccc4)cc3C2)c(O)c(O)c1O] |
| TM-1218 | 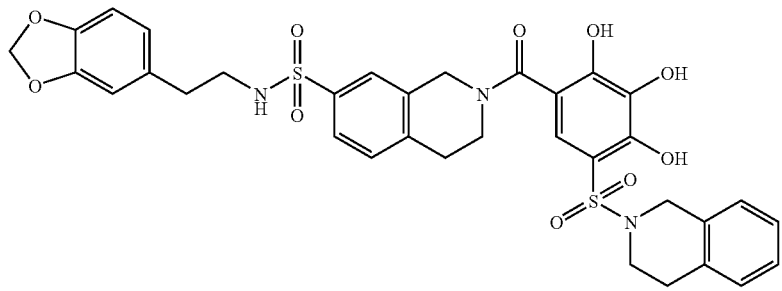 [SMILES: O=C(c1cc(S(=O)(=O)N2CCc3ccccc3C2)c(O)c(O)c1O)N1CCc2ccc(S(=O)(=O)NCCc3ccc4c(c3)OCO4)cc2C1] |
| TM-1219 | 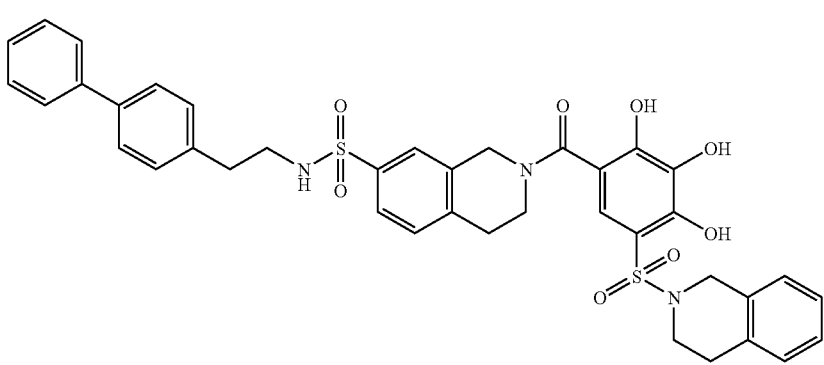 [SMILES: O=C(c1cc(S(=O)(=O)N2CCc3ccccc3C2)c(O)c(O)c1O)N1CCc2ccc(S(=O)(=O)NCCc3ccc(-c4ccccc4)cc3)cc2C1] |
| TM-1220 | 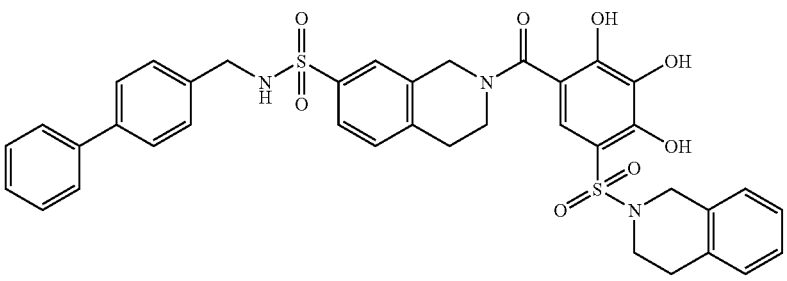 [SMILES: O=C(c1cc(S(=O)(=O)N2CCc3ccccc3C2)c(O)c(O)c1O)N1CCc2ccc(S(=O)(=O)NCc3ccc(-c4ccccc4)cc3)cc2C1] |

TABLE 2-continued
| Name | Compound |
|---|---|
| TM-1221 | 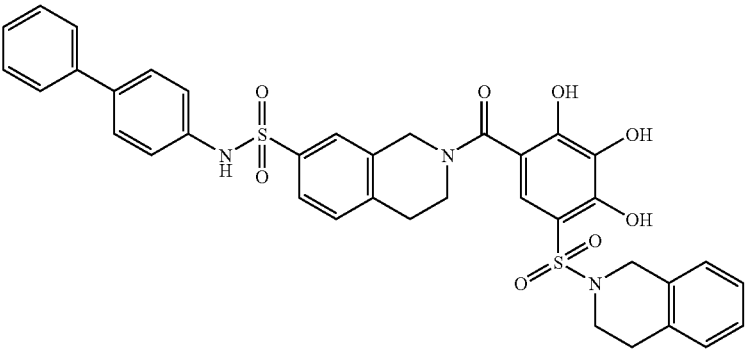 [SMILES: O=C(c1cc(S(=O)(=O)N2CCc3ccccc3C2)c(O)c(O)c1O)N1CCc2ccc(S(=O)(=O)Nc3ccc(-c4ccccc4)cc3)cc2C1] |
| TM-1222 | 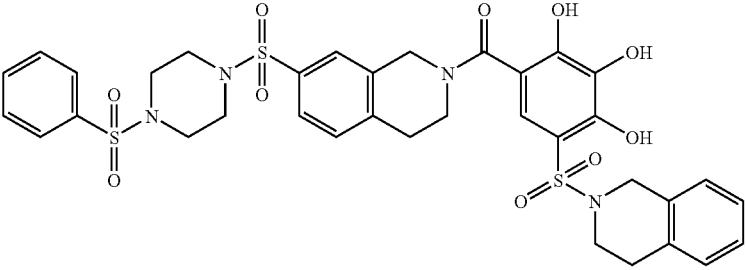 [SMILES: O=C(c1cc(S(=O)(=O)N2CCc3ccccc3C2)c(O)c(O)c1O)N1CCc2ccc(S(=O)(=O)N3CCN(S(=O)(=O)c4ccccc4)CC3)cc2C1] |
| TM-1223 | 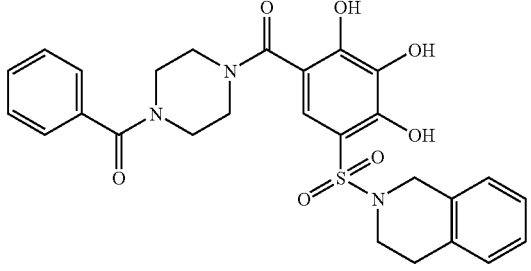 [SMILES: O=C(c1ccccc1)N1CCN(C(=O)c2cc(S(=O)(=O)N3CCc4ccccc4C3)c(O)c(O)c2O)CC1] |
| TM-1224 | 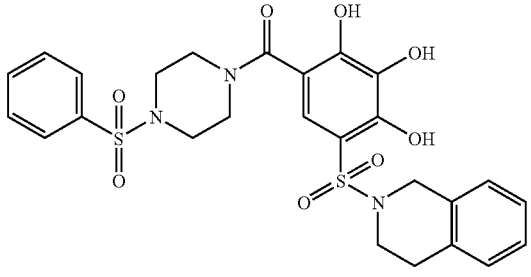 [SMILES: O=C(c1cc(S(=O)(=O)N2CCc3ccccc3C2)c(O)c(O)c1O)N1CCN(S(=O)(=O)c2ccccc2)CC1] |

TABLE 3
| Name | Compound |
|---|---|
| TW-1 | 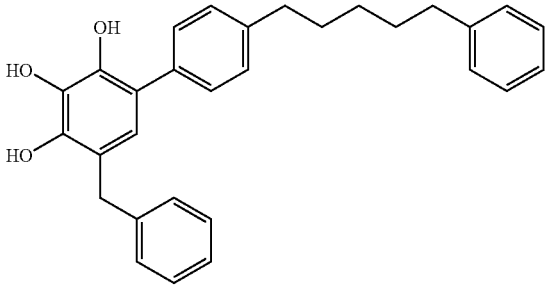<br>$C_{30}H_{30}O_3$<br>Mol. Wt.: 438.56<br>TW-1 |
| TW-2 | 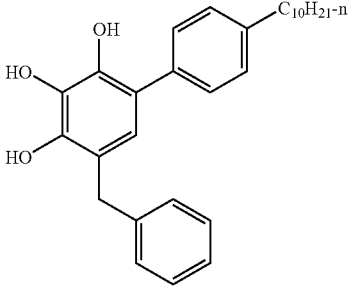<br>$C_{29}H_{36}O_3$<br>FW: 432.60<br>TW-2 |
| TW-3 | 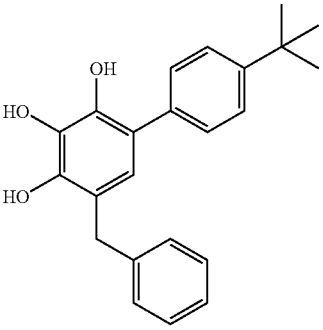<br>$C_{23}H_{24}O_3$<br>Mol. Wt.: 348.43<br>TW-3 |
| TW-4 | 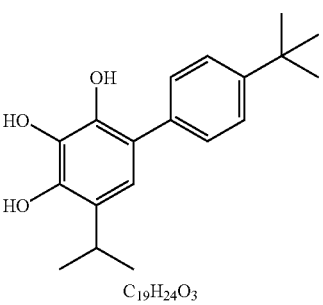<br>$C_{19}H_{24}O_3$<br>Mol. Wt.: 300.39<br>TW-4 |

TABLE 3-continued
| Name | Compound |
|---|---|
| TW-5 | 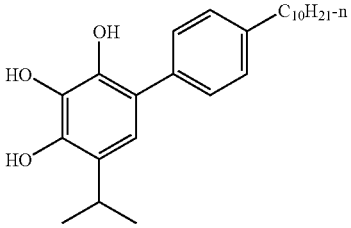<br>$C_{25}H_{36}O_3$<br>FW: 384.56<br>TW-5 |
| TW-6 | 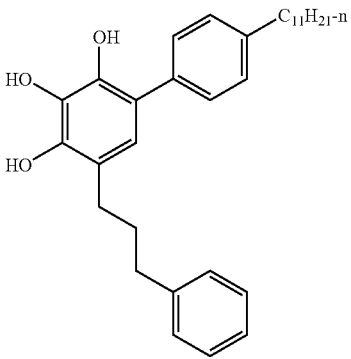<br>$C_{21}H_{19}O_3$<br>Mol. Wt.: 319.37<br>TW-6 |
| TW-7 | 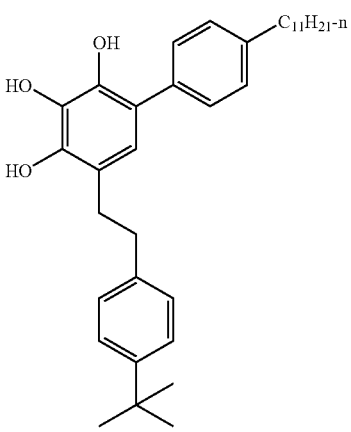<br>$C_{24}H_{25}O_3$<br>Mol. Wt.: 361.45<br>TW-7 |

TABLE 3-continued
| Name | Compound |
|---|---|
| TW-8 | 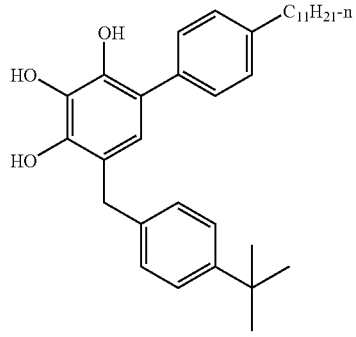<br>C$_{23}$H$_{23}$O$_3$<br>Mol. Wt.: 347.43<br>TW-8 |
| TW-9 | 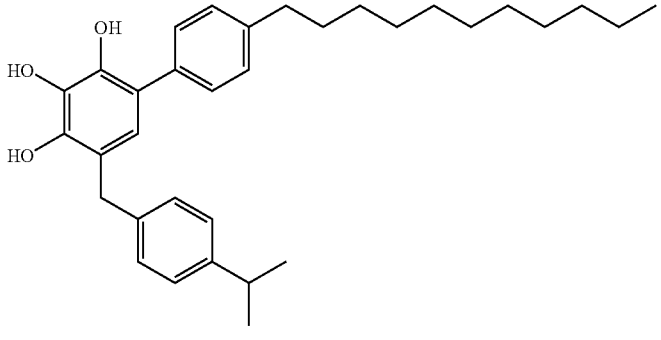<br>C$_{33}$H$_{44}$O$_3$<br>Mol. Wt.: 488.70<br>TW-9 |
| TW-10 | 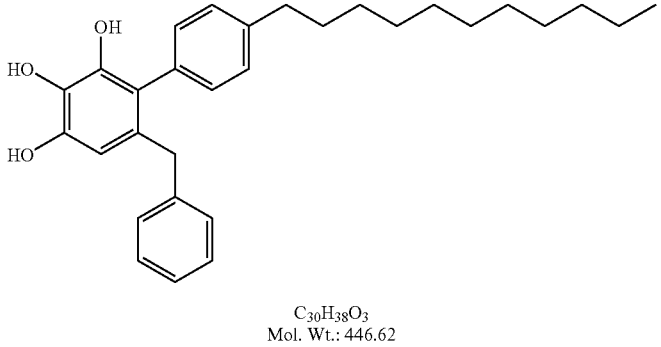<br>C$_{30}$H$_{38}$O$_3$<br>Mol. Wt.: 446.62<br>TW-10 |
| TW-11 | 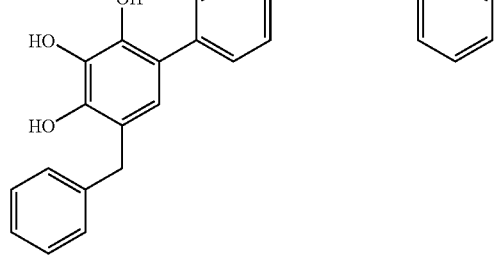<br>C$_{26}$H$_{26}$O$_3$<br>Mol. Wt.: 410.50<br>TW-11 |

TABLE 3-continued
| Name | Compound |
|---|---|
| TW-12 | 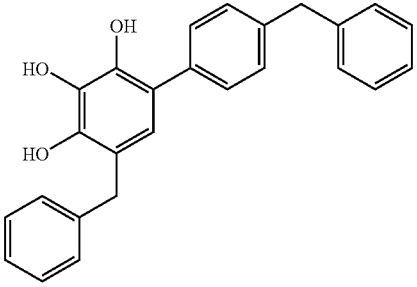<br>$C_{26}H_{22}O_3$<br>Mol. Wt.: 382.45<br>TW-12 |
| TW-13 | 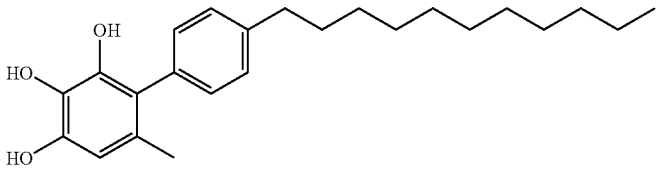<br>$C_{24}H_{34}O_3$<br>Mol. Wt.: 370.52<br>TW-13 |
| TW-14 | 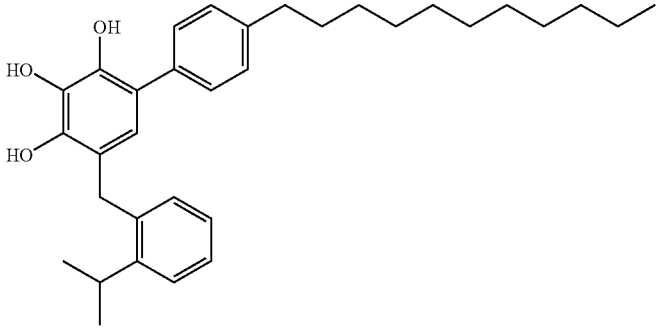<br>$C_{33}H_{44}O_3$<br>Mol. Wt.: 488.70<br>TW-14 |
| TW-15 | 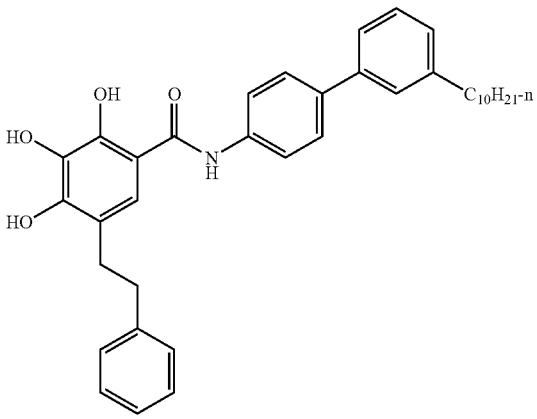<br>$C_{37}H_{43}NO_4$<br>Mol. Wt.: 565.74<br>TW-15 |

TABLE 3-continued
| Name | Compound |
|---|---|
| TW-16 | 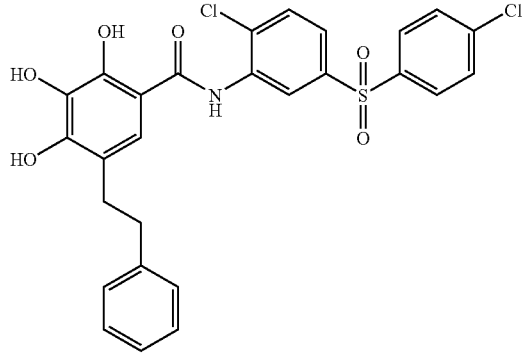<br>$C_{27}H_{21}Cl_2NO_6S$<br>Mol. Wt.: 558.43<br>TW-16 |
| TW-17 | 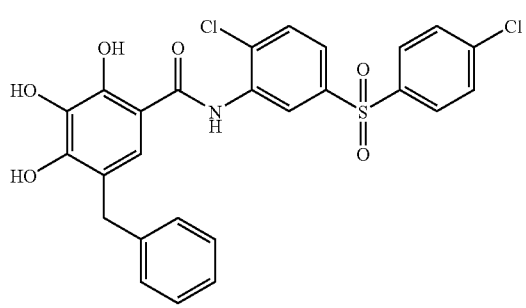<br>$C_{26}H_{18}Cl_2NO_6S$<br>Mol. Wt.: 544.40<br>TW-17 |
| TW-18 | 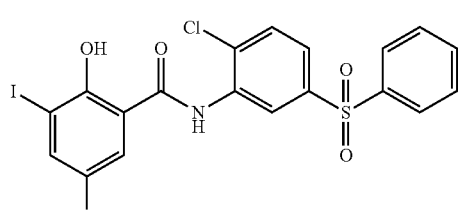<br>$C_{19}H_{12}ClI_2NO_4S$<br>Mol. Wt.: 639.63<br>TW-18 |
| TW-19 | 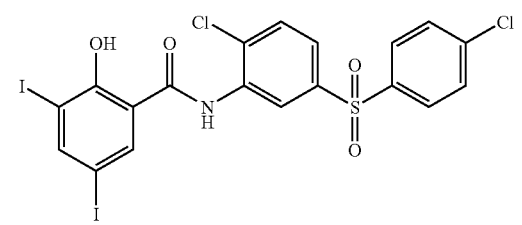<br>$C_{19}H_{11}Cl_2I_2NO_4S$<br>Mol. Wt.: 674.07<br>TW-19 |

TABLE 3-continued
| Name | Compound |
|---|---|
| TW-20 | 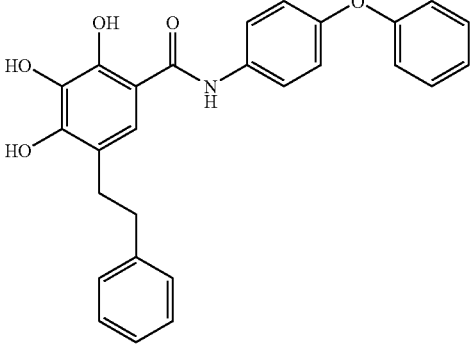<br>C$_{27}$H$_{23}$NO$_5$<br>Mol. Wt.: 441.48<br>TW-20 |
| TW-21 | 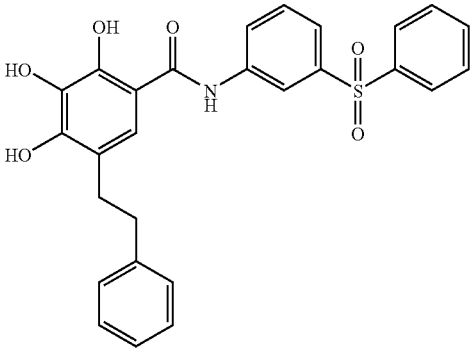<br>C$_{27}$H$_{23}$NO$_6$S<br>Mol. Wt.: 489.54<br>TW-21 |
| TW-22 | 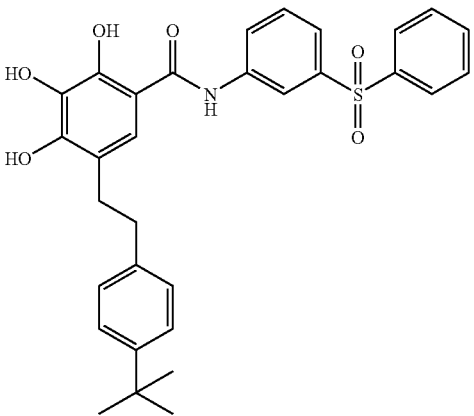<br>C$_{31}$H$_{31}$NO$_6$S<br>Mol. Wt.: 545.65<br>TW-22 |

TABLE 3-continued
| Name | Compound |
|---|---|
| TW-23 | 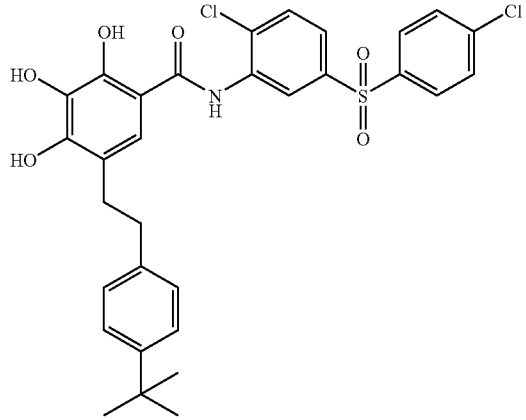<br>C₃₁H₂₉Cl₂NO₆S<br>Mol. Wt.: 614.54<br>TW-23 |
| TW-24 | 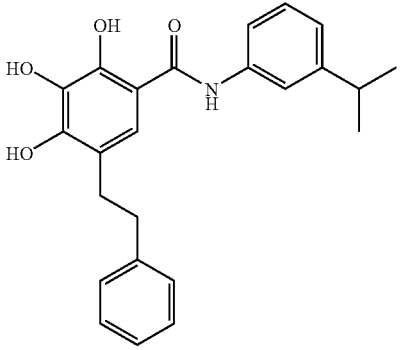<br>C₂₄H₂₅NO₄<br>Mol. Wt.: 391.46<br>TW-24 |
| TW-25 | 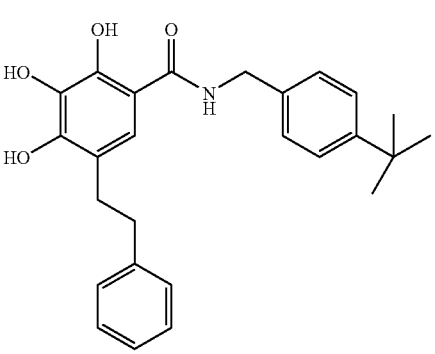<br>C₂₆H₂₉NO₄<br>Mol. Wt.: 419.51<br>TW-25 |

TABLE 3-continued
| Name | Compound |
|---|---|
| TW-26 | 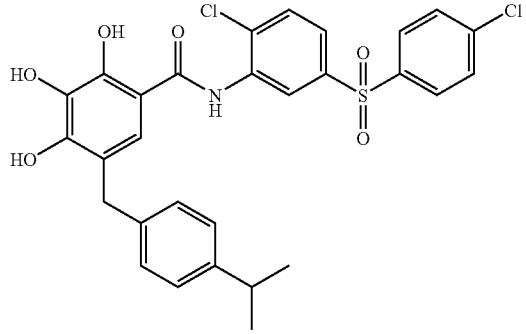<br>$C_{29}H_{25}Cl_2NO_6S$<br>Mol. Wt.: 586.48<br>TW-26 |
| TW-27 | 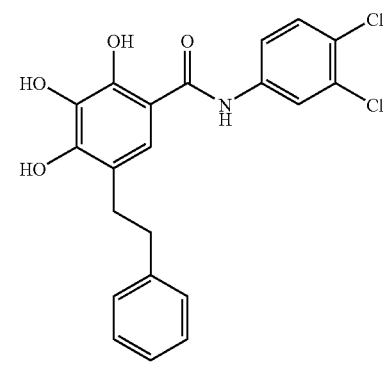<br>$C_{21}H_{17}Cl_2NO_4$<br>Mol. Wt.: 418.27<br>TW-27 |
| TW-28 | 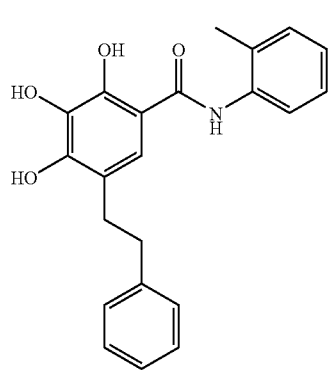<br>$C_{22}H_{21}NO_4$<br>Mol. Wt.: 363.41<br>TW-28 |

TABLE 3-continued
| Name | Compound |
|---|---|
| TW-29 | 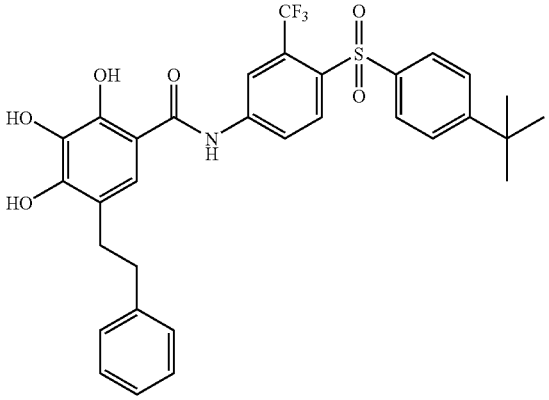<br>$C_{32}H_{30}F_3NO_6S$<br>Mol. Wt.: 613.64<br>TW-29 |
| TW-30 | 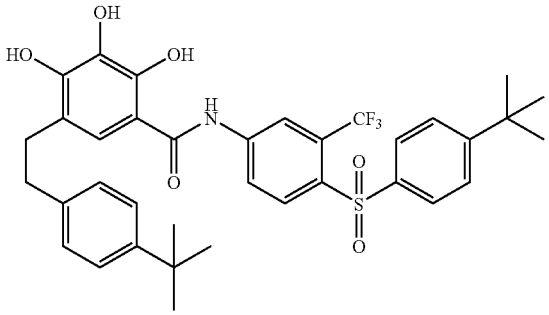 [SMILES: CC(C)(C)c1ccc(CCc2cc(C(=O)Nc3ccc(S(=O)(=O)c4ccc(C(C)(C)C)cc4)c(C(F)(F)F)c3)c(O)c(O)c2O)cc1] |
| TW-31 | 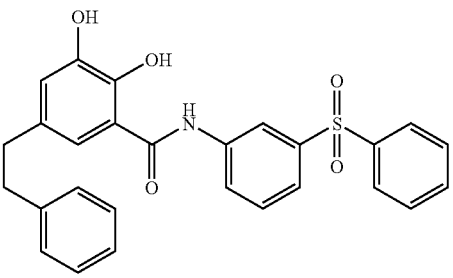 [SMILES: O=C(Nc1cccc(S(=O)(=O)c2ccccc2)c1)c1cc(CCc2ccccc2)cc(O)c1O] |
| TW-32 | 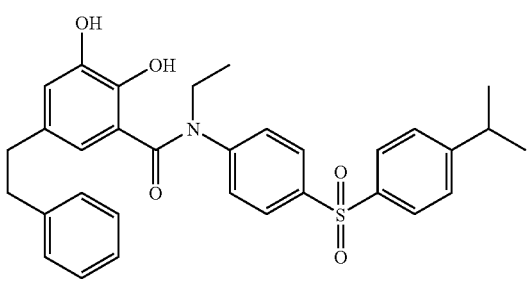 [SMILES: CCN(C(=O)c1cc(CCc2ccccc2)cc(O)c1O)c1ccc(S(=O)(=O)c2ccc(C(C)C)cc2)cc1] |

TABLE 3-continued

| Name | Compound |
|---|---|
| TW-33 | |
| TW-34 | |
| TW-35 | |
| TW-36 | |
| TW-37A | |

TABLE 3-continued

| Name | Compound |
|---|---|
| TW-37 | |
| TW-38 | |
| TW-39 | |
| TW-40 | |

TABLE 3-continued

| Name | Compound |
|---|---|
| TW-41 | (structure) |
| TW-42 | (structure) |
| TW-43 | (structure) |
| TW-44 | (structure) |

TABLE 3-continued

| Name | Compound |
|---|---|
| TW-45 | (structure) |
| TW-46 | (structure) |
| TW-47 | (structure) |
| TW-48 | (structure) |
| TW-49 | (structure) |

TABLE 3-continued

| Name | Compound |
|---|---|
| TW-50 | |
| TW-51 | |
| TW-52 | |
| TW-53 | |
| TW-54 | |

TABLE 3-continued

| Name | Compound |
|---|---|
| TW-55 | 2,3,4-trihydroxy-5-(2-isopropylbenzyl)-N-methylbenzamide |
| TW-56 | 5-benzyl-2,3,4-trihydroxy-N-(4-(phenylsulfonyl)phenyl)benzamide |
| TW-57 | 5-(4-tert-butylphenethyl)-N-(4-((2-tert-butylphenyl)sulfonyl)phenyl)-2,3,4-trihydroxybenzamide |
| TW-58 | N-(4-((2-tert-butylphenyl)sulfonyl)-3-methylphenyl)-2,3,4-trihydroxy-5-(2-isopropylbenzyl)benzamide |
| TW-59 | N-(4-((2-tert-butylphenyl)sulfonyl)-3-chlorophenyl)-2,3,4-trihydroxy-5-(2-isopropylbenzyl)benzamide |

TABLE 3-continued
| Name | Compound |
|---|---|
| TW-60 | 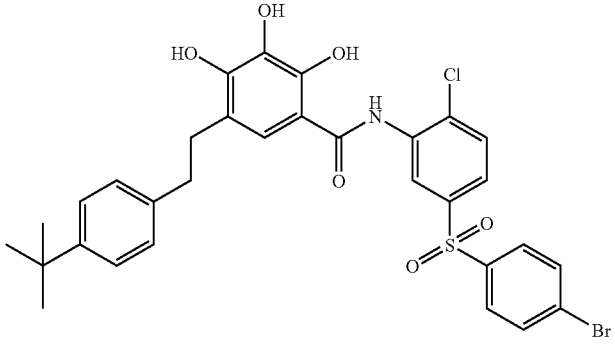 [SMILES: CC(C)(C)c1ccc(CCc2cc(C(=O)Nc3cc(S(=O)(=O)c4ccc(Br)cc4)ccc3Cl)c(O)c(O)c2O)cc1] |
| TW-61 | 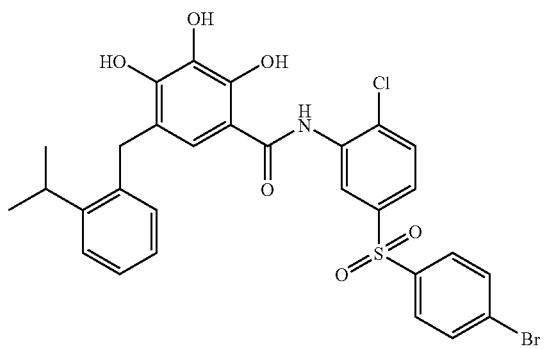 [SMILES: CC(C)c1ccccc1Cc1cc(C(=O)Nc2cc(S(=O)(=O)c3ccc(Br)cc3)ccc2Cl)c(O)c(O)c1O] |
| TW-62 | 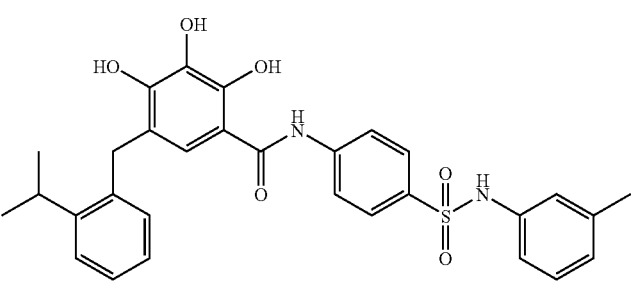 [SMILES: Cc1cccc(NS(=O)(=O)c2ccc(NC(=O)c3cc(Cc4ccccc4C(C)C)c(O)c(O)c3O)cc2)c1] |
| TW-63 | 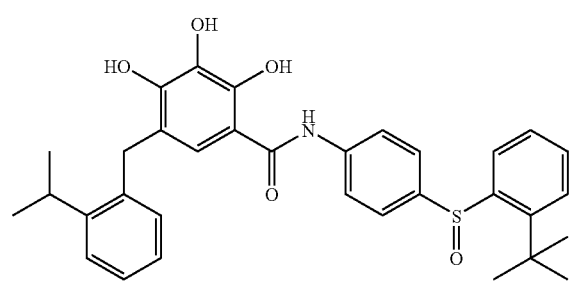 [SMILES: CC(C)c1ccccc1Cc1cc(C(=O)Nc2ccc(S(=O)c3ccccc3C(C)(C)C)cc2)c(O)c(O)c1O] |
| TW-64 | 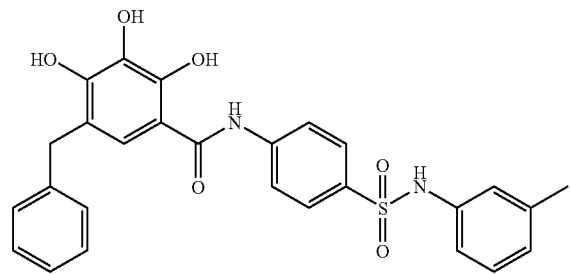 [SMILES: Cc1cccc(NS(=O)(=O)c2ccc(NC(=O)c3cc(Cc4ccccc4)c(O)c(O)c3O)cc2)c1] |

TABLE 3-continued
| Name | Compound |
|---|---|
| TW-65 | 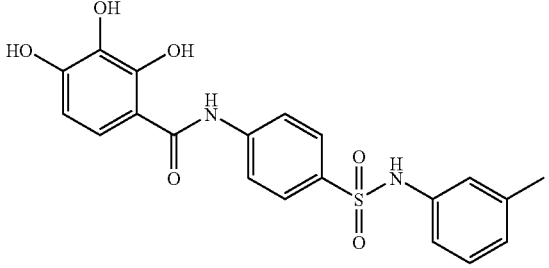 [SMILES: Cc1cccc(NS(=O)(=O)c2ccc(NC(=O)c3ccc(O)c(O)c3O)cc2)c1] |
| TW-66 | 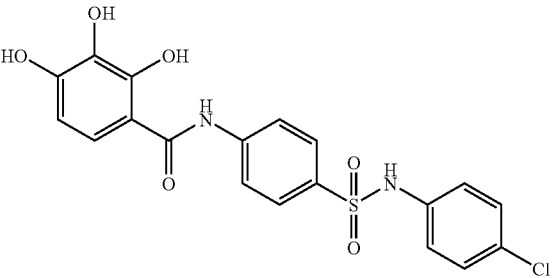 [SMILES: O=C(Nc1ccc(S(=O)(=O)Nc2ccc(Cl)cc2)cc1)c1ccc(O)c(O)c1O] |
| TW-68 | 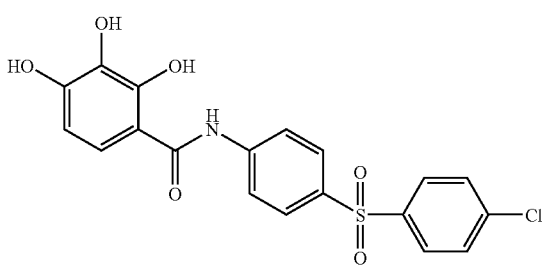 [SMILES: O=C(Nc1ccc(S(=O)(=O)c2ccc(Cl)cc2)cc1)c1ccc(O)c(O)c1O] |
| TW-69 | 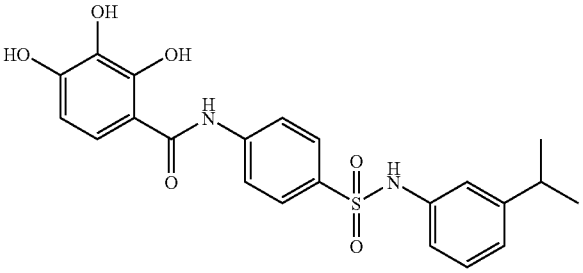 [SMILES: CC(C)c1cccc(NS(=O)(=O)c2ccc(NC(=O)c3ccc(O)c(O)c3O)cc2)c1] |
| TW-70 | 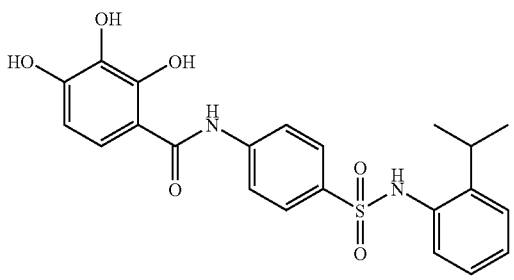 [SMILES: CC(C)c1ccccc1NS(=O)(=O)c1ccc(NC(=O)c2ccc(O)c(O)c2O)cc1] |

| Name | Compound |
|---|---|
| TW-71 | |
| TW-72 | |
| TW-73 | |
| TW-74 | |
| TW-75 | |

TABLE 3-continued

| Name | Compound |
|---|---|
| TW-76 | |
| TW-78 | |
| TW-79 | |
| TW-80 | |
| TW-81 | |

TABLE 3-continued

| Name | Compound |
|---|---|
| TW-82 | |
| TW-83 | |
| TW-85 | |
| TW-86 | |
| TW-87 | |

TABLE 3-continued

| Name | Compound |
|---|---|
| TW-88 | (structure) |
| TW-89 | (structure) |
| TW-90 | (structure) |
| TW-91 | (structure) |
| TW-92 | (structure) |

TABLE 3-continued

| Name | Compound |
|---|---|
| TW-93 | |
| TW-94 | |
| TW-95A | |
| TW-95 | |

TABLE 3-continued
| Name | Compound |
|---|---|
| TW-96A | 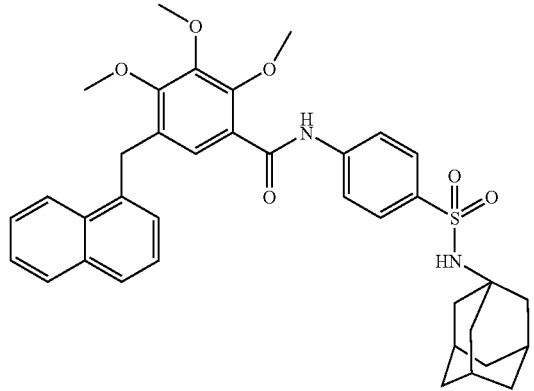 [SMILES: COc1c(Cc2cccc3ccccc23)cc(C(=O)Nc2ccc(S(=O)(=O)NC34CC5CC(CC(C5)C3)C4)cc2)c(OC)c1OC] |
| TW-97 | 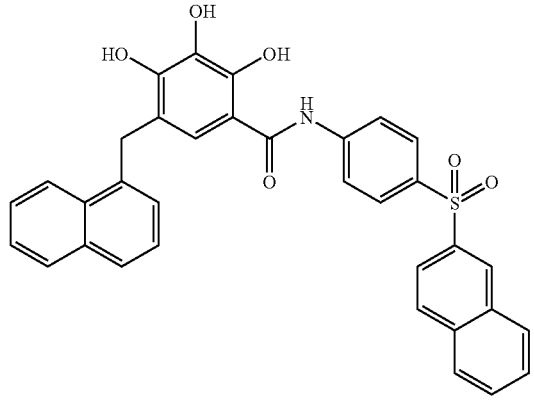 [SMILES: O=C(Nc1ccc(S(=O)(=O)c2ccc3ccccc3c2)cc1)c1cc(Cc2cccc3ccccc23)c(O)c(O)c1O] |
| TW-98A | 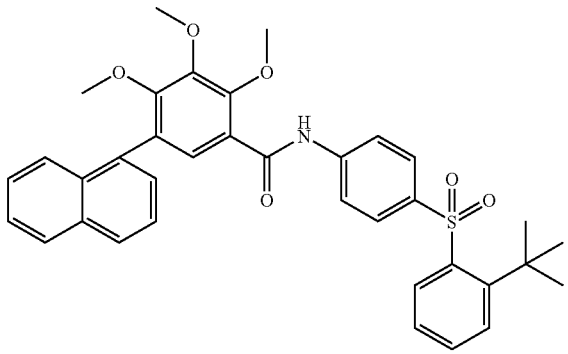 [SMILES: COc1c(C(=O)Nc2ccc(S(=O)(=O)c3ccccc3C(C)(C)C)cc2)cc(-c2cccc3ccccc23)c(OC)c1OC] |
| TW-98 | 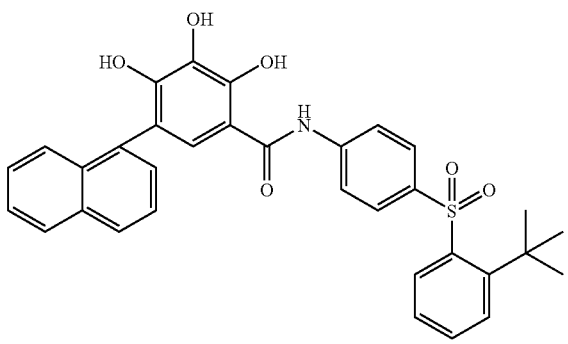 [SMILES: CC(C)(C)c1ccccc1S(=O)(=O)c1ccc(NC(=O)c2cc(-c3cccc4ccccc34)c(O)c(O)c2O)cc1] |

TABLE 3-continued
| Name | Compound |
|---|---|
| TW-99 | 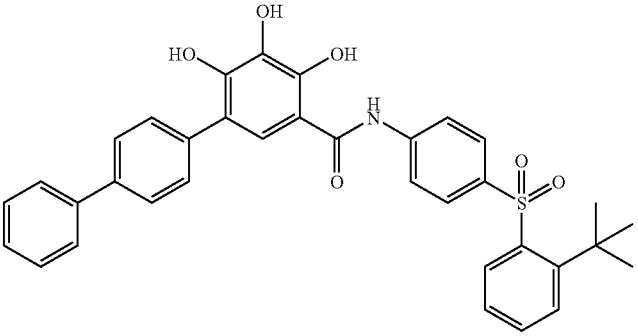 [SMILES: CC(C)(C)c1ccccc1S(=O)(=O)c1ccc(NC(=O)c2cc(-c3ccc(-c4ccccc4)cc3)c(O)c(O)c2O)cc1] |
| TW-100 | 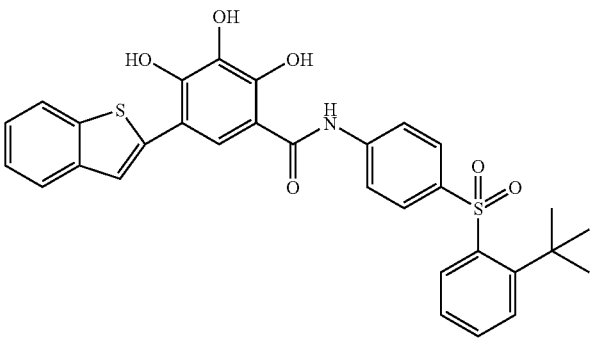 [SMILES: CC(C)(C)c1ccccc1S(=O)(=O)c1ccc(NC(=O)c2cc(-c3cc4ccccc4s3)c(O)c(O)c2O)cc1] |
| TW-101 | 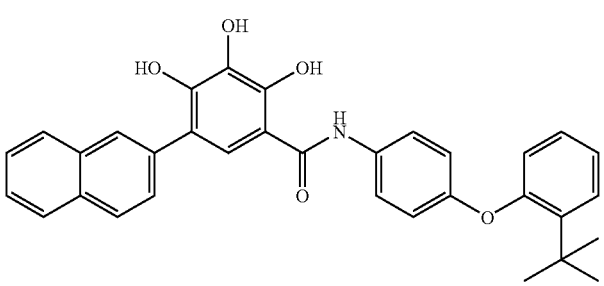 [SMILES: CC(C)(C)c1ccccc1Oc1ccc(NC(=O)c2cc(-c3ccc4ccccc4c3)c(O)c(O)c2O)cc1] |
| TW-103 | 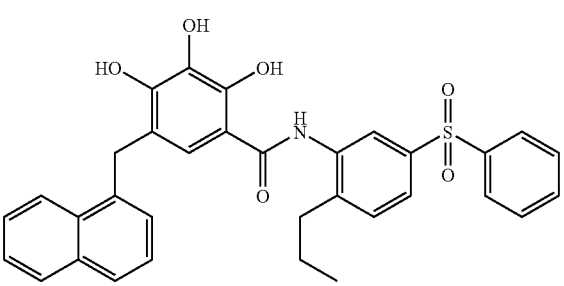 [SMILES: CCCc1ccc(S(=O)(=O)c2ccccc2)cc1NC(=O)c1cc(Cc2cccc3ccccc23)c(O)c(O)c1O] |
| TW-104 | 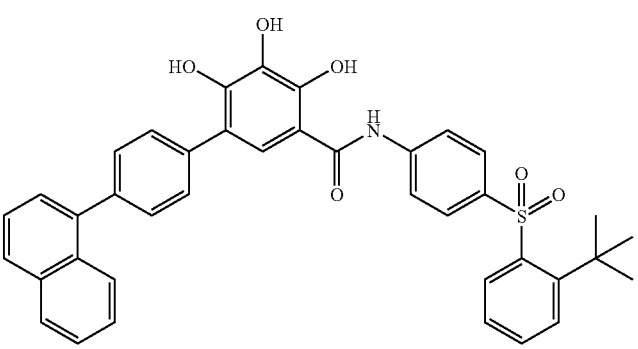 [SMILES: CC(C)(C)c1ccccc1S(=O)(=O)c1ccc(NC(=O)c2cc(-c3ccc(-c4cccc5ccccc45)cc3)c(O)c(O)c2O)cc1] |

TABLE 3-continued
| Name | Compound |
|---|---|
| TW-105 | 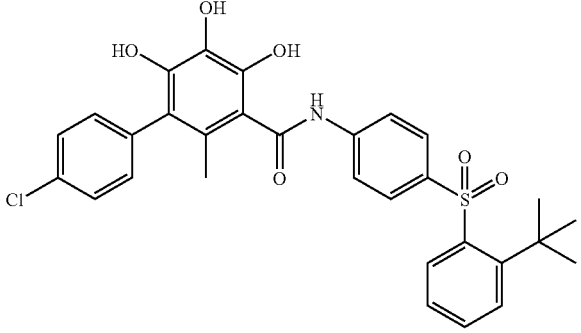 [SMILES: Cc1c(C(=O)Nc2ccc(S(=O)(=O)c3ccccc3C(C)(C)C)cc2)c(O)c(O)c(O)c1-c1ccc(Cl)cc1] |
| TW-106 | 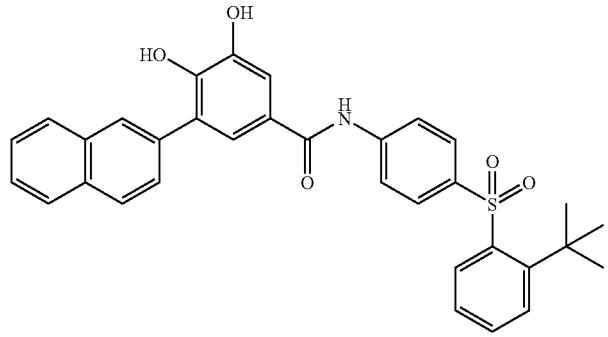 [SMILES: CC(C)(C)c1ccccc1S(=O)(=O)c1ccc(NC(=O)c2cc(O)c(O)c(-c3ccc4ccccc4c3)c2)cc1] |
| TW-107 | 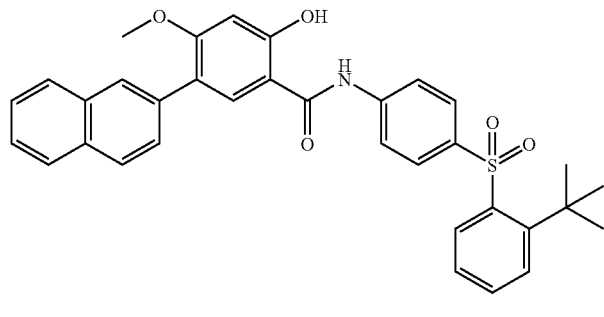 [SMILES: COc1cc(O)c(C(=O)Nc2ccc(S(=O)(=O)c3ccccc3C(C)(C)C)cc2)cc1-c1ccc2ccccc2c1] |
| TW-108 | 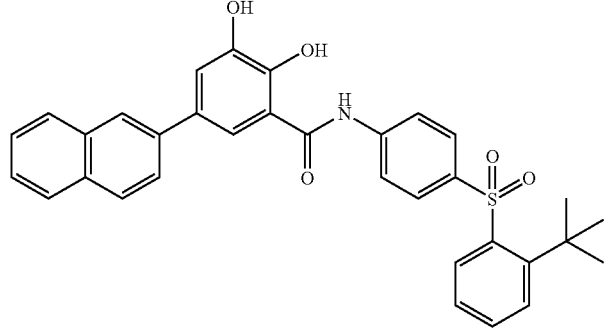 [SMILES: CC(C)(C)c1ccccc1S(=O)(=O)c1ccc(NC(=O)c2cc(-c3ccc4ccccc4c3)cc(O)c2O)cc1] |

TABLE 3-continued

| Name | Compound |
|---|---|
| TW-109 | |
| TW-110 | |
| TW-115 | |
| TW-116 | |
| TW-118 | |

TABLE 3-continued

| Name | Compound |
|---|---|
| TW-119 | |
| TW-120 | |
| TW-121 | |
| TW-122 | |
| TW-123 | |

TABLE 3-continued

| Name | Compound |
|---|---|
| TW-124 | (structure: 4,5,6-trihydroxy-2-bromo-7-phenyl-indanone) |
| TW-125 | (structure: 3-(benzothiophen-2-yl)-2,4,5-trihydroxy-N-(dibenzothiophene 5,5-dioxide-2-yl)benzamide) |
| TW-126 | (structure: 3-(2-isopropylbenzyl)-2,4,5-trihydroxy-N-(dibenzothiophene 5,5-dioxide-2-yl)benzamide) |
| TW-127 | (structure: 3-(2-isopropylbenzyl)-2,4,5-trihydroxy-N-(4-((1-methoxy-1-oxo-3-phenylpropan-2-yl)sulfamoyl)phenyl)benzamide) |
| TW-128 | (structure: 2-(biphenyl-4-yl)-4,5,6-trihydroxy-7-phenyl-indanone) |

TABLE 3-continued

| Name | Compound |
|---|---|
| TW-129 | |
| TW-130 | |
| TW-131 | |
| TW-132 | |
| TW-133 | |
| TW-134 | |

TABLE 3-continued
| Name | Compound |
|---|---|
| TW-136 | 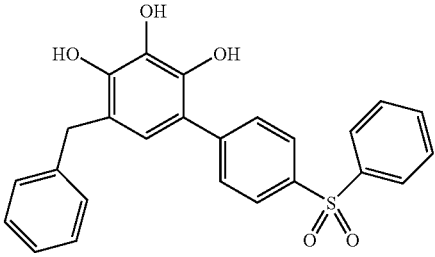 [SMILES: O=S(=O)(c1ccccc1)c1ccc(-c2cc(Cc3ccccc3)c(O)c(O)c2O)cc1] |
| TW-137 | 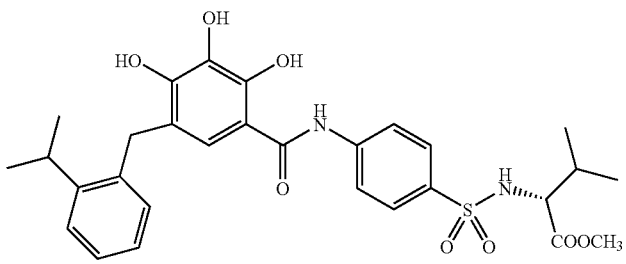 [SMILES: COC(=O)[C@H](NS(=O)(=O)c1ccc(NC(=O)c2cc(Cc3ccccc3C(C)C)c(O)c(O)c2O)cc1)C(C)C] |
| TW-138 | 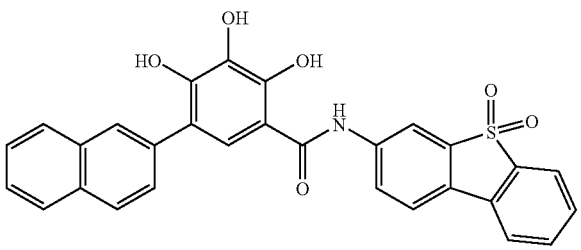 [SMILES: O=C(Nc1ccc2c(c1)S(=O)(=O)c1ccccc1-2)c1cc(-c2ccc3ccccc3c2)c(O)c(O)c1O] |
| TW-139 | 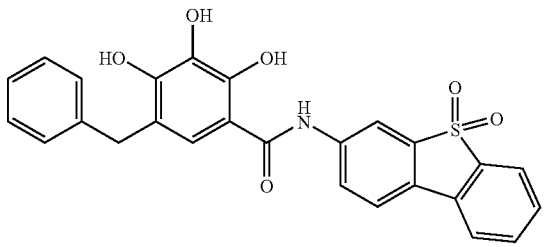 [SMILES: O=C(Nc1ccc2c(c1)S(=O)(=O)c1ccccc1-2)c1cc(Cc2ccccc2)c(O)c(O)c1O] |
| TW-140 | 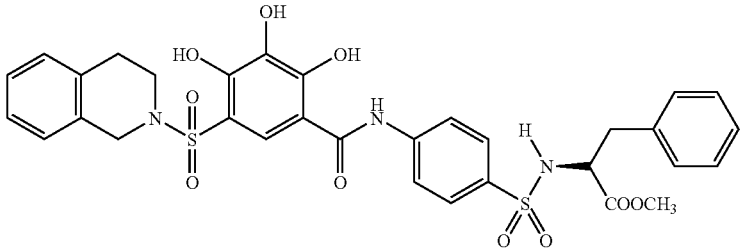 |
| TW-141 | 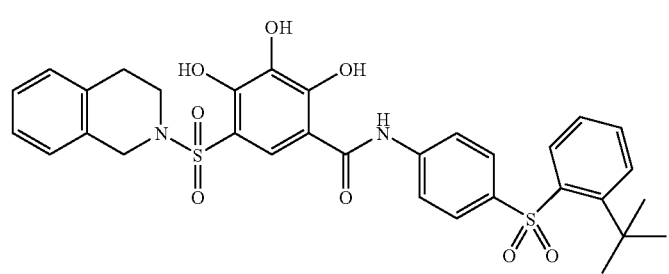 [SMILES: CC(C)(C)c1ccccc1S(=O)(=O)c1ccc(NC(=O)c2cc(S(=O)(=O)N3CCc4ccccc4C3)c(O)c(O)c2O)cc1] |

| Name | Compound |
|---|---|
| TW-142 | (chemical structure) |
| TW-143 | (chemical structure) |
| TW-144 | (chemical structure) |
| TW-145 | (chemical structure) |
| TW-146 | (chemical structure) |

TABLE 3-continued

| Name | Compound |
|---|---|
| TW-147 | |
| TW-148 | |
| TW-149 | |
| TW-150 | |
| TW-151 | |

TABLE 3-continued

| Name | Compound |
|---|---|
| TW-152 | |
| TW-153 | |
| TW-154 | |
| TW-159 | |
| TW-160 | |
| TW-161 | |

TABLE 3-continued
| Name | Compound |
|---|---|
| TW-162 | 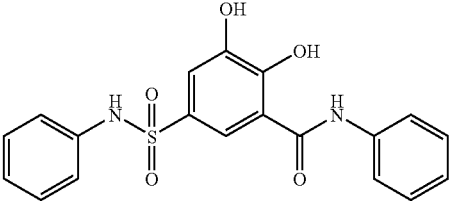 [SMILES: O=C(Nc1ccccc1)c1cc(S(=O)(=O)Nc2ccccc2)cc(O)c1O] |
| TW-163 | 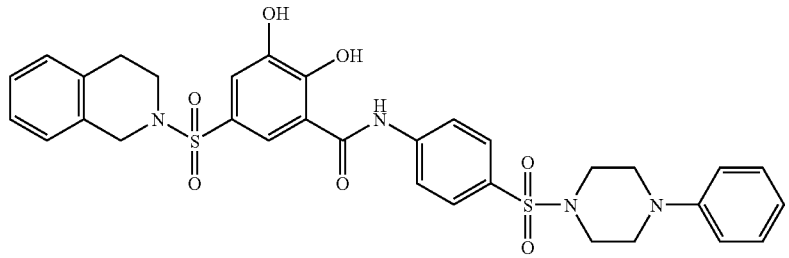 [SMILES: O=C(Nc1ccc(S(=O)(=O)N2CCN(c3ccccc3)CC2)cc1)c1cc(S(=O)(=O)N2CCc3ccccc3C2)cc(O)c1O] |
| TW-164 | 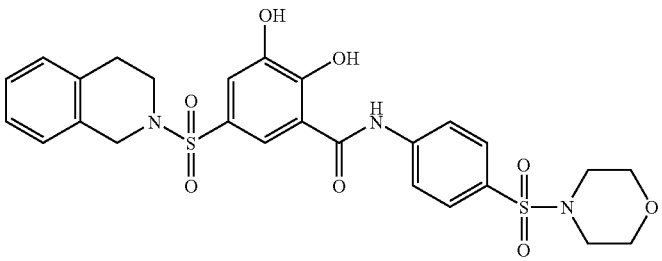 [SMILES: O=C(Nc1ccc(S(=O)(=O)N2CCOCC2)cc1)c1cc(S(=O)(=O)N2CCc3ccccc3C2)cc(O)c1O] |
| TW-165 | 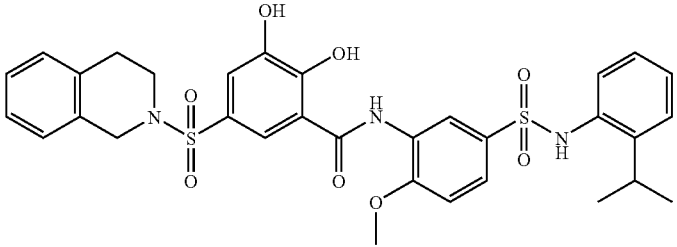 [SMILES: COc1ccc(S(=O)(=O)Nc2ccccc2C(C)C)cc1NC(=O)c1cc(S(=O)(=O)N2CCc3ccccc3C2)cc(O)c1O] |
| TW-166 | 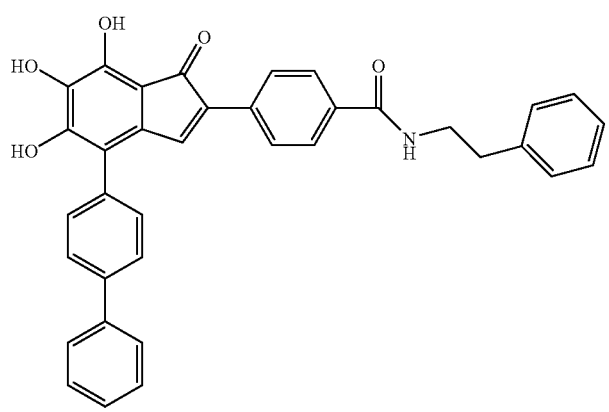 [SMILES: O=C(NCCc1ccccc1)c1ccc(C2=Cc3c(c(O)c(O)c(O)c3-c3ccc(-c4ccccc4)cc3)C2=O)cc1] |

| Name | Compound |
|---|---|
| TW-167 | *(structure)* |
| TW-168 | *(structure)* |
| TW-169 | *(structure)* |
| TW-170 | *(structure)* |
| TW-172 | *(structure)* |

TABLE 3-continued

| Name | Compound |
|---|---|
| TW-173 | |
| TW-174 | |
| TW-175 | |
| TW-176 | |
| TW-177 | |

TABLE 3-continued

| Name | Compound |
|---|---|
| TW-178 | (structure) |
| TW-179 | (structure) |
| TW-180 | (structure) |

TABLE 4

| Name | Compound |
|---|---|
| TW-183 | (structure) |
| TW-184 | (structure) |

TABLE 4-continued

| Name | Compound |
|---|---|
| TW-189 | |
| TW-190 | |
| TW-194 | |
| TW-195 | |
| TW-196 | |
| TW-198 | |

TABLE 4-continued
| Name | Compound |
|---|---|
| TW-199 | 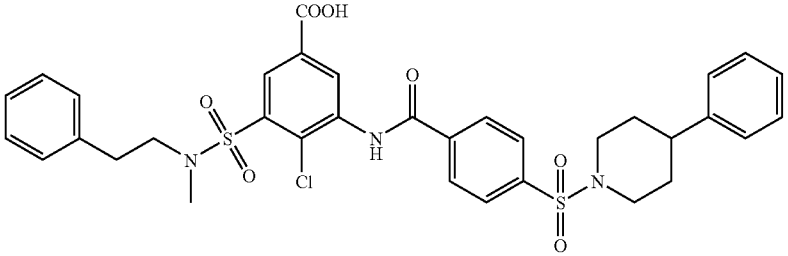 [SMILES: CN(CCc1ccccc1)S(=O)(=O)c1cc(C(=O)O)cc(NC(=O)c2ccc(S(=O)(=O)N3CCC(c4ccccc4)CC3)cc2)c1Cl] |
| TW-200 | 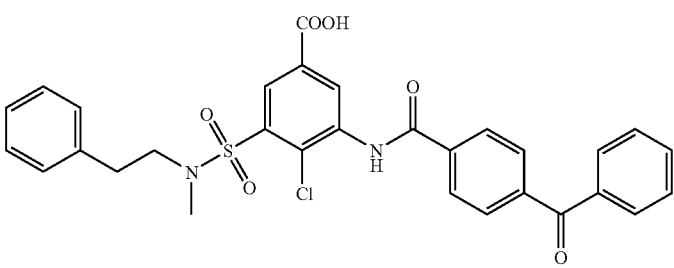 [SMILES: CN(CCc1ccccc1)S(=O)(=O)c1cc(C(=O)O)cc(NC(=O)c2ccc(C(=O)c3ccccc3)cc2)c1Cl] |
| TW-201 | 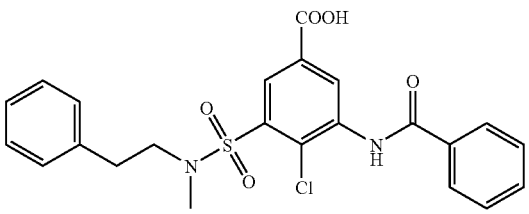 [SMILES: CN(CCc1ccccc1)S(=O)(=O)c1cc(C(=O)O)cc(NC(=O)c2ccccc2)c1Cl] |
| TW-202 | 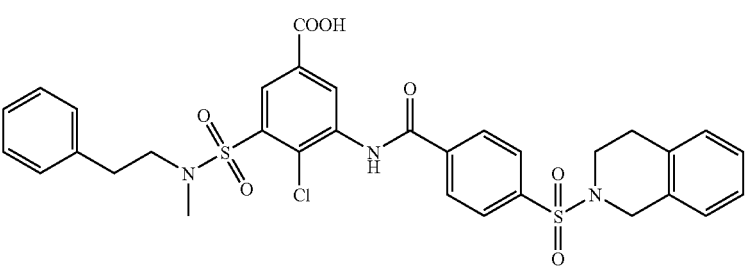 [SMILES: CN(CCc1ccccc1)S(=O)(=O)c1cc(C(=O)O)cc(NC(=O)c2ccc(S(=O)(=O)N3CCc4ccccc4C3)cc2)c1Cl] |
| TW-203 | 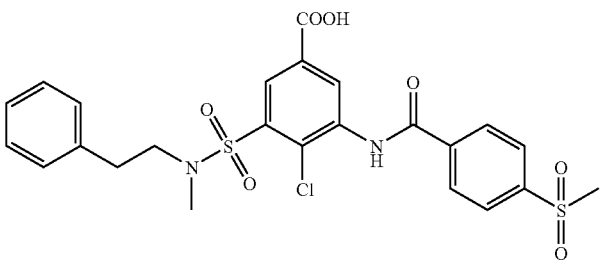 [SMILES: CN(CCc1ccccc1)S(=O)(=O)c1cc(C(=O)O)cc(NC(=O)c2ccc(S(C)(=O)=O)cc2)c1Cl] |
| TW-204 | 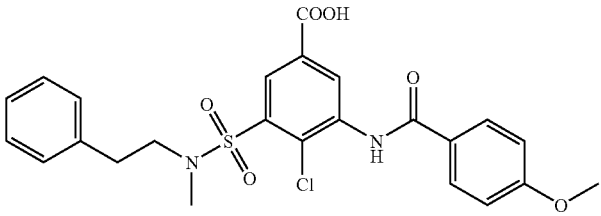 [SMILES: COc1ccc(C(=O)Nc2cc(C(=O)O)cc(S(=O)(=O)N(C)CCc3ccccc3)c2Cl)cc1] |

TABLE 4-continued

| Name | Compound |
|---|---|
| TW-205 | |
| TM-1230 | |
| TM-1231 | |
| TM-1232 | |
| TM-1233 | |
| TM-1234 | |

TABLE 4-continued

| Name | Compound |
|---|---|
| TM-1235 | |
| TM-1236 | |
| TM-1237 | |
| TM-1238 | |
| TM-1239 | |
| TM-1240 | |

TABLE 4-continued

| Name | Compound |
|---|---|
| TM-1241 | |
| TM-1242 | |
| TM-1243 | |
| TM-1244 | |
| TM-1245 | |

TABLE 4-continued

| Name | Compound |
|---|---|
| TM-1246 | (structure) |
| TM-1247 | (structure) |
| TM-1248 | (structure) |
| TM-1249 | (structure) |
| TM-1250 | (structure) |

TABLE 4-continued

| Name | Compound |
|---|---|
| TM-1251 | (structure) |
| TM-1252 | (structure) |
| TM-1253 | (structure) |
| TM-1254 | (structure) |
| TM-1255 | (structure) |

TABLE 4-continued
| Name | Compound |
|---|---|
| TM-1256 | 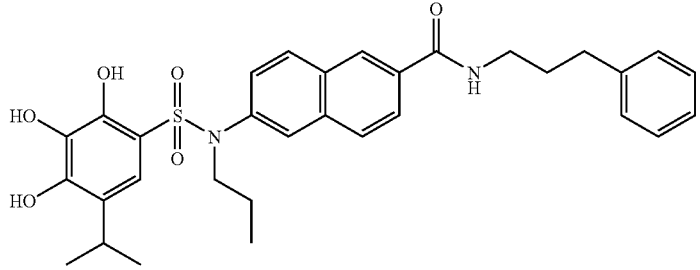 |
| TM-1257 | 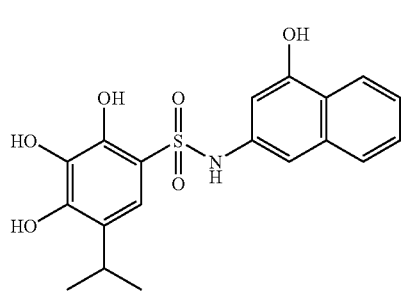 [SMILES: CC(C)c1cc(S(=O)(=O)Nc2cc(O)c3ccccc3c2)c(O)c(O)c1O] |
| TM-1258 | 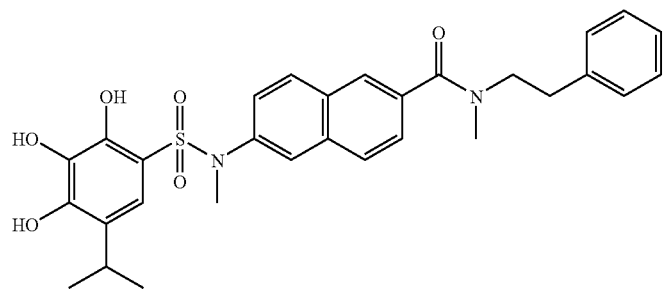 [SMILES: CC(C)c1cc(S(=O)(=O)N(C)c2ccc3cc(C(=O)N(C)CCc4ccccc4)ccc3c2)c(O)c(O)c1O] |
| TM-1259 | 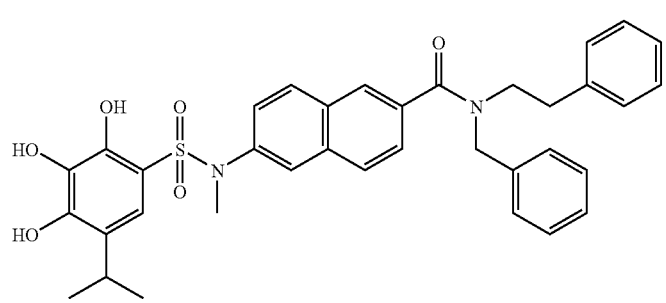 [SMILES: CC(C)c1cc(S(=O)(=O)N(C)c2ccc3cc(C(=O)N(CCc4ccccc4)Cc4ccccc4)ccc3c2)c(O)c(O)c1O] |
| TM-1260 | 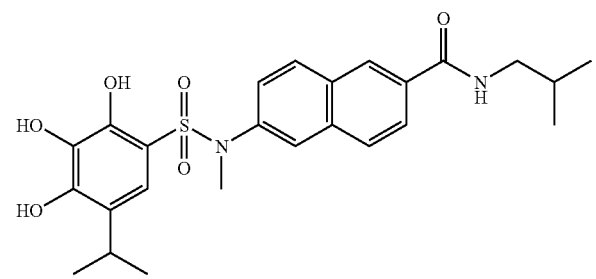 [SMILES: CC(C)CNC(=O)c1ccc2cc(N(C)S(=O)(=O)c3cc(C(C)C)c(O)c(O)c3O)ccc2c1] |

TABLE 4-continued
| Name | Compound |
|---|---|
| TM-1261 | 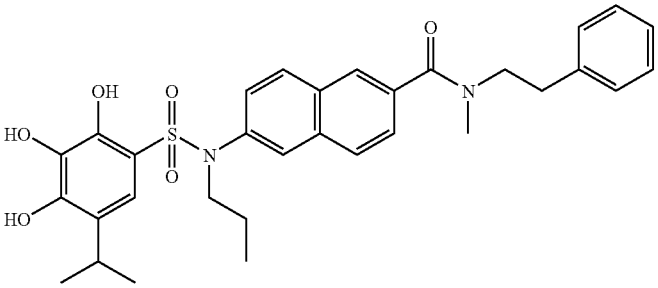 [SMILES: CCCN(c1ccc2cc(C(=O)N(C)CCc3ccccc3)ccc2c1)S(=O)(=O)c1cc(C(C)C)c(O)c(O)c1O] |
| TM-1262 | 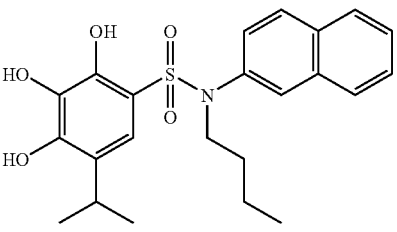 [SMILES: CCCCN(c1ccc2ccccc2c1)S(=O)(=O)c1cc(C(C)C)c(O)c(O)c1O] |
| TM-1263 | 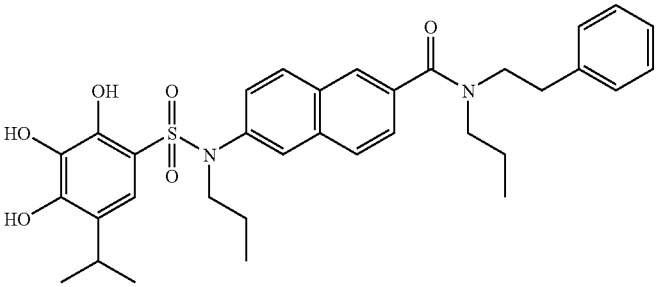 [SMILES: CCCN(CCc1ccccc1)C(=O)c1ccc2cc(N(CCC)S(=O)(=O)c3cc(C(C)C)c(O)c(O)c3O)ccc2c1] |
| TM-1264 | 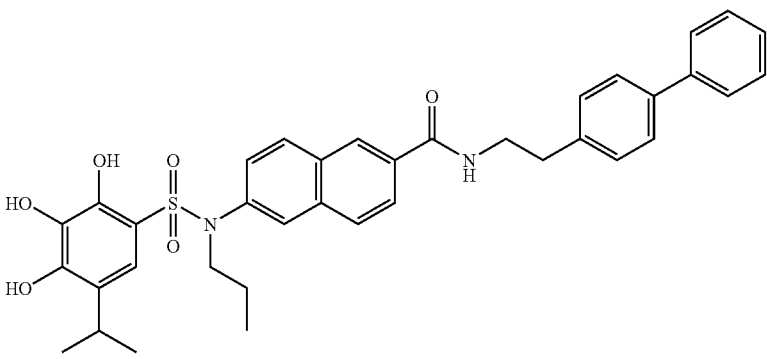 [SMILES: CCCN(c1ccc2cc(C(=O)NCCc3ccc(-c4ccccc4)cc3)ccc2c1)S(=O)(=O)c1cc(C(C)C)c(O)c(O)c1O] |
| TM-1265 | 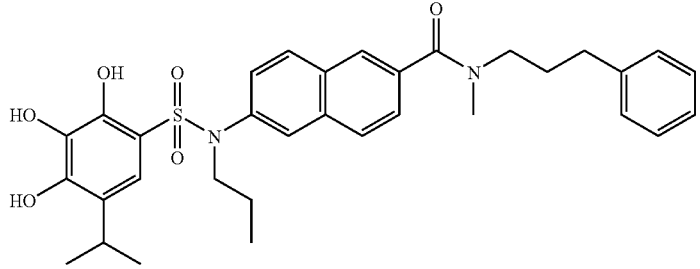 [SMILES: CCCN(c1ccc2cc(C(=O)N(C)CCCc3ccccc3)ccc2c1)S(=O)(=O)c1cc(C(C)C)c(O)c(O)c1O] |

TABLE 4-continued
| Name | Compound |
|---|---|
| TM-1266 | 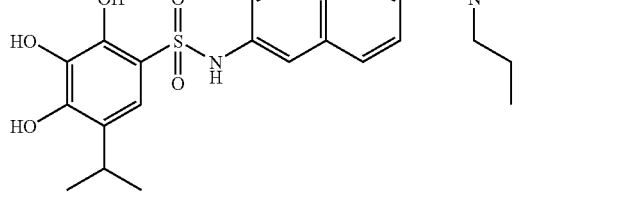 |
| TM-1267 | 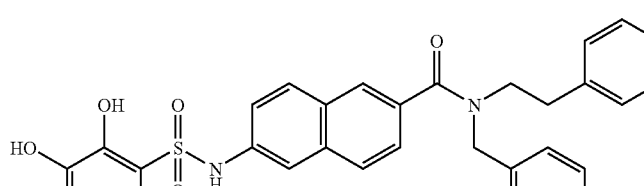 |
| TM-1269 | 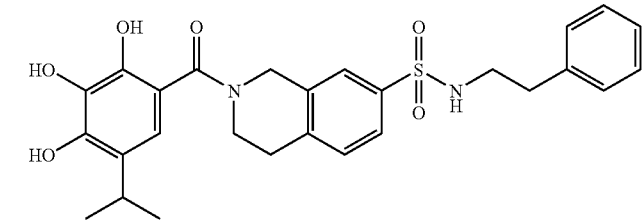 [SMILES: CC(C)c1cc(C(=O)N2CCc3ccc(S(=O)(=O)NCCc4ccccc4)cc3C2)c(O)c(O)c1O] |
| TM-1271 | 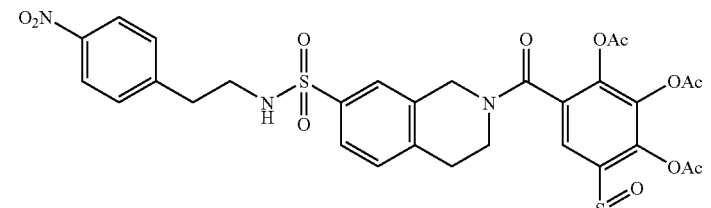 |
| TM-1276 | 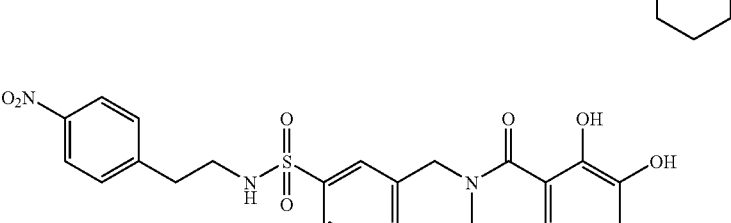 |

TABLE 4-continued

| Name | Compound |
|---|---|
| TM-1277 | (structure) |
| TM-1278 | (structure) |
| TM-1282 | (structure) |

TM-103

¹H NMR (CDCl₃, 300 MHz) δ 6.49 (s, 1H), 6.02 (b, 1H), 5.50 (b, 1H), 5.41 (b, 1H), 3.07 (m, 1H), 2.48 (m, 2H), 1.53 (m, 2H), 1.27 (m, 6H), 1.18 (d, 6H), 0.87 (m, 3H); ¹³C NMR (CDCl₃, 75 MHz) δ 139.79, 139.58, 131.67, 127.34, 121.45, 117.75, 31.76, 30.20, 29.75, 29.23, 26.85, 22.85, 22.67, 14.11.

TM-104

¹H NMR (CDCl₃, 300 MHz) δ 12.81 (s, OH), 7.17 (s, 1H), 6.07 (s, OH), 5.66 (s, OH), 3.22 (m, 1H), 2.92 (t, 2H), 1.74 (m, 2H), 1.38 (m, 4H), 1.25 (d, 6H), 0.92 (t, 3H); ¹³C NMR (CDCl₃, 75 MHz) δ 206.14, 148.70, 130.64, 126.64, 118.72, 112.86, 37.87, 31.52, 27.04, 24.56, 22.49, 13.95.

TM-108

¹H NMR (CDCl₃, 300 MHz) δ 12.59 (s, OH), 7.81-7.72 (m, 4H), 7.45-7.35 (m, 4H), 6.22 (s, OH), 5.86 (s, OH), 4.38 (s, 2H), 3.19 (m, 1H), 1.22 (d, 6H); ¹³C NMR (CDCl₃, 75 MHz) δ 203.27, 149.51, 148.66, 133.95, 132.85, 132.39, 131.13, 128.80, 128.64, 128.11, 128.04, 127.87, 127.37, 126.65, 126.28, 119.83, 112.92, 45.53, 27.33, 22.91.

TM-109

¹H NMR (CDCl₃, 300 MHz) δ 6.49 (s, 1H), 5.50 (b, OH), 5.16 (b, OH), 5.04 (b, OH), 3.10 (m, 1H), 2.52 (t, 2H), 1.56 (m, 2H), 1.23 (m, 30H), 0.88 (m, 3H); ¹³C NMR (CDCl₃, 75 MHz) δ 140.01, 139.84, 131.96, 127.13, 121.15, 117.75, 32.34, 32.01, 30.70, 30.11, 29.96, 29.78, 27.34, 23.25, 23.11, 23.07, 21.47.

TM-110

¹H NMR (CDCl₃, 300 MHz) δ 12.84 (s, OH), 7.17 (s, 1H), 6.13 (s, OH), 5.76 (s, OH), 3.20 (m, 1H), 2.92 (t, 2H), 1.72 (m, 2H), 1.35-1.24 (m, 28H), 0.86 (t, 3H); ¹³C NMR (CDCl₃, 75 MHz) δ 206.18, 148.72, 147.73, 130.62, 126.65, 118.74, 112.85, 37.92, 31.94, 29.68, 29.64, 29.50, 29.46, 29.38, 27.05, 24.92, 22.71, 22.49, 14.14.

TM-121

¹H NMR (CDCl₃, 300 MHz) δ 7.30-7.19 (m, 5H), 6.47 (s, 1H), 5.31 (b, OH), 5.07 (b, OH), 4.79 (b, OH), 3.90 (s, 2H), 2.50 (t, 2H), 1.55 (m, 2H), 1.26 (m, 16H), 0.86 (m, 3H); ¹³C NMR (CDCl₃, 75 MHz) δ 140.61, 140.16, 139.91, 132.09, 128.72, 128.46, 126.39, 121.90, 121.26, 119.01, 36.21, 31.94, 30.13, 29.69, 29.66, 29.56, 29.52, 29.49, 29.37, 22.71, 14.14.

TM-122

¹H NMR (CDCl₃, 300 MHz) δ 12.87 (s, OH), 7.30-7.23 (m, 5H), 7.08 (s, 1H), 6.23 (b, OH), 5.91 (b, OH), 3.95 (s, 2H), 2.80 (m, 2H), 1.66 (m, 2H), 1.26 (m, 14H), 0.87 (m, 3H); $^{13}$C NMR (CDCl$_3$, 75 MHz) δ 206.22, 149.32, 148.16, 140.24, 130.93, 128.69, 128.43, 126.15, 122.93, 119.41, 112.92, 38.00, 35.26, 31.92, 31.61, 29.59, 29.50, 29.43, 29.35, 25.01, 22.70, 14.14.

TM-123

$^1$H NMR (CDCl$_3$, 300 MHz) δ 7.20 (m, 5H), 6.59 (s, 1H), 5.22 (b, 2OH), 4.69 (b, OH), 3.99 (t, 2H), 2.55 (t, 2H), 1.96 (m, 2H), 1.58 (m, 2H), 1.25 (m, 32H), 0.88 (m, 6H); $^{13}$C NMR (CDCl$_3$, 75 MHz) δ 144.74, 140.30, 139.55, 132.16, 128.69, 127.84, 126.39, 123.24, 120.95, 119.06, 44.58, 34.68, 31.95, 31.93, 30.15, 29.95, 29.73, 29.69, 29.63, 29.56, 29.48, 29.39, 29.36, 27.90, 22.84, 22.71, 14.13.

TM-125

$^1$H NMR (CDCl$_3$, 300 MHz) δ 7.36 (M, 2h), 7.28-7.17 (M, 5h), 7.06 (D, 2h), 6.59 (s 1H), 5.30 (b, OH), 5.12 (b, OH), 4.79 (b, OH), 3.98 (t, 1H), 3.87 (d, 2H), 1.93 (m, 2H), 1.20 (m, 16H), 0.88 (t, 3H); $^{13}$C NMR (CDCl$_3$, 75 MHz) δ 144.47, 140.65, 140.38, 139.72, 132.49, 131.46, 130.27, 128.75, 127.81, 126.51, 123.69, 119.91, 119.85, 118.93, 44.58, 35.34, 34.60, 31.91, 29.65, 29.62, 29.56, 29.35, 27.88, 22.69, 21.04, 14.14.

TM-126

$^1$H NMR (CDCl$_3$, 300 MHz) δ 12.57, 7.61 (d, 2H), 7.35 (d, 2H), 7.23 (m, 1H), 7.15 (m, 4H), 7.03 (s, 1H), 6.04 (b, OH), 5.62 (b, OH), 3.00 (m, 1H), 2.63 (m, 4H), 1.90 (m, 2H), 1.31 (6H); $^{13}$C NMR (CDCl$_3$, 75 MHz) δ 200.26, 153.10, 149.56, 148.24, 142.24, 135.70, 130.89, 129.37, 128.40, 128.25, 126.44, 126.08, 125.69, 120.07, 112.56, 35.38, 34.23, 31.16, 29.12, 23.78.

TM-127

$^1$H NMR (CDCl$_3$, 300 MHz) δ 12.54 (s, OH), 7.72 (m, 4H), 7.65-7.45 (m, 4H), 7.32-7.15 (m, 5H), 7.05 (s, 1H), 6.10 (b, OH), 5.69 (b, OH), 2.65 (4H), 1.91 (m, 2H), 1.66 (m, 2H), 1.50 (m, 2H), 1.27 (m, 10H), 0.89 (m, 3H).

TM-128

$^1$H NMR (CDCl$_3$, 300 MHz) δ 12.36 (s, OH), 7.64 (d, 2H), 7.52 (d, 2H), 7.27-7.23 (m, 2H), 7.19-7.13 (m, 3H), 6.90 (1H), 6.11 (b, OH), 5.65 (b, OH), 2.61 (m, 4H), 1.88 (m, 2H); $^{13}$C NMR (CDCl$_3$, 75 MHz) δ 199.22, 149.60, 148.72, 142.10, 136.81, 131.63, 130.96, 130.51, 128.37, 128.29, 126.47, 125.75, 120.51, 112.27, 35.40, 31.11, 29.11.

TM-129

$^1$H NMR (CDCl$_3$, 300 MHz) δ 6.37 (s, 1H), 5.30 (b, OH), 5.10 (b, OH), 4.95 (b, OH), 2.50 (t, 2H), 2.38 (d, 2H), 1.68 (m, 5H), 1.55 (m, 4H), 1.20 (m, 20H), 0.90 (m, 3H); $^{13}$C NMR (CDCl$_3$, 75 MHz) δ 139.90, 139.80, 131.61, 128.81, 128.71, 128.06, 127.85, 126.41, 122.15, 120.59, 119.06, 38.74, 37.55, 33.30, 31.94, 30.48, 30.15, 29.67, 29.56, 29.48, 29.37, 26.55, 26.32, 25.71, 22.71, 14.14, 14.05.

TM-130

$^1$H NMR (CDCl$_3$, 300 MHz) δ 7.31-7.15 (m, 5H), 6.26 (s, 1H), 5.06 (b, OH), 5.00 (b, OH), 4.79 (b, OH), 2.71 (t, 2H), 2.56 (t, 2H), 2.37 (t, 2H), 1.84 (m, 2H), 1.43 (m, 2H), 1.26 (m, 16H), 0.88 (m, 3H); $^{13}$C NMR (CDCl$_3$, 75 MHz) δ 142.51, 142.29, 140.99, 133.21, 129.38, 128.43, 128.32, 125.77, 119.57, 108.03, 35.94, 32.45, 31.94, 31.69, 31.54, 29.70, 29.67, 29.56, 29.38, 25.31, 22.71, 14.15.

TM-132

$^1$H NMR (CDCl$_3$, 300 MHz) δ 7.30-7.25 (m, 2H), 7.20-7.15 (m, 3H), 7.13-7.05 (m, 4H), 6.48 (s, 1H), 5.20 (b, OH), 4.97 (b, OH), 4.62 (b, OH), 3.88 (s, 2H), 2.67 (t, 2H), 2.58 (t, 2H), 2.43 (d, 2H), 1.91 (m, 2H), 1.82 (m, 1H), 0.88 (d, 6H).

TM-133

$^1$H NMR (CDCl$_3$, 300 MHz) δ 7.29-7.22 (m, 2H), 7.19-7.17 (m, 3H), 7.10-7.03 (m, 8H), 6.46 (s, 1H), 5.24 (b, OH), 4.99 (b, OH), 4.66 (b, OH), 3.88 (s, 2H), 3.85 (s, 2H), 2.63 (t, 2H), 2.56 (t, 2H), 2.29 (s, 3H), 1.90 (m, 2H); $^{13}$C NMR (CDCl$_3$, 75 MHz) δ 142.34, 139.88, 139.68, 137.99, 137.51, 135.54, 129.24, 129.13, 128.75, 128.48, 128.44, 128.30, 125.70, 121.81, 120.67, 119.01, 41.08, 35.90, 35.46, 31.50, 28.92, 21.00.

TM-140

$^1$H NMR (CDCl$_3$, 300 MHz) δ 12.56 (s, OH), 7.62 (m, 2H), 7.45 (m, 2H), 7.29-7.20 (m, 6H), 7.06 (m, 2H), 7.01 (m, 3H), 6.12 (b, OH), 5.90 (b, OH), 3.95 (s, 2H); $^{13}$C NMR (CDCl$_3$, 75 MHz) δ 198.97, 160.96, 155.61, 149.82, 148.20, 140.17, 132.16, 131.49, 131.10, 130.04, 128.70, 128.39, 126.48, 126.10, 124.54, 120.09, 119.28, 117.22, 35.12.

TM-142

$^1$H NMR (CDCl$_3$, 300 MHz) δ 7.54-7.45 (m, 4H), 7.38 (m, 1H), 7.29-7.15 (m, 9H), 6.49 (s, 1H), 5.22 (b, 3OH), 3.88 (s, 2H), 3.86 (s, 2H); $^{13}$C NMR (CDCl$_3$, 75 MHz) δ 140.81, 140.08, 139.31, 139.13, 132.41, 128.90, 128.70, 128.63, 128.49, 127.28, 127.08, 126.94, 126.31, 122.86, 119.69, 119.64, 36.94, 35.49.

TM-143

$^1$H NMR (CDCl$_3$, 300 MHz) δ 12.70 (s, OH), 7.22-7.20 (m, 2H), 7.16-7.12 (m, 3H), 6.94 (s, 1H), 6.75 (d, 1H), 6.06 (s, OH), 5.63 (s, OH), 5.09 (s, OH), 3.84 (s, 2H), 2.99 (m, 1H), 2.20 (s, 3H), 1.12 (d, 6H); $^{13}$C NMR (CDCl$_3$, 75 MHz) δ 197.42, 162.94, 157.62, 154.58, 151.95, 149.52, 146.35, 140.75, 133.76, 130.71, 130.55, 129.74, 128.71, 128.34, 126.34, 125.99, 120.52, 112.77, 36.75, 36.06, 24.09, 15.36.

TM-144

$^1$H NMR (CDCl$_3$, 300 MHz) δ 8.23 (d, 1H), 7.64 (dd, 1H), 7.28-7.14 (m, 5H), 7.01 (s, 1H), 6.96 (s, 1H), 6.84 (d, 1H), 6.26 (s, 1H), 5.52 (b, OH), 5.30 (b, OH), 4.96 (b, OH), 3.95 (s, 2H), 3.87 (s, 2H), 3.15 (m, 1H), 2.08 (s, 3H), 1.11 (d, 6H).

TM-145

$^1$H NMR (CDCl$_3$, 300 MHz) δ 7.93 (d, 1H), 7.34 (d, 1H), 7.26-7.23 (m, 2H), 7.17 (m, 3H), 7.01 (s, 1H), 6.98 (dd, 1H), 6.93 (s, 1H), 6.28 (s, 1H), 5.61 (b, OH), 5.36 (b, OH), 5.04 (b, OH), 3.95 (s, 2H), 3.88 (s, 2H), 3.15 (m, 1H), 2.06 (s, 3H), 1.11 (d, 6H).

TM-146

¹H NMR (CDCl₃, 300 MHz) δ 8.59 (d, 1H), 8.26 (dd, 1H), 7.26-7.22 (m, 2H), 7.20-7.14 (m, 3H), 6.98 (d, 1H), 6.73 (d, 1H), 6.24 (s, 1H), 5.90 (b, OH), 5.59 (b, OH), 5.36 (b, OH), 3.95 (d, 2H), 3.89 (d, 2H), 3.16 (m, 1H), 2.04 (s, 3H), 1.13 (d, 6H); ¹³C NMR (CDCl₃, 75 MHz) δ 161.31, 150.21, 147.72, 141.19, 141.12, 140.88, 140.29, 135.48, 133.50, 132.21, 129.01, 128.58, 128.50, 127.18, 126.29, 124.00 (q), 122.26, 119.66, 119.31, 119.19, 115.08, 35.92, 34.69, 31.62, 23.67, 15.40.

TM-147

¹H NMR (CDCl₃, 300 MHz) δ 8.43 (d, 1H), 8.38 (d, 1H), 8.11 (d, 1H), 7.99 (s, 1H), 7.76 (m, 1H), 7.62 (m, 1H), 7.18 (m, 5H), 7.00 (s, 1H), 6.94 (s, 1H), 6.29 (s, 1H), 6.10 (b, 3H), 3.96 (s, 2H), 3.90 (s, 2H), 3.12 (m, 1H), 2.00 (s, 3H), 1.04 (d, 6H).

TM-148

¹H NMR (CDCl₃, 300 MHz) δ 12.52 (s, OH), 8.28 (d, 1H), 7.73 (dd, 1H), 7.25-7.20 (m, 2H), 7.17-7.11 (m, 4H), 7.03 (s, 1H), 6.88 (d, 1H), 6.59 (s, 1H), 6.39 (b, OH), 6.02 (b, OH), 3.86 (s, 2H), 2.95 (m, 1H), 2.17 (s, 3H), 1.09 (d, 6H); ¹³C NMR (CDCl₃, 75 MHz) δ 202.45, 153.58, 152.93, 149.86, 149.24, 147.06, 139.98, 139.43, 135.27, 131.04, 130.99, 130.96, 130.79, 128.67, 128.33, 127.44, 126.57, 126.13, 123.83 (q), 120.00, 118.22, 117.66, 113.79, 34.98, 31.62, 22.68, 15.54.

TM-149

¹H NMR (CDCl₃, 300 MHz) δ 12.58 (s, OH), 7.99 (d, 1H), 7.43 (d, 1H), 7.22 (m, 2H), 7.16-7.12 (m, 4H), 7.02 (m, 1.5H), 6.98 (d, 0.5H), 6.61 (s, 1H), 6.44 (b, OH), 6.08 (b, OH), 3.87 (s, 2H), 2.96 (m, 1H), 2.15 (s, 3H), 1.09 (d, 6H); ¹³C NMR (CDCl₃, 75 MHz) δ 202.50, 161.03, 153.17, 149.86, 149.27, 147.16, 142.03, 139.98, 135.11, 130.97, 130.90, 128.67, 128.33, 128.26, 127.43, 126.77, 126.31, 126.11, 123.48, 120.00, 118.33, 118.27, 116.28 (q), 113.81, 34.95, 31.62, 30.34, 15.61.

TM-150

¹H NMR (CDCl₃, 300 MHz) δ 8.08 (d, 1H), 7.75 (m, 2H), 7.57 (m, 1H), 7.40 (m, 1H), 7.23-7.16 (m, 5H), 7.04 (s, 1H), 6.93 (s, 1H), 6.91 (d, 1H), 6.33 (s, 1H), 5.90 (b, 3H), 3.93 (s, 2H), 3.89 (s, 2H), 3.16 (m, 1H), 2.00 (s, 3H), 1.08 (d, 6H); ¹³C NMR (CDCl₃, 75 MHz) δ 162.06, 150.46, 146.65, 146.16, 141.445, 141.40, 140.83, 140.51, 134.17, 132.54, 132.14, 130.30, 128.56, 128.38, 127.60, 127.44, 127.07, 125.96, 125.39, 124.91, 122.61, 119.37, 119.22, 118.80, 111.19, 35.74, 32.03, 31.59, 28.75, 23.59.

TM-153

¹H NMR (CDCl₃, 300 MHz) δ 8.08 (d, 1H), 7.54 (m, 2H), 7.57 (m, 1H), 7.40 (m, 1H), 7.22 (m, 6H), 6.98 (m, 3H), 6.52 (s, 1H), 5.50 (b, 3H), 3.92 (s, 2H), 3.90 (s, 2H), 3.11 (m, 1H), 1.13 (d, 6H).

TM-154

¹H NMR (CDCl₃, 300 MHz) δ 8.41 (d, 1H), 8.35 (d, 1H), 8.11 (d, 1H), 7.76 (m, 1H), 7.26 (s, 1H), 7.20 (m, 4H), 7.12 (m, 1H), 7.05 (m, 1H), 6.86 (d, 1H), 6.50 (s, 1H), 6.40 (b, 3H), 6.32 (d, 1H), 3.95 (s, 2H), 3.92 (s, 2H), 2.94 (m, 1H), 1.09 (d, 6H).

TM-155

¹H NMR (CDCl₃, 300 MHz) δ 8.57 (d, 1H), 8.24 (dd, 1H), 7.29 (m, 3H), 7.20 (m, 3H), 7.09 (dd, 1H), 6.86 (d, 1H), 6.81 (d, 1H), 6.51 (s, 1H), 5.45 (b, 1H), 5.19 (b, 1H), 4.91 (b, 1H), 3.93 (s, 2H), 3.92 (s, 2H), 3.00 (m, 1H), 1.16 (d, 6H).

TM-156

¹H NMR (CDCl₃, 300 MHz) δ 8.41 (m, 1H), 8.08 (d, 1H), 7.70 (m, 1H), 7.60 (m, 1H), 7.30 (b, 3OH), 7.14 (m, 4H), 7.07 (m, 1H), 7.00 (s, 1H), 6.93 (s, 1H), 6.26 (s, 1H), 3.96 (d, 2H), 3.89 (s, 2H), 3.12 (m, 1H), 1.97 (s, 3H), 1.04 (d, 6H); ¹³C NMR (CDCl₃, 75 MHz) δ 167.86, 163.30, 150.12, 150.05, 147.40, 147.30, 142.25, 142.14, 141.16, 135.97, 133.22, 132.40, 131.22, 130.92, 128.80, 128.58, 128.19, 126.93, 126.70, 125.72, 122.46, 122.10, 120.97, 119.35, 118.74, 118.01, 102.90, 31.64, 30.34, 28.91, 28.68, 23.59.

TM-158

¹H NMR (CDCl₃, 300 MHz) δ 7.33-7.16 (m, 5H), 7.07-6.91 (m, 4H), 6.77 (s, 1H), 5.44 (b, 2OH), 5.36 (b, OH), 3.87 (s, 2H); ¹³C NMR (CDCl₃, 75 MHz) δ 157.36, 155.48, 142.11, 138.71, 134.99, 132.58, 131.77, 130.08, 129.94, 129.67, 123.05, 120.22, 118.99, 118.68, 34.45.

TM-159

¹H NMR (CDCl₃, 300 MHz) δ 7.33-7.27 (m, 2H), 7.16 (m, 2H), 7.07 (m, 1H), 6.99-6.91 (4H), 6.54 (s, 1H), 5.18 (b, 3OH), 3.89 (s, 2H), 3.11 (m, 1H), 1.23 (d, 6H).

TM-160

¹H NMR (CDCl₃, 300 MHz) δ 7.32-7.26 (m, 2H), 7.17 (d, 2H), 7.08 (m, 1H), 7.00-6.92 (m, 4H), 6.44 (s, 1H), 5.05 (b, 3OH), 3.89 (s, 2H), 2.40 (d, 2H), 1.85 (m, 1H), 0.91 (d, 6H); ¹³C NMR (CDCl₃, 75 MHz) δ 157.35, 155.62, 140.83, 140.00, 135.12, 129.69, 123.10, 122.81, 119.19, 118.88, 118.68, 38.79, 35.41, 29.08, 22.48.

TM-163

¹H NMR (CDCl₃, 300 MHz) δ 7.30-7.25 (m, 4H), 7.19-7.14 (m, 5H), 7.07 (m, 1H), 6.98-6.91 (m, 4H), 6.47 (s, 1H), 5.30 (b, OH), 4.98 (b, OH), 4.78 (b, OH), 3.87 (s, 2H), 2.65 (t, 2H), 2.56 (t, 2H), 1.92 (pent, 2H); ¹³C NMR (CDCl₃, 75 MHz) δ 157.27, 155.67, 142.26, 140.66, 140.00, 134.92, 132.13, 129.70, 128.43, 128.33, 125.75, 123.13, 121.77, 120.63, 119.16, 119.09, 118.70, 35.44, 35.41, 31.48, 28.89.

TM-165

¹H NMR (CDCl₃, 300 MHz) δ 12.60 (s, OH), 7.93 (s, 1H), 7.89-7.84 (m, 3H), 7.73 (d, 2H), 7.63 (d, 1H), 7.50-7.47 (m, 2H), 7.41-7.37 (m, 3H), 7.19 (t, 1H), 7.08 (d, 2H), 7.04 (d, 2H), 6.26 (b, OH), 5.82 (b, OH); ¹³C NMR (CDCl₃, 75 MHz) δ 199.24, 161.26, 155.38, 150.48, 147.30, 134.01, 133.35, 132.50, 132.06, 131.52, 130.06, 128.05, 127.93, 127.84, 127.64, 127.28, 126.73, 126.26, 126.11, 124.64, 120.56, 120.25, 117.24, 113.26.

TM-166

$^1$H NMR (CDCl$_3$, 300 MHz) δ 12.67 (s, OH), 7.67 (d, 2H), 7.41 (m, 2H), 7.19 (d, 2H), 7.10 (d, 2H), 7.05 (d, 2H), 6.51 (d, 2H), 6.16 (b, OH), 5.80 (b, OH); $^{13}$C NMR (CDCl$_3$, 75 MHz) δ 199.18, 161.10, 155.57, 151.36, 149.85, 132.18, 131.45, 131.34, 130.08, 126.26, 124.59, 120.14, 117.28, 113.26, 107.01

TM-167

$^1$H NMR (CDCl$_3$, 300 MHz) δ 12.68 (s, OH), 7.90 (d, 2H), 7.69-7.66 (m, 3H), 7.55-7.40 (m, 4H), 7.38-7.32 (m, 2H), 7.24 (s, 1H), 7.16 (t, 1H), 7.03 (d, 2H), 6.96 (d, 2H), 5.91 (b, OH), 5.81 (b, OH); $^{13}$C NMR (CDCl$_3$, 75 MHz) δ 199.26, 161.16, 155.37, 150.87, 147.48, 133.98, 133.64, 132.10, 131.99, 131.51, 131.45, 130.02, 128.56, 128.40, 128.03, 127.46, 126.34, 126.08, 125.79, 125.48, 124.58, 120.22, 119.12, 117.20, 113.09.

TM-168

$^1$H NMR (CDCl$_3$, 300 MHz) δ 12.95 (s, OH), 12.89 (s, OH), 8.12 (s, 1H), 7.87 (m, 3H), 7.76 (s, 1H), 7.70 (dd, 1H), 7.64-7.62 (m, 3H), 7.48 (t, 1H), 7.34 (m, 2H), 7.22 (m, 1H), 6.88-6.85 (m, 4H), 5.84 (b, OH); $^{13}$C NMR (CDCl$_3$, 75 MHz) δ 200.12, 198.80, 161.53, 155.49, 155.35, 155.02, 134.91, 134.30, 133.07, 132.64, 131.95, 131.32, 131.08, 130.45, 130.10, 128.84, 128.52, 128.48, 127.88, 127.28, 125.00, 124.75, 120.26, 116.97, 112.43, 112.32.

TM-169

$^1$H NMR (CDCl$_3$, 300 MHz) δ 12.95 (s, OH), 12.89 (s, OH), 8.11 (s, 1H), 7.88-7.84 (m, 3H), 7.74 (s, 1H), 7.70 (dd, 1H), 7.64-7.55 (m, 3H), 7.47 (t, 1H), 7.34 (m, 2H), 7.21 (m, 1H), 6.88-6.84 (m, 4H), 5.91 (b, OH); $^{13}$C NMR (CDCl$_3$, 75 MHz) δ 200.09, 198.77, 161.49, 155.48, 155.34, 154.99, 134.87, 134.25, 133.05, 132.63, 131.91, 131.31, 131.04, 130.43, 130.08, 128.82, 128.48, 128.46, 127.84, 127.25, 124.98, 124.73, 120.24, 116.93, 112.40, 112.29.

TM-170

$^1$H NMR (CDCl$_3$, 300 MHz) δ 12.86 (s, 2OH), 7.68 (s, 1H), 7.64 (d, 4H), 7.43 (m, 4H), 7.22 (t, 2H), 7.08 (d, 4H), 7.02 (d, 4H), 5.70 (b, OH); $^{13}$C NMR (CDCl$_3$, 75 MHz) δ 199.38, 161.95, 155.74, 155.70, 133.43, 132.82, 131.81, 131.75, 130.66, 125.27, 120.53, 117.64, 112.72.

TM-171

$^1$H NMR (CDCl$_3$, 300 MHz) δ 12.93 (s, OH), 12.88 (s, OH), 7.74-7.71 (m, 3H), 7.67-7.59 (m, 6H), 7.53-7.43 (m, 3H), 7.22-7.09 (m, 3H), 6.99 (d, 2H), 6.94 (d, 2H), 5.66 (b, OH); $^{13}$C NMR (CDCl$_3$, 75 MHz) δ 199.84, 198.90, 161.67, 155.38, 155.12, 145.31, 139.69, 135.80, 133.03, 132.48, 131.44, 131.21, 130.07, 129.68, 129.10, 128.42, 127.34, 127.06, 124.78, 120.11, 117.08, 112.38, 112.27.

TM-172

$^1$H NMR (CDCl$_3$, 300 MHz) δ 13.09 (s, OH), 12.82 (s, OH), 7.53 (d, 2H), 7.47-7.41 (m, 3H), 7.23 (m, 1H), 7.10 (d, 1H), 7.05 (d, 2H), 6.94 (d, 2H), 6.84 (d, 1H), 6.63 (dd, 1H), 5.63 (s, OH), 5.47 (s, OH), 3.02 (m, 1H), 1.13 (d, 6H); $^{13}$C NMR (CDCl$_3$, 75 MHz) δ 203.38, 199.15, 161.91, 158.39, 155.82, 155.75, 150.44, 133.25, 133.112, 131.94, 131.49, 130.59, 130.14, 128.86, 125.18, 120.51, 117.60, 114.15, 113.71, 112.66, 112.35, 30.48, 24.36.

TM-175

$^1$H NMR (CDCl$_3$, 300 MHz) δ 12.96 (s, 2OH), 8.11 (s, 2H), 7.83-7.75 (m, 7H), 7.69 (d, 2H), 7.52 (m, 4H), 5.71 (b, OH); $^{13}$C NMR (CDCl$_3$, 75 MHz) δ 200.22, 155.46, 134.80, 134.33, 133.07, 132.94, 132.01, 130.14, 129.00, 128.42, 128.31, 127.80, 127.00, 124.83, 112.62.

TM-176

$^1$H NMR (CDCl$_3$, 300 MHz) δ 13.10 (s, 2OH), 11.01 (s, 1H), 8.05 (m, 4H), 7.60 (m, 4H), 5.32 (s, OH).

TM-177

$^1$H NMR (CDCl$_3$, 300 MHz) δ 7.26-7.15 (m, 6H), 6.94-6.92 (m, 2H), 6.68-6.61 (m, 3H), 6.48 (s, 1H), 4.52 (b, 4H), 3.90 (s, 2H), 3.85 (s, 2H), 3.25 (m, 1H), 1.19 (d, 6H).

TM-178

$^1$H NMR (CDCl$_3$, 300 MHz) δ 13.41 (s, OH), 9.48 (s, 1H), 8.17 (m, 1H), 8.07-7.98 (m, 3H), 7.56 (m, 4H), 5.30 (s, OH), 4.06 (s, 3H); $^{13}$C NMR (CDCl$_3$, 75 MHz) δ 186.26, 185.51, 167.24, 166.94, 155.70, 153.51, 153.06, 152.07, 137.37, 137.14, 136.59, 129.03, 128.08, 127.60, 127.23, 126.96, 125.63, 125.53, 122.73, 122.37, 122.09, 113.55, 61.46.

TM-179

$^1$H NMR (CDCl$_3$, 300 MHz) δ 13.16 (s, OH), 12.97 (s, OH), 9.68 (s, 1H), 8.02 (d, 1H), 7.90 (d, 3H), 7.55 (m, 4H), 7.17 (d, 3H), 7.03 (d, 2H), 5.60 (s, OH); $^{13}$C NMR (CDCl$_3$, 75 MHz) δ 199.11, 185.50, 166.90, 161.76, 156.34, 155.77, 155.39, 153.38, 136.66, 134.05, 132.74, 132.18, 131.48, 130.22, 128.01, 127.24, 125.27, 124.87, 122.22, 120.38, 117.22, 113.26, 111.20.

TM-180

$^1$H NMR (CO(CD$_3$)$_2$, 300 MHz) δ 12.88 (s, 1H), 12.61 (s, 1H), 9.71 (s, 1H), 8.24 (m, 2H), 8.09-7.99 (m, 3H), 7.64 (m, 2H), 7.47 (d, 2H), 7.41 (d, 1H), 7.25 (dd, 1H), 3.24 (m, 4H), 1.59 (m, 6H); $^{13}$C NMR (CO(CD$_3$)$_2$, 75 MHz) δ 200.15, 186.80, 167.94, 161.00, 159.68, 154.37, 137.39, 134.91, 134.72, 134.48, 133.19, 132.76, 129.12, 128.39, 126.02, 123.50, 122.81, 120.29, 120.12, 117.76, 114.37, 112.10, 47.28, 26.36, 24.34.

TM-183

$^1$H NMR (CDCl$_3$, 300 MHz) δ 13.28 (s, OH), 13.24 (s, OH), 9.58 (s, 1H), 7.92 (d, 2H), 7.69 (t, 3H), 7.58 (t, 1H), 7.46 (m, 4H), 7.16 (d, 4H), 5.66 (s, OH); $^{13}$C NMR (CDCl$_3$, 75 MHz) δ 198.90, 181.53, 161.97, 156.76, 156.29, 155.64, 155.44, 150.20, 140.48, 133.90, 132.77, 132.36, 131.16, 130.21, 128.88, 126.03, 124.90, 122.05, 120.44, 117.22, 113.13, 111.98, 111.55; $^{13}$C NMR (CO(CD$_3$)$_2$, 75 MHz) δ 207.06, 198.90, 181.53, 161.97, 156.76, 156.29, 155.64, 155.44, 150.20, 140.48, 133.90, 132.77, 132.36, 131.16, 130.21, 128.88, 126.03, 124.90, 122.05, 120.44, 117.22, 113.13, 111.98, 111.55.

TM-190

¹H NMR (CDCl₃, 300 MHz) δ 9.69 (b, OH), 7.99 (s, 1H), 7.79 (dd, 1H), 7.40 (s, 1H), 7.38 (d, 1H), 7.24-7.17 (m, 4H), 6.81 (s, 1H), 6.68 (b, OH), 4.82 (s, 2H), 3.96-3.81 (m, 4H), 3.32-3.23 (m, 2H), 3.07-2.98 (m, 6H), 2.87-2.82 (m, 2H), 1.66 (m, 4H), 1.47 (m, 2H); ¹³C NMR (CDCl₃, 75 MHz) δ 168.73, 149.43, 143.15, 139.34, 135.43, 133.94, 133.28, 131.98, 130.55, 129.86, 128.86, 128.71, 128.53, 127.15, 126.79, 126.57, 115.91, 115.24, 113.89, 84.72, 47.01, 38.78, 28.87, 28.32, 25.14, 23.45.

TM-191

¹H NMR (CD₃OD, 300 MHz) δ 7.57-7.51 (m, 2H), 7.31-7.26 (m, 2H), 7.18-7.14 (m, 9H), 4.77 (m, 2H), 4.40 (s, 2H), 4.10 (t, 1H), 3.80 (m, 2H), 3.60-3.53 (m, 4H), 3.00 (m, 4H), 2.92 (m, 6H), 1.77 (m, 2H).

TM-193

¹H NMR (CDCl₃, 300 MHz) δ 10.34 (s, OH), 8.82 (s, 1H), 7.60 (d, 1H), 7.51 (s, 1H), 7.35 (d, 1H), 7.31 (s, 1H), 7.18-7.15 (m, 2H), 7.10 (m, 1H), 7.05-7.02 (m, 1H), 5.68 (s, 1H), 4.88 (s, 2H), 4.34 (s, 2H), 3.90 (t, 2H), 3.73 (s, 2H), 3.46 (t, 2H), 3.06 (2H), 3.00-2.92 (m, 4H), 1.65 (m, 4H), 1.43 (m, 2H); ¹³C NMR (CDCl₃, 75 MHz) δ 169.67, 151.08, 145.60, 139.15, 134.94, 133.83, 133.37, 132.70, 130.85, 129.57, 128.90, 127.10, 126.60, 126.31, 125.72, 120.04, 112.14, 110.62, 47.27, 46.96, 43.66, 43.46, 28.92, 28.54, 25.13, 23.46.

TM-194

¹H NMR (CDCl₃, 300 MHz) δ 10.15 (s, OH), 8.74 (s, 1H), 7.69 (d, 1H), 7.63 (s, 1H), 7.30 (m, 2H), 7.16-7.12 (m, 2H), 7.10-7.08 (m, 1H), 7.04-7.01 (m, 1H), 6.04 (s, 1H), 4.84 (s, 2H), 4.32 (s, 2H), 3.86 (t, 2H), 3.43 (t, 2H), 3.04 (t, 2H), 2.92 (t, 2H), 2.74 (t, 2H), 1.74 (m, 1H), 0.87 (d, 6H); ¹³C NMR (CDCl₃, 75 MHz) δ 169.46, 150.70, 145.59, 139.16, 138.64, 133.80, 133.58, 132.74, 130.89, 129.62, 128.89, 127.06, 126.56, 126.31, 125.65, 125.08, 120.12, 112.28, 110.01, 50.58, 47.26, 43.56, 28.87, 28.52, 19.89.

TM-197

¹H NMR (CO(CD₃)₂, 300 MHz) δ 7.65-7.63 (m, 3H), 7.45 (m, 1H), 7.41-7.37 (m, 2H), 7.30 (s, 0.5H), 7.21-7.14 (m, 7H), 6.83 (s, 0.5H), 4.89-4.86 (m, 3H), 4.39 (s, 1H), 3.87 (m, 3.5H), 3.52 (t, 0.5H), 3.26 (m, 1H), 3.17-3.11 (m, 4H), 2.93 (t, 1H), 2.76 (m, 2H).

TM-198

¹H NMR (CO(CD₃)₂, 300 MHz) δ 9.74 (b, 1H), 9.41 (s, 1H), 9.11 (s, 1H), 7.66-7.60 (m, 4H), 7.44-7.13 (m, 13H), 6.83 (s, 1H), 6.55 (t, 1H), 4.83 (s, 2H), 4.20 (t, 2H), 3.85 (m, 2H), 3.59 (m, 2H), 3.41 (m, 1H), 3.25 (m, 2H), 3.05 (m, 2H), 2.91 (m, 2H).

TM-199

¹H NMR (CO(CD₃)₂, 300 MHz) δ 10.12 (b, OH), 9.08 (s, 1H), 8.57 (s, 1H), 7.47 (d, 1H), 7.40 (m, 1H), 7.24 (d, 1H), 7.14-7.04 (m, 9H), 6.62 (d, 1H), 6.53 (b, 1H), 4.78 (s, 2H), 4.41 (s, 2H), 4.06 (m, 1H), 3.84 (t, 2H), 3.54 (t, 2H), 3.02 (m, 2H), 2.95-2.89 (m, 4H); ¹³C NMR (CDCl₃, 75 MHz) δ 167.46, 148.30, 143.51, 143.07, 140.52, 139.87, 135.40, 130.88, 130.75, 130.52, 130.32, 129.75, 129.32, 128.88, 127.50, 127.40, 127.08, 125.91, 125.76, 118.62, 116.09, 115.80, 86.37, 66.10, 52.00, 48.17, 48.08, 44.60, 39.81.

TM-1202

¹H NMR (CO(CD₃)₂, 300 MHz) δ 9.24-8.58 (b, OH), 7.61-7.59 (m, 2H), 7.39-7.30 (m, 4H), 7.21-7.14 (m, 7H), 6.84 (s, 2H), 4.85 (s, 1H), 4.82 (s, 1H), 4.52 (s, 1H), 3.88 (s, 1H), 3.88-3.71 (m, 3H), 3.53-3.25 (m, 10H), 3.30-2.86 (m, 6H).

TM-1205

¹H NMR (CO(CD₃)₂, 300 MHz) δ 9.17 (b, 2OH), 7.66-7.64 (m, 2H), 7.35-7.33 (m, 2H), 7.23-7.11 (m, 10H), 6.53 (b, 1H), 4.86 (s, 2H), 3.82 (m, 2H), 3.38 (m, 2H), 3.14 (m, 2H), 2.98 (m, 2H), 2.88-2.74 (m, 7H); ¹³C NMR (CO(CD₃)₂, 75 MHz) δ 169.23, 150.40, 146.72, 140.27, 139.69, 139.50, 139.48, 135.09, 134.51, 130.28, 129.58, 129.49, 129.18, 129.11, 127.09, 127.04, 125.83, 125.74, 120.95, 115.35, 113.88, 52.34, 47.30, 45.30, 36.52, 35.26, 35.01, 20.84.

TM-1206

¹H NMR (CO(CD₃)₂, 300 MHz) δ 10.12 (b, OH), 9.06 (b, OH), 8.48 (b, OH), 7.65 (d, 1H), 7.63 (s, 1H), 7.51 (m, 1H), 7.41-7.32 (m, 3H), 7.23-7.14 (m, 8H), 6.50 (t, 1H), 4.88 (s, 2H), 3.87 (t, 2H), 3.17 (t, 2H), 3.05 (t, 2H), 2.90-2.89 (m, 2H), 2.84 (s, 3H), 2.78 (t, 2H), 2.64 (t, 2H), 1.87 (m, 2H); ¹³C NMR (CO(CD₃)₂, 75 MHz) δ 169.36, 150.76, 146.87, 142.57, 140.43, 139.95, 139.67, 135.34, 134.60, 130.39, 129.62, 129.34, 129.22, 129.18, 128.27, 127.15, 126.66, 125.96, 125.84, 121.42, 121.09, 115.29, 113.69, 53.35, 50.48, 49.56, 45.42, 38.70, 36.67, 35.04, 33.39, 20.83.

TM-1209

¹H NMR (CO(CD₃)₂, 300 MHz) δ 10.14 (b, OH), 9.07 (b, OH), 8.52 (b, OH), 7.65-7.61 (m, 2H), 7.40 (s, 1H), 7.39 (d, 1H), 7.24 (d, 2H), 7.18-7.14 (m, 6H), 6.53 (t, 1H), 4.90 (s, 2H), 4.40 (s, 2H), 3.88 (t, 2H), 3.53 (t, 2H), 3.18 (t, 2H), 3.08 (m, 2H), 2.92 (m, 2H), 2.77 (t, 2H); ¹³C NMR (CO(CD₃)₂, 75 MHz) δ 169.31, 151.01, 147.08, 140.45, 139.94, 138.68, 135.29, 134.65, 134.29, 133.00, 132.44, 131.44, 130.42, 129.67, 129.14, 127.52, 127.29, 127.11, 125.97, 125.77, 121.45, 114.32, 113.77, 48.12, 45.16, 45.06, 44.60, 35.91.

TM-1212

¹H NMR (CO(CD₃)₂, 300 MHz) δ 10.11 (b, OH), 9.06 (b, OH), 8.54 (b, OH), 7.97 (d, 2H), 7.68-7.64 (m, 2H), 7.40-7.39 (m, 2H), 7.22 (d, 2H), 7.12 (m, 4H), 7.00-6.96 (m, 4H), 6.55 (t, 1H), 4.91 (s, 2H), 4.37 (s, 2H), 3.87 (t, 2H), 3.50 (t, 2H), 3.17 (t, 2H), 3.05 (m, 2H), 2.90 (t, 2H), 2.80 (t, 2H); ¹³C NMR (CO(CD₃)₂, 75 MHz) δ 169.29, 162.75, 154.84, 150.92, 147.02, 140.44, 139.89, 136.15, 135.26, 132.89, 131.39, 130.41, 129.63, 127.49, 127.25, 127.07, 125.97, 125.80, 121.41, 120.90, 117.80, 114.21, 113.80, 48.08, 45.36, 44.56, 35.94, 26.54, 20.83.

TM-1214

¹H NMR (CO(CD₃)₂, 300 MHz) δ 10.01 (b, OH), 8.90 (b, OH), 7.46-7.30 (m, 2H), 7.19-6.98 (m, 7H), 6.72 (b, 1H), 4.77 (s, 2H), 4.29 (s, 2H), 3.81 (m, 2H), 3.40 (t, 2H), 2.94 (m, 2H), 2.87 (m, 2H).

TM-1217

¹H NMR (CO(CD₃)₂, 300 MHz) δ 10.22 (b, OH), 9.15 (b, OH), 8.43 (b, OH), 7.65 (m, 2H), 7.40 (d, 1H), 7.38 (s, 1H), 7.24-7.13 (m, 5H), 6.49 (t, NH), 6.33 (m, NH), 4.90 (s, 2H), 3.90 (t, 2H), 3.14 (t, 2H), 3.07 (t, 2H), 2.94 (m, 2H), 2.77 (t, 2H), 2.60 (d, 3H); ¹³C NMR (CO(CD₃)₂, 75 MHz) δ 169.71, 150.94, 146.71, 140.43, 139.93, 139.67, 135.34, 134.44, 130.36, 129.61, 129.21, 127.14, 125.95, 125.86, 120.97, 116.15, 113.10, 45.42, 45.32, 36.65.

TM-1218

¹H NMR (CO(CD₃)₂, 300 MHz) δ 10.02 (b, 1H), 9.04 (b, 2H), 7.69-7.64 (m, 3H), 7.43 (m, 2H), 7.12 (m, 4H), 6.91-6.82 (m, 1H), 6.67-6.43 (m, 3H), 5.13 (s, 1H), 4.93 (d, 2H), 4.37 (s, 2H), 3.87 (t, 2H), 3.50 (m, 2H), 3.24 (m, 2H), 3.05 (m, 2H), 2.91 (m, 2H), 2.71 (m, 2H); ¹³C NMR (CO(CD₃)₂, 75 MHz) δ 169.24, 150.75, 146.99, 145.72, 144.85, 144.35, 141.05, 140.32, 139.87, 135.46, 135.40, 135.19, 134.59, 134.19, 132.86, 129.61, 127.48, 127.23, 127.06, 121.34, 114.14, 96.30, 96.16, 48.08, 44.56, 36.05, 28.70.

TM-1219

¹H NMR (CO(CD₃)₂, 300 MHz) δ 9.07 (b, 1H), 7.58-7.09 (m, 18H), 6.58 (s, 1H), 4.89 (s, 2H), 4.35 (s, 2H), 3.81 (t, 2H), 3.64 (m, 2H), 3.19 (m, 2H), 2.99 (m, 2H), 2.82 (m, 4H); ¹³C NMR (CO(CD₃)₂, 75 MHz) δ 169.24, 150.83, 147.02, 141.42, 140.35, 139.83, 139.72, 138.84, 135.31, 135.18, 134.61, 134.16, 132.84, 132.66, 130.84, 130.62, 130.38, 130.16, 129.66, 129.43, 127.98, 127.61, 127.23, 125.96, 125.78, 121.39, 114.17, 48.07, 45.32, 44.55, 39.75, 36.22, 23.23, 20.83, 14.34.

TM-1220

¹H NMR (CO(CD₃)₂, 300 MHz) δ 9.17 (b, OH), 7.71-7.36 (m, 13H), 7.12 (m, 5H), 5.62 (s, 2H), 4.89 (s, 2H), 4.19 (m, 2H), 3.80 (m, 2H), 3.49 (m, 2H), 3.01 (m, 2H), 2.90 (m, 2H); ¹³C NMR (CO(CD₃)₂, 75 MHz) δ 169.23, 150.77, 146.99, 141.21, 140.67, 140.30, 140.04, 137.54, 135.30, 135.04, 134.60, 134.14, 132.81, 130.34, 129.68, 129.58, 129.23, 128.14, 127.54, 127.50, 127.22, 127.02, 126.07, 125.81, 121.37, 114.12, 113.91, 48.05, 47.34, 44.54, 39.75, 28.58.

TM-1225

¹H NMR (CO(CD₃)₂, 300 MHz) δ 10.26 (s, OH), 8.30 (b, 1H), 7.98 (s, 1H), 7.85 (m, 2H), 7.69 (m, 3H), 7.46-7.37 (m, 4H), 7.13 (m, 4H), 4.42 (s, 2H), 3.56 (t, 2H), 2.90 (t, 2H); ¹³C NMR (CO(CD₃)₂, 75 MHz) δ 170.93, 156.31, 141.14, 138.16, 134.56, 134.49, 133.32, 129.74, 129.68, 128.07, 127.97, 127.48, 127.41, 127.18, 127.01, 122.87, 121.07, 47.99, 44.51, 20.83.

TM-1226

¹H NMR (CO(CD₃)₂, 300 MHz) δ 9.10 (b, OH), 7.66-7.61 (m, 2H), 7.44 (d, 1H), 7.38 (s, 1H), 7.31-7.20 (m, 5H), 6.36 (b, 1H), 4.93 (s, 2H), 3.90 (m, 2H), 3.28 (t, 2H), 3.08 (m, 2H), 2.85 (t, 2H), 2.77 (s, 3H), 2.59 (s, 3H); ¹³C NMR (CO(CD₃)₂, 75 MHz) δ 169.60, 150.64, 146.63, 140.77, 139.62, 136.93, 135.53, 134.35, 130.46, 129.66, 129.41, 129.25, 127.16, 126.39, 126.31, 120.90, 116.09, 113.37, 35.38, 35.08, 20.84.

TM-1227

¹H NMR (CO(CD₃)₂, 300 MHz) δ 9.33 (b, OH), 7.99 (b, 1H), 7.64-7.62 (m, 2H), 7.42-7.22 (m, 12H), 4.94 (s, 2H), 4.32 (s, 2H), 3.89 (m, 2H), 3.26 (m, 2H), 3.07 (m, 2H), 2.94 (m, 2H), 2.75 (s, 3H), 2.68 (s, 3H); ¹³C NMR (CO(CD₃)₂, 75 MHz) δ 169.50, 163.05, 150.92, 147.04, 140.76, 139.59, 137.48, 136.92, 135.49, 134.67, 130.46, 129.64, 129.23, 129.09, 128.49, 127.15, 126.37, 126.29, 121.37, 115.35, 113.52, 54.58, 52.31, 35.37, 35.06, 34.73, 20.83.

TW-1—5-Benzyl-4'-(5-phenyl-pentyl)-biphenyl-2,3,4-triol

¹H NMR (CD₃COCD₃, 300 MHz) δ (ppm) 7.34-7.19 (m, 14H), 6.64 (s, 1H), 5.56 (s, 1H), 5.43 (s, 1H), 5.36 (s, 1H), 4.0 (s, 2H), 2.67-2.70 (m, 4H), 1.85-1.65 (m, 4H), 1.41-1.26 (m, 4H); ¹³C NMR (CD₃COCD₃) δ (ppm) 142.79, 142.10, 141.86, 140.73, 138.87, 134.32, 132.35, 131.56, 129.18, 128.71, 128.33, 126.04, 125.60, 121.88, 120.38, 120.07, 35.95, 35.61, 31.41, 29.14, 21.06, 14.19.

TW-2—5-Benzyl-4'-decyl-biphenyl-2,3,4-triol

¹H NMR (CD₃COCD₃, 300 MHz) δ (ppm) 7.36-7.20 (m, 9H), 6.63 (s, 1H), 5.39 (s, 1H), 5.31 (s, 1H), 5.26 (s, 1H), 4.0 (s, 2H), 2.65 (t, 2H), 1.62-1.58 (m, 4H), 1.34-1.27 (m, 14H), 0.99-0.88 (m, 3H); ¹³C NMR (CD₃COCD₃) δ (ppm) 142.36, 141.76, 140.68, 138.68, 134.16, 131.55, 129.28, 128.70, 128.46, 126.07, 121.81, 120.28, 120.07, 31.91, 31.60, 31.50, 29.63, 29.60, 29.53, 29.38, 29.35.

TW-3—5-Benzyl-4'-tert-butyl-biphenyl-2,3,4-triol

¹H NMR (CD₃COCD₃, 300 MHz) δ (ppm) 7.50 (d, 2H), 7.38 (d, 2H), 7.21-7.20 (m, 5H), 6.64 (s, 1H), 5.36 (s, 1H), 5.30 (s, 1H), 5.25 (s, 1H), 4.0 (s, 2H), 1.38 (s, 9H); ¹³C NMR (CD₃COCD₃) δ (ppm) 141.77, 140.64, 138.73, 133.99, 131.53, 128.71, 128.50, 128.46, 126.16, 126.06, 121.86, 120.26, 120.13, 35.61, 34.59, 31.31.

TW-4—4'-tert-Butyl-5-isopropyl-biphenyl-2,3,4-triol

¹H NMR (CD₃COCD₃, 300 MHz) δ (ppm) 7.42-7.31 (m, 4H), 6.72 (s, 1H), 5.70 (s, 1H), 5.64 (s, 1H), 5.37 (s, 1H), 3.33-3.20 (m, 1H), 2.70 (q, 2H), 1.73-1.63 (m, 2H), 1.41-1.20 (m, 16H), 0.95 (t, 3H); ¹³C NMR (CD₃COCD₃) δ (ppm) 142.31, 141.32, 137.88, 134.51, 131.10, 129.28, 128, 76, 127.65, 120.20, 117.78, 35.69, 31.93, 31.52, 29.64, 29.56, 29.42, 29.37, 26.85.

TW-5—4'-Decyl-5-isopropyl-biphenyl-2,3,4-triol

¹H NMR (CD₃COCD₃, 300 MHz) δ (ppm) 7.52 (d, 2H), 7.40 (d, 2H), 6.68 (s, 1H), 5.43 (s, 2H), 5.21 (s, 1H), 3.31-3.21 (m, 1H), 1.39 (s, 9H), 1.26 (d, 6H); ¹³C NMR (CD₃COCD₃) δ (ppm) 150.17, 140.43, 137.84, 134.32, 131.09, 128.53, 126.26, 117.67, 120.01, 34.62, 31.33, 26.88, 22.73.

TW-6—5-(3-Phenyl-propyl)-4'-undecyl-biphenyl-2,3,4-triol

¹H NMR (CD₃COCD₃, 300 MHz) δ (ppm) 7.39-7.14 (m, 9H), 6.56 (s, 1H), 5.51 (s, 1H), 5.45 (s, 1H), 5.28 (s, 1H), 2.76-2.55 (m, 6H), 2.05-1.95 (m, 2H), 1.77-1.56 (m, 2H), 1.48-1.23 (m, 16H), 0.93 (t, 3H); ¹³C NMR (CD₃COCD₃) δ (ppm) 142.77, 142.36, 141.85, 138.12, 134.28, 131.26, 129.30, 129.13, 128.68, 128.25, 125.63, 121.21, 120.11, 31.91, 31.53, 31.50, 29.65, 29.62, 29.54, 29.38, 29.35, 29.12,

TW-7—5-[2-(4-tert-Butyl-phenyl)-ethyl]-4'-unedcyl-biphenyl-2,3,4-triol $^1$H NMR (CD$_3$COCD$_3$, 300 MHz) δ (ppm) 7.52-7.18 (m, 8H), 6.57 (s, 1H), 5.45 (s, 1H), 5.33 (s, 1H), 5.29 (s, 1H), 2.71-2.60 (m, 4H), 2.68 (t, 2H), 1.92-1.60 (m, 2H), 1.50-1.22 (m, 21H), 0.93 (t, 3H); $^{13}$C NMR (CD$_3$COCD$_3$) δ (ppm) 148.63, 142.29, 141.73, 139.13, 138.22, 134.24, 131.36, 130.55, 129.56, 128.66, 128.23, 125.20, 121.42, 120.90, 120.09, 31.91, 31.86, 31.51, 31.42, 29.64, 29.60, 29.53, 29.39, 29.35, 22.70, 14.14.

TW-8—5-(4-Tertbutyl-benzyl)-4'-undecyl-biphenyl-2,3,4-triol $^1$H NMR (CD$_3$COCD$_3$, 300 MHz) δ (ppm): 7.42-7.25 (m, 8H), 6.71 (s, 1H), 5.55 (s, 1H), 5.41 (s, 1H), 5.36 (s, 1H), 4.16 (s, 2H), 2.70 (t, 2H), 1.70 (m, 2H), 1.36 (m, 23H), 0.96 (t, 3H); $^{13}$C NMR (CD$_3$COCD$_3$) δ (ppm):149.28, 142.72, 142.22, 139.22, 137.96, 134.71, 132.05, 129.65, 129.20, 128.72, 125.86, 122.40, 120.91, 120.71, 36.14, 35.63, 34.80, 32.89, 32.07, 31.96, 31.84, 30.12, 30.09, 30.01, 29.87, 29.82, 23.17, 14.62.

TW-9—5-(4-Isopropyl-benzyl)-4'-undecyl-biphenyl-2,3,4-triol $^1$H NMR (CD$_3$COCD$_3$, 300 MHz) δ (ppm) 7.39-7.15 (m, 8H), 6.67 (s, 1H), 5.39 (s, 1H), 5.29 (s, 1H), 5.27 (s, 1H), 4.0 (s, 2H), 2.94-2.84 (m, 1H), 2.66 (t, 2H), 1.67-1.62 (m, 2H), 1.36-1.23 (m, H), 0.91 (t, 3H); $^{13}$C NMR (CD$_3$COCD$_3$) δ (ppm) 146.61, 142.29, 141.70, 138.71, 137.84, 134.23, 131.58, 129.22, 128.71, 128.52, 126.57, 121.84, 120.37, 120.21, 35.68, 35.31, 33.68, 31.91, 31.50, 29.64, 29.61, 29.53, 29.39, 29.35, 24.03, 22.70, 14.13.

TW-10—5-Benzyl-4'-undecyl-biphenyl-2,3,4-triol $^1$H NMR (CD$_3$COCD$_3$, 300 MHz) δ (ppm) 7.30-6.85 (m, 9H), 6.46 (s, 1H), 5.53 (s, 1H), 5.03 (s, 1H), 3.70 (s, 2H), 2.75 (t, 2H), 1.74-1.69 (m, 2H), 1.52-1.24 (m, 14H), 0.95 (t, 3H); $^{13}$C NMR (CD$_3$COCD$_3$) δ (ppm) 143.34, 142.91, 141.24, 140.70, 131.72, 131.31, 130.65, 129.42, 129.21, 128.75, 128.06, 125.66, 120.96, 109.3, 38.83, 35.71, 31.93, 31.41, 29.71, 29.66, 29.55, 29.38, 22.70, 14.14.

TW-11—5-Benzyl-4'-(3-phenyl-propyl)-biphenyl-2,3,4-triol $^1$H NMR (CD$_3$COCD$_3$, 300 MHz) δ (ppm) 7.60-7.21 (m, 14H), 6.68 (s, 1H), 5.63 (s, 1H), 5.54 (s, 1H), 5.32 (s, 1H), 4.03 (s, 2H), 3.00 (s, 1H); $^{13}$C NMR (CD$_3$COCD$_3$) δ (ppm) 141.80, 141.57, 141.09, 140.60, 138.73, 134.56, 131.57, 129.26, 128.81, 128.68, 128.46, 128.41, 128.38, 126.08, 126.01, 121.87, 120.31, 120.13, 37.78, 37.53, 35.62.

TW-12—5,4'-Dibenzyl-biphenyl-2,3,4-triol $^1$H NMR (CD$_3$COCD$_3$, 300 MHz) δ (ppm) 7.40-7.19 (m, 14H), 6.64 (m, 1H), 5.44 (s, 1H), 5.36 (s, 1H), 5.27 (s, 1H), 4.03 (s, 2h), 3.95 (s, 2H); $^{13}$C NMR (CD$_3$COCD$_3$) δ (ppm) 141.81, 140.77, 140.57, 140.49, 138.73, 134.74, 131.60, 131.59, 129.56, 129.05, 128.58, 128.54, 128.51, 128.20, 126.12, 126.08, 121.85, 120.21, 120.17, 41.63, 35.62.

TW-13—5-Methyl-4'-undecyl-biphenyl-2,3,4-triol $^1$H NMR (CD$_3$COCD$_3$, 300 MHz) δ (ppm) 7.31 (d, 2H), 7.18 (d, 2H), 6.49 (s, 1H), 5.38 (s, 1H), 5.21 (s, 1H), 4.92 (s, 1H), 2.68 (t, 2H), 2.01 (s, 3H), 1.74-1.61 (m, 2H), 1.41-1.28 (m, 16H), 0.90 (t, 3H); $^{13}$C NMR (CD$_3$COCD$_3$) δ (ppm) 143.16, 142.84, 140.49, 132.19, 130.37, 129.38, 128.96, 128.04, 35.77, 31.94, 31.40, 29.69, 29.65, 29.63, 29.44, 29.35, 29.27, 22.70, 19.77, 14.14.

TW-14—5-(2-Isopropyl-benzyl)-4'-undecyl-biphenyl-2,3,4-triol $^1$H NMR (CD$_3$COCD$_3$, 300 MHz) δ (ppm) 7.40-7.10 (m, 8H), 6.4 (s, 1H), 5.38 (s, 1H), 5.37 (s, 1H), 5.22 (s, 1H), 4.0 (s, 2H), 3.27-3.20 (m, 1H), 2.64 (t, 2H), 1.65-1.58 (m, 2H), 1.46-1.21 (m, 20H), 0.91 (t, 3H); $^{13}$C NMR (CD$_3$COCD$_3$) δ (ppm) 147.31, 142.30, 141.58, 138.42, 136.51, 134.18, 131.30, 129.93, 129.24, 128.68, 126.82, 125.73, 125.42, 121.30, 120.24, 119.98, 35.65, 32.20, 31.92, 31.47, 29.70, 29.64, 29.60, 29.53, 29.38, 29.34, 28.83, 23.77, 22.70, 14.14.

TW-15—N-[2-Chloro-4-(4-chloro-benzenesulfonyl)-phenyl]-2,3,4-trihydroxy-5-phenethyl-benzamide $^1$H NMR (CD$_3$COCD$_3$, 300 MHz) δ (ppm) 12.30 (s, 1H), 7.72-7.21 (m, 14H), 6.58 (s, 1H), 5.91 (s, 1H), 5.67 (s, 1H), 2.96 (s, 4H), 2.7 (t, 2H), 1.74-1.68 (m, 2H), 1.58-1.21 (m, 14H), 0.91 (t, 3H); $^{13}$C NMR (CD$_3$COCD$_3$) δ (ppm) 148.15, 146.44, 143.58, 141.94, 140.24, 138.22, 135.86, 131.59, 128.93, 128.72, 128.31, 127.78, 127.45, 127.05, 125.96, 124.24, 121.18, 119.45, 117.57, 36.19, 36.11, 31.92, 31.74, 31.62, 29.63, 29.55, 29.42, 29.36, 22.71, 14.15.

TW-16—N-[2-Chloro-4-(4-chloro-benzenesulfonyl)-phenyl]-2,3,4-trihydroxy-5-benzyl-benzamide $^1$H NMR (CD$_3$COCD$_3$, 300 MHz) δ (ppm) 11.80 (s, 1H), 9.07 (d, 2H), 8.29 (s, 1H), 7.95 (d, 2H), 7.61-7.14 (m, 10H), 7.65 (s, 1H), 6.63 (s, 1H), 5.86 (s, 1H), 2.95 (s, 4H); $^{13}$C NMR (CD$_3$COCD$_3$) δ (ppm) 148.42, 147.22, 141.50, 140.94, 140.30, 139.53, 134.99, 131.66, 130.05, 129.79, 129.26, 128.61, 128.30, 126.02, 123.37, 120.67, 120.14, 117.42, 106.16, 35.74, 31.71.

TW-20—N-(4-phenyloxy-phenyl)-2,3,4-trihydroxy-5-phenethyl-benzamide $^1$H NMR (CD$_3$COCD$_3$, 300 MHz) δ (ppm) 11.29 (s, 1H), 7.51-7.02 (m, 15H), 6.57 (s, 1H), 5.91 (s, 1H), 5.69 (s, 1H), 2.94 (s, 4H); $^{13}$C NMR (CD$_3$COCD$_3$) δ (ppm) 168.33, 157.21, 154.36, 148.11, 146.42, 141.93, 131.89, 131.57, 129.78, 128.89, 128.29, 125.92, 123.35, 122.92, 119.50, 119.42, 118.72, 117.52, 106.45, 36.16, 31.75.

TW-21—N-(3-Benzenesulfonyl-phenyl)-2,3,4-trihydroxy-5-phenethyl-benzamide $^1$H NMR (CD$_3$COCD$_3$, 300 MHz) δ (ppm) 12.0 (s, 1H), 8.15-7.21 (m, 15H), 6.72 (s, 1H), 6.00 (s, 1H), 5.79 (s, 1H), 2.89 (s, 4H); $^{13}$C NMR (CD$_3$COCD$_3$) δ (ppm) 148.50, 147.20, 142.11, 142.0, 133.49, 131.52, 131.20, 129.42, 128.88, 128.30, 127.66, 125.92, 124.62, 120.05, 119.68, 118.21, 36.15, 31.58.

TW-22—N-(3-Benzenesulfonyl-phenyl)-5-[2-(4-tert-butyl-phenyl)-ethyl]-2,3,4-trihydroxy-benzamide $^1$H NMR (CD$_3$COCD$_3$, 300 MHz) δ (ppm) 12.08 (s, 1H), 8.19 (d, 2H), 7.97 (t, 3H), 7.72 (d, 1H), 7.62-7.16 (m, 10H), 6.89 (s, 1H), 5.96 (s, 1H), 5.73 (s, 1H), 2.89 (s, 1H), 1.32 (s, 9H); ¹³C NMR (CD₃COCD₃) δ (ppm) 168.68, 148.74, 148.35, 146.91, 142.14, 141.02, 138.86, 138.19, 133.44, 131.56, 130.93, 130.20, 129.40, 128.84, 128.21, 127.65, 125.72, 125.20, 123.60, 120.34, 119.62, 117.65, 106.24, 35.64, 34.35, 31.60, 31.41.

TW-23—5-[2-(4-tert-Butyl-phenyl)-ethyl]-N-[2-chloro-3-(4-chloro-benzenesulfonyl)-phenyl]-2,3,4-trihydroxy-benzamide ¹H NMR (CD₃COCD₃, 300 MHz) δ (ppm) 11.82 (s, 1H), 9.08 (s, 1H), 8.37 (s, 1H), 7.95 (d, 2H), 7.67-7.15 (m, 10H), 6.74 (s, 1H), 5.94 (s, 1H), 5.64 (s, 1H), 2.94 (s, 4H), 1.29 (s, 9H); ¹³C NMR (CD₃COCD₃) δ (ppm) 168.10, 148.84, 148.45, 147.44, 141.02, 140.32, 139.57, 138.47, 135.03, 131.69, 130.09, 129.29, 128.26, 128.14, 125.25, 123.39, 120.66, 120.52, 117.23, 106.22, 35.20, 34.36, 31.58, 31.37.

TW-24—N-(3-isopropyl-phenyl)-2,3,4-trihydroxy-5-phenethyl-benzamide

¹H NMR (CD₃COCD₃, 300 MHz) δ (ppm) 7.37-7.08 (m, 10H), 6.57 (s, 1H), 5.91 (br, 2H), 3.92-3.78 (m, 5H), 1.31 (d, 6H); ¹³C NMR (CD₃COCD₃) δ (ppm) 168.34, 150.10, 148.11, 146.52, 141.95, 136.64, 131.57, 129.04, 128.90, 128.27, 125.92, 123.30, 119.40, 119.05, 118.54, 117.57, 106.67, 36.17, 34.13, 31.70, 23.93.

TW-25—N-(4-tert-Butyl-benzyl)-2,3,4-trihydroxy-5-phenethyl-benzamide

¹H NMR (CD₃COCD₃, 300 MHz) δ (ppm) 12.66 (s, 1H), 7.46-7.15 (m, 9H), 6.46 (s, 1H), 6.12 (s, 1H), 5.83 (s, 1H), 5.65 (s, 1H), 4.58 (d, 2H), 2.87 (s, 4H), 1.36 (s, 9H); ¹³C NMR (CD₃COCD₃) δ (ppm) 169.77, 150.98, 147.95, 146.01, 141.92, 134.41, 131.42, 128.70, 128.41, 127.81, 125.81, 119.20, 117.30, 106.23, 43.25, 36.23, 24.58, 31.80, 31.33.

TW-26—N-[2-Chloro-3-(4-chloro-benzenesulfonyl)-phenyl]-2,3,4-trihydroxy-5-(4-isopropyl-benzyl)-benzamide ¹H NMR (CD₃COCD₃, 300 MHz) δ (ppm) 11.81 (s, 1H), 9.02 (s, 1H), 8.33 (s, 1H), 7.93 (d, 2H), 7.74-6.95 (m, 8H), 6.55 (s, 1H), 6.08 (s, 1H), 5.60 (s, 1H), 3.97 (s, 2H), 2.96-2.85 (m, 1H), 1.28 (d, 6H).

TW-27

¹H NMR (CD₃COCD₃, 300 MHz) δ (ppm) 11.98 (s, 1H), 7.78 (s, 1H), 7.50-7.18 (m, 8H), 6.52 (s, 1H), 5.99 (s, 1H), 5.74 (s, 1H), 2.93 (s, 4H); ¹³C NMR (CD₃COCD₃) δ (ppm) 168.27, 148.10, 146.82, 141.85, 136.25, 132.91, 131.58, 130.58, 128.93, 128.30, 125.95, 122.44, 121.98, 119.71, 106.17, 36.11, 31.65.

TW-28

¹H NMR (CD₃COCD₃, 300 MHz,) δ (ppm) 10.60 (s, 1H), 7.69 (d, 2H), 7.50 (s, 1H), 7.42-7.09 (m, 8H), 6.59 (s, 1H), 5.91 (s, 1H), 5.68 (s, 1H), 2.95 (s, 4H), 2.28 (s, 3H); ¹³C NMR (CD₃COCD₃) δ (ppm) 168.52, 148.27, 146.42, 141.78, 134.37, 131.60, 131.05, 130.63, 128.77, 128.27, 126.72, 126.28, 125.83, 124.42, 119.43, 117.42, 106.45, 36.00, 31.83, 17.90.

TW-29—N-[4-(4-tert-Butyl-benzenesulfonyl)-3-trifluoromethyl-phenyl]-2,3,4-trihydroxy-5-phenethyl-benzamide ¹H NMR (CD₃COCD₃, 300 MHz) δ (ppm) 11.67 (s, 1H), 8.39 (d, 1H), 8.05 (d, 1H), 7.85 (d, 2H), 7.70 (d, 2H), 7.49 (d, 2H), 7.32-7.17 (m, 6H), 6.62 (s, 1H), 5.96 (s, 1H), 5.64 (s, 1H), 2.92 (s, 4H), 1.33 (s, 9H); ¹³C NMR (CD3COCD3) δ (ppm) 168.59, 157.34, 141.88, 141.75, 138.14, 134.69, 133.93, 131.55, 129.00, 128.29, 127.60, 126.07, 125.92, 122.60, 119.95, 118.10, 105.93, 36.03, 35.31, 31.41, 31.00.

TW-30—N-[4-(4-tert-Butyl-benzenesulfonyl)-3-trifluoromethyl-phenyl]-2,3,4-trihydroxy-5-(4-tert-butyl-phenethyl)-benzamide ¹H NMR (CD₃COCD₃, 300 MHz) δ (ppm) 11.77 (s, 1H), 8.42 (d, 1H), 8.14 (s, 1H), 8.03 (d, 2H), 7.79 (d, 2H), 7.50 (d, 2H), 7.30 (d, 2H), 7.14 (d, 2H), 6.86 (s, 1H), 5.94 (s, 1H), 5.62 (s, 1H), 2.91 (s, 4H), 1.33 (s, 9H), 1.31 (s, 9H); ¹³C NMR (CD3COCD3) δ (ppm) 168.60, 157.31, 148.90, 148.43, 147.30, 141.67, 138.66, 138.17, 134.82, 133.90, 131.64, 128.78, 128.21, 126.06, 125.21, 122.80, 120.59, 117.71, 105.97, 35.54, 35.21, 34.37, 31.78, 31.39, 31.00.

TW-31—N-(3-benzenesulfonyl-phenyl)-2,3-dihydroxy-5-phenethyl-benzamide

¹H NMR (CD₃COCD₃, 300 MHz) δ (ppm) 11.85 (br, 1H), 8.48 (s, 1H), 8.18 (s, 1H), 8.15 (d, 1H), 7.94 (d, 2H), 7.73 (d, 1H), 7.56-7.23 (m, 8H), 7.17 (d, 2H), 6.95 (d, 1H), 6.82 (s, 1H), 2.90-2.80 (m, 4H); ¹³C NMR (CD₃COCD₃) δ (ppm) 169.75, 147.34, 145.59, 142.00, 141.44, 140.90, 138.15, 133.53, 132.67, 130.20, 129.43, 128.75, 128.32, 127.72, 127.57, 126.00, 123.70, 119.67, 119.40, 116.33, 113.47, 37.80, 37.07.

TW-32—N-[(4-Isopropyl-benzenesulfonyl)-phenyl]-N-ethyl-2,3-dihydroxy-5-phenethyl-benzamide ¹H NMR (CD₃COCD₃, 300 MHz) δ (ppm) 10.74 (s, 1H), 7.92 (d, 2H), 7.79 (d, 2H), 7.30-7.18 (m, 7H), 6.93 (d, 2H), 6.61 (d, 2H), 5.86 (d, 2H), 5.69 (s, 1H), 5.32 (s, 1H), 3.96 (q, 2H), 2.88-2.81 (m, 1H), 2.32-2.07 (m, 4H), 1.28-1.18 (m, 9H); ¹³C NMR (CD₃COCD₃) δ (ppm) 171.07, 155.10, 147.85, 146.18, 145.24, 140.99, 140.48, 138.17, 131.42, 128.90, 128.43, 128.31, 137.89, 127.77, 127.50, 125.98, 120.89, 118.06, 115.19, 46.54, 37.58, 37.00, 34.08, 23.50, 14.14.

TW-33—N-[(4-Isopropyl-benzenesulfonyl)-phenyl]-N-ethyl-2,3,4-trihydroxy-5-phenethyl-benzamide ¹H NMR (CD₃COCD₃, 300 MHz) δ (ppm) 11.54 (s, 1H), 7.92 (d, 2H), 7.80 (d, 2H), 7.43-7.16 (m, 8H), 6.98 (d, 2H), 5.81 (s, 1H), 5.63 (s, 1H), 5.46 (s, 1H), 3.94 (q, 2H), 2.95-2.87 (m, 1H), 2.33-2.17 (m, 4H), 1.27-1.18 (m, 9H); ¹³C NMR (CD₃COCD₃) δ (ppm) 171.38, 155.11, 148.24, 147.68, 145.21, 141.53, 140.26, 138.26, 131.29, 128.95, 128.45, 128.26, 127.90, 127.74, 127.51, 125.85, 122.76, 118.36, 46.54, 35.87, 34.09, 31.03, 23.51, 12.81.

TW-34—N-[2-Chloro-5-(4-chloro-benzenesulfonyl)-phenyl]-2,3-dihydroxyl-phenethyl-benzamide ¹H NMR (CD₃COCD₃, 300 MHz) δ (ppm) 11.60 (s, 1H), 9.08 (d, 1H), 8.51 (s, 1H), 7.95 (d, 2H), 7.71 (dd, 1H), 7.62-

7.12 (m, 9H), 7.02 (s, 1H), 6.67 (s, 1H), 5.82 (s, 1H), 2.92 (s, 4H); $^{13}$C NMR (CD$_3$COCD$_3$) δ (ppm) 168.13, 147.60, 145.97, 141.07, 140.96, 140.3, 139.49, 134.80, 132.94, 130.13, 129.83, 129.29, 128.56, 128.51, 128.39, 126.17, 123.74, 120.83, 118.85, 115.63, 113.35, 37.81, 37.25.

TW-35—N-[2-Chloro-5-(4-chloro-benzenesulfonyl)-phenyl]-2,3,4-trihydroxy-5-(2-isopropyl-benzyl)-benzamide $^1$H NMR (CD$_3$COCD$_3$, 300 MHz) δ (ppm) 11.80 (s, 1H), 9.08 (d, 2H), 8.22 (s, 1H), 7.92 (d, 2H), 7.63 (dd, 1H), 7.50-7.11 (m, 8H), 6.35 (s, 1H), 6.06 (s, 1H), 5.70 (s, 1H), 4.03 (s, 2H), 3.02 (m, 1H), 1.17 (d, 6H); $^{13}$C NMR (CD$_3$COCD$_3$) δ (ppm) 167.85, 148.40, 147.55, 146.77, 140.97, 140.47, 139.57, 135.42, 135.03, 131.47, 130.75, 129.89, 129.77, 129.25, 128.09, 127.31, 126.01, 125.74, 123.12, 120.37, 119.83, 116.68, 106.23, 31.61, 28.96, 23.94.

TW-36—N-[4-(4-tert-Butyl-benzenesulfonyl)-3-trifluoromethyl-phenyl]-2,3,4-trihydroxy-5-(2-isopropyl-benzyl)-benzamide $^1$H NMR (CD$_3$COCD$_3$, 300 MHz) δ (ppm) 11.83 (s, 1H), 8.36 (d, 1H), 8.17 (s, 1H), 8.00 (s, 1H), 7.91 (d, 1H), 7.76 (d, 2H), 7.49 (d, 2H), 7.37-7.07 (m, 4H), 6.72 (s, 1H), 6.01 (s, 1H), 5.70 (s, 1H), 4.03 (s, 2H), 3.18 (h, 1H), 1.32 (s, 9H), 0.92 (d, 6H); $^{13}$C NMR (CD$_3$COCD$_3$) δ (ppm) 168.58, 157.29, 148.53, 147.25, 147.10, 141.67, 138.17, 136.14, 134.75, 133.80, 129.70, 127.59, 127.12, 126.04, 125.86, 125.51, 122.75, 119.77, 117.82, 106.31, 35.20, 31.57, 31.00, 28.86, 21.07.

TW-37—N-[(2-tert-Butyl-benzenesulfonyl)-phenyl]-2,3,4-trihydroxy-5-(2-isopropyl-benyl)-benzamide $^1$H NMR (CD$_3$COCD$_3$, 300 MHz) δ (ppm) 12.02 (s, 1H), 7.93 (d, 1H), 7.78 (d, 1H), 7.69-7.03 (m, 9H), 6.59 (s, 1H), 5.95 (s, 1H), 5.63 (s, 1H), 4.04 (s, 2H), 3.17 (h, 1H), 1.57 (s, 9H), 1.22 (d, 6H); $^{13}$C NMR (CD$_3$COCD$_3$) δ (ppm) 168.32, 152.04, 148.48, 147.30, 146.70, 142.30, 142.00, 139.20, 136.02, 133.22, 133.00, 131.63, 129.87, 129.11, 128.44, 127.20, 126.19, 125.90, 120.19, 119.60, 117.17, 106.49, 37.30, 32.19, 31.54, 28.90, 23.82.

TW-38—N-[(2-tert-Butyl-benzenesulfonyl)-phenyl]-2,3,4-trihydroxy-5-(4-tert-butyl-phenethyl)-benzamide $^1$H NMR (CD$_3$COCD$_3$, 300 MHz) δ (ppm) 11.96 (s, 1H), 7.96 (d, 1H), 7.88 (s, 1H), 7.80 (d, 2H), 7.70 (d, 2H), 7.52 (t, 1H), 7.36-7.25 (m, 4H), 7.16 (d, 2H), 6.77 (s, 1H), 5.89 (s, 1H), 5.58 (s, 1H), 2.91 (s, 4H), 1.58 (s, 9H), 1.21 (s, 9H); $^{13}$C NMR (CD$_3$COCD$_3$) δ (ppm) 168.43, 151.14, 148.90, 148.37, 147.20, 141.72, 140.30, 139.60, 139.23, 133.20, 133.00, 132.20, 129.15, 128.48, 128.26, 126.20, 125.23, 120.30, 120.24, 117.20, 106.30, 37.33, 35.56, 35.02, 32.20, 31.74, 31.40.

TW-39—N-[2-Chloro-5-(4-chloro-benzenesulfonyl)-phenyl]-2,3,4-trihydroxy-5-(4-tert-butyl-benzyl)-benzamide $^1$H NMR (CD$_3$COCD$_3$, 300 MHz) δ (ppm) 11.82 (s, 1H), 9.10 (s, 1H), 8.37 (s, 1H), 7.91 (d, 2H), 7.62-7.15 (m, 8H), 6.69 (s, 1H), 5.94 (s, 1H), 5.68 (s, 1H), 3.97 (s, 2H), 1.33 (s, 9H), 1.32 (s, 9H).

TW-40—N-[4-(4-tert-Butyl-benzenesulfonyl)-3-trifluoromethyl-phenyl]-2,3,4-trihydroxy-5-(4-tert-butyl-benzyl)-benzamide $^1$H NMR (CD$_3$COCD$_3$, 300 MHz) δ (ppm) 11.76 (s, 1H), 8.39-7.17 (m, 12H), 7.0 (s, 1H), 5.98 (s, 1H), 3.90 (s, 1H), 3.95 (s, 2H), 1.33 (s, 9H), 1.31 (s, 9H); $^{13}$C NMR (CD$_3$COCD$_3$) δ (ppm) 168.57, 157.32, 149.16, 148.54, 147.30, 141.80, 138.17, 137.00, 134.66, 133.86, 131.74, 129.58, 128.29, 126.07, 125.41, 122.77, 120.08, 118.39, 106.43, 35.21, 34.63, 34.38, 31.36, 31.00, 29.72.

TW-41—N-[4-(2-tert-Butyl-benzenesulfonyl)-phenyl]-2,3,4-trihydroxy-5-(4-tert-butyl-benzyl)-benzamide $^1$H NMR (CD$_3$COCD$_3$, 300 MHz) δ (ppm) 12.02 (s, 1H), 8.10 (s, 1H), 7.95 (d, 1H), 7.72-7.14 (m, 9H), 6.95 (d, 1H), 5.94 (s, 1H), 5.67 (s, 1H), 3.96 (s, 2H), 1.57 (s, 9H), 1.31 (s, 9H); $^{13}$C NMR (CD$_3$COCD$_3$) δ (ppm) 168.44, 151.14, 149.14, 148.56, 140.85, 137.10, 133.20, 133.05, 131.76, 129.16, 128.41, 128.25, 126.21, 125.41, 120.41, 120.35, 119.79, 118.02, 106.46, 37.33, 34.62, 34.40, 32.18, 31.38.

TW-42—N-[4-(2-tert-Butyl-benzenesulfonyl)-phenyl]-2,3,4-trihydroxy-5-(2-iso-hexyl-benzyl)-benzamide $^1$H NMR (CD$_3$COCD$_3$, 300 MHz) δ (ppm) 12.04 (s, 1H), 7.94-7.03 (m, 13H), 6.69 (s, 1H), 5.96 (s, 1H), 5.67 (s, 1H), 4.0 (s, 2H), 2.65-2.61 (m, 2H), 1.56 (s, 9H), 1.61-1.45 (m, 3H), 0.94 (d, 6H); $^{13}$C NMR (CD$_3$COCD$_3$) δ (ppm) 168.41, 151.13, 148.40, 146.88, 141.53, 140.78, 140.00, 138.97, 137.15, 133.20, 133.03, 121.65, 129.59, 129.38, 129.14, 128.32, 126.72, 126.20, 125.95, 120.31, 119.38, 117.58, 40.17, 37.31, 32.17, 31.60, 30.83, 29.71, 28.25.

TW-43—N-[2-Chloro-5-(4-chloro-benzenesulfonyl)-phenyl]-2,3,4-trihydroxy-5-(3-chloro-phenethyl)-benzamide $^1$H NMR (CD$_3$COCD$_3$, 300 MHz) δ (ppm) 11.76 (s, 1H), 9.38 (s, 1H), 8.36 (s, 1H), 7.94 (d, 2H), 7.66-6.0 (m, 8H), 6.67 (s, 1H), 6.28 (s, 1H), 6.12 (s, 1H), 2.90 (s, 4H); $^{13}$C NMR (CD$_3$COCD$_3$) δ (ppm) 168.01, 148.53, 147.42, 143.61, 140.75, 140.29, 139.40, 134.94, 133.97, 131.77, 130.08, 129.76, 129.48, 129.21, 128.60, 128.55, 126.86, 126.13, 123.43, 120.69, 119.77, 117.50, 106.23, 35.36, 31.59.

TW-44

$^1$H NMR (CD$_3$COCD$_3$, 300 MHz) δ (ppm) 9.09 (s, 1H), 8.56 (s, 1H), 7.95 (d, 2H), 7.68-7.50 (m, 4H), 6.85 (s, 1H), 5.6-4.9 (br, 1H), 3.73 (t, 2H), 3.47 (t, 2H), 2.65 (q, 2H), 1.99 (h, 2H), 1.75 (h, 2H), 1.24 (t, 3H); $^{13}$C NMR (CD$_3$COCD$_3$) δ (ppm) 168.16, 148.31, 147.48, 140.87, 140.31, 139.48, 135.13, 131.67, 130.13, 129.80, 129.27, 128.40, 123.36, 122.93, 120.67, 116.27, 106.34, 62.03, 33.67, 31.04, 29.17, 22.80, 14.10.

TW-45—N-[2-Chloro-5-(4-chloro-benzenesulfonyl)-phenyl]-2,3,4-trihydroxy-5-ethyl-benzamide $^1$H NMR (CD$_3$COCD$_3$, 300 MHz) δ (ppm) 11.81 (s, 1H), 9.11 (d, 1H), 8.52 (s, 1H), 7.96 (d, 2H), 7.70-7.51 (m, 4H), 6.88 (s, 1H), 5.96 (s, 1H), 5.72 (s, 1H), 2.69 (q, 2H), 1.25 (t, 3H); $^{13}$C NMR (CD$_3$COCD$_3$) δ (ppm) 168.18, 148.34, 147.19, 141.01, 140.33, 139.55, 135.10, 131.62, 130.12, 129.81, 129.29, 128.28, 123.37, 122.91, 120.65, 116.12, 106.12, 106.33, 22.81, 14.19.

TW-46/51—N-[2-Chloro-5-(4-chloro-benzenesulfonyl)-phenyl]-2,3,4-trihydroxy-benzamide $^1$H NMR (CD$_3$COCD$_3$, 300 MHz) δ (ppm) 12.00 (s, 1H), 9.12 (d, 1H), 8.66 (s, 1H), 7.88-7.42 (m, 6H), 7.08 (d, 1H), 6.61 (d, 1H), 5.88 (s, 1H), 5.68 (s, 1H); $^{13}$C NMR (CD$_3$COCD$_3$) δ (ppm) 168.08, 151.30, 149.82, 142.30, 140.3, 135.4, 133.60, 131.2, 130.2, 129.7, 128.4, 123.6, 121.02, 117.76, 108.03, 106.4.

TW-47—N-[2-Chloro-5-(4-chloro-benzenesulfonyl)-phenyl]-2,3,4-trihydroxy-5-iso-hexyl-benzamide $^1$H NMR (CD$_3$COCD$_3$, 300 MHz) δ (ppm) 11.67 (s, 1H), 9.06 (d, 1H), 8.53 (s, 1H), 7.92 (d, 2H), 7.70-7.26 (m, 4H), 6.86 (s, 1H), 6.19 (s, 1H), 6.09 (s, 1H), 2.57 (t, 2H), 1.61-1.52 (m, 3H), 1.27-1.20 (m, 2H), 0.87 (d, 6H); $^{13}$C NMR (CD$_3$COCD$_3$) δ (ppm) 168.15, 148.20, 147.55, 140.86, 140.32, 139.48, 135.12, 131.16, 130.14, 129.81, 129.28, 128.49, 123.41, 121.66, 120.73, 117.15, 106.15, 38.63, 29.88, 27.90, 27.56, 22.64.

TW-48—N-[(4-Chloro-benzenesulfonyl)-phenyl]-2,3,4-trihydroxy-benzamide $^1$H NMR (CD$_3$COCD$_3$, 300 MHz) δ (ppm) 12.29 (s, 1H), 9.84 (s, 1H), 8.53-7.34 (m, 12H), 6.50 (s, 1H); $^{13}$C NMR (CD$_3$COCD$_3$) δ (ppm) 169.92, 151.81, 150.97, 143.43, 142.91, 140.25, 134.33, 133.54, 130.91, 130.46, 128.45, 126.23, 123.81, 120.48, 119.47, 108.08, 107.96.

TW-49—N-[2-Chloro-5-(4-chloro-benzenesulfonyl)-phenyl]-2,3,4-trihydroxy-5-(2-iso-hexyl-benzyl)-benzamide $^1$H NMR (CD$_3$COCD$_3$, 300 MHz) δ (ppm) 11.79 (s, 1H), 9.09 (s, 1H), 8.25 (s, 1H), 7.93 (d, 2H), 7.68-7.10 (m, 8H), 6.42 (s, 2H), 6.04 (s, 1H), 5.69 (s, 1H), 4.00 (s, 2H), 2.54 (t, 2H), 1.60-1.29 (m, 5H), 0.92 (d, 6H); $^{13}$C NMR (CD$_3$COCD$_3$) δ (ppm) 167.85, 148.36, 146.90, 141.80, 140.98, 140.27, 139.57, 136.54, 135.04, 131.51, 130.56, 129.92, 128.07, 126.91, 126.09, 123.14, 120.08, 119.87, 116.85, 106.37, 40.39, 31.50, 30.70, 28.13, 22.49.

TW-50—4-(2-Iso-propyl-benzyl)-2,3,4-triol $^1$H NMR (CD$_3$COCD$_3$, 300 MHz) δ (ppm) 7.39-7.08 (m, 4H), 6.41-6.30 (m, 2H), 5.31 (s, 1H), 5.16 (s, 1H), 5.08 (s, 1H), 4.0 (s, 2H), 3.14 (h, 1H), 1.21 (d, 6H); $^{13}$C NMR (CD$_3$COCD$_3$) δ (ppm) 147.48, 142.14, 142.01, 136.15, 131.84, 129.58, 127.11, 125.95, 125.66, 120.86, 120.10, 107.44, 32.74, 28.83, 23.68.

TW-52—N-Phenyl-2,3,4-trihydroxy-5-(2-iso-propyl-benzyl)-benzamide $^1$H NMR (CD$_3$COCD$_3$, 300 MHz) δ (ppm) 12.42 (s, 1H), 7.74-7.11 (m, 10H), 6.57 (s, 1H), 5.96 (d, 1H), 5.72 (d, 1H), 4.05 (s, 2H), 3.18 (h, 1H), 1.24 (d, 6H); $^{13}$C NMR (CD$_3$COCD$_3$) δ (ppm) 168.32, 148.40, 147.28, 146.23, 136.53, 136.15, 131.59, 129.91, 129.13, 127.12, 125.88, 125.52, 125.20, 121.15, 119.24, 117.04, 106.83, 31.59, 28.89, 23.83.

TW-53—N-(2-Chloro-phenyl)-2,3,4-trihydroxy-5-(2-iso-propyl-benzyl)-benzamide $^1$H NMR (CD$_3$COCD$_3$, 300 MHz) δ (ppm) 12.19 (s, 1H), 8.40 (dd, 1H), 8.18 (s, 1H), 7.38-7.07 (m, 7H), 6.45 (s, 1H), 6.01 (s, 1H), 5.68 (s, 1H), 4.04 (s, 2H), 3.07 (h, 1H), 1.20 (d, 6H); $^{13}$C NMR (CD$_3$COCD$_3$) δ (ppm) 167.94, 148.33, 147.49, 146.32, 135.58, 133.78, 131.42, 130.66, 129.03, 127.79, 127.28, 125.99, 125.72, 124.93, 123.45, 121.29, 120.04, 116.80, 106.76, 31.65, 28.97, 23.95.

TW-54—N-[2-Methyl-4-(2-tert-butyl-benzenesulfonyl)-phenyl]-2,3,4-trihydroxy-5-(2-iso-propyl-benzyl)-benzamide $^1$H NMR (CD$_3$COCD$_3$, 300 MHz) δ (ppm) 11.98 (s, 1H), 8.25 (d, 1H), 7.87 (d, 1H), 7.67-7.16 (m, 10H), 6.33 (s, 1H), 6.05 (s, 1H), 5.70 (s, 1H), 4.03 (s, 2H), 3.21 (h, 1H), 2.07 (s, 3H), 1.59 (s, 9H), 1.18 (d, 6H); $^{13}$C NMR (CD3COCD3) δ (ppm) 167.95, 151.04, 148.36, 147.57, 146.57, 140.26, 139.12, 138.74, 135.62, 133.04, 132.86, 131.52, 130.70, 129.06, 129.0, 127.33, 126.47, 126.12, 125.94, 125.71, 120.94, 120.17, 116.46, 106.47, 37.28, 32.20, 31.60, 28.93, 23.95, 17.40.

TW-55—N-Methyl-2,3,4-trihydroxy-5-(2-isopropyl-benzyl)-benzamide $^1$H NMR (CD$_3$COCD$_3$, 300 MHz) δ (ppm) 12.83 (s, 1H), 7.35-7.09 (m, 4H), 6.36 (s, 1H), 5.94 (s, 1H), 5.91 (s, 1H), 5.71 (s, 1H), 4.0 (s, 2H), 3.12 (h, 1H), 2.93 (d, 3H), 1.19 (d, 6H); $^{13}$C NMR (CD$_3$COCD$_3$) δ (ppm) 170.56, 148.00, 147.41, 145.63, 136.30, 131.38, 130.15, 127.96, 125.76, 125.52, 118.88, 116.59, 106.59, 31.55, 28.83, 26.26, 23.78.

TW-56—N-(Benzenesulfonyl-phenyl)-2,3,4-trihydroxy-5-benzyl-benzamide $^1$H NMR (CD$_3$COCD$_3$, 300 MHz) δ (ppm) 9.89 (s, 1H), 8.30 (s, 1H), 8.10-6.94 (m, 17H), 3.92 (s, 2H); $^{13}$C NMR (CD$_3$COCD$_3$) δ (ppm) 170.59, 150.82, 149.61, 143.80, 143.40, 142.20, 137.54, 134.07, 130.37, 129.54, 128.99, 128.26, 126.55, 121.88, 121.79, 120.26, 120.13, 36.12.

TW-58—N-[3-Methyl-4-(2-tert-butyl-benzenesulfonyl)-phenyl]-2,3,4-trihydroxy-5-(2-isopropyl-benzyl)-benzamide $^1$H NMR (CD$_3$COCD$_3$, 300 MHz) δ (ppm) 12.01 (s, 1H), 7.97 (d, 1H), 7.88 (s, 1H), 7.70 (d, 1H), 7.42-7.05 (m, 12H), 6.65 (s, 1H), 6.03 (s, 1H), 5.76 (s, 1H), 4.04 (s, 2H), 3.34-3.20 (m, 1H), 2.31 (s, 3H), 1.66 (s, 9H), 1.25 (d, 6H); $^{13}$C NMR (CD$_3$COCD$_3$) δ (ppm) 168.50, 150.59, 148.49, 147.15, 141.03, 141.00, 139.29, 136.51, 132.45, 130.18, 129.83, 129.80, 129.16, 127.06, 126.06, 125.86, 125.52, 123.85, 119.57, 117.51, 117.26, 106.63, 37.32, 31.95, 31.57, 28.48, 23.80, 20.42.

TW-59—N-[3-Chloro-4-(2-tert-butyl-benzenesulfonyl)-phenyl]-2,3,4-trihydroxy-5-(2-isopropyl-benzyl)-benzamide $^1$H NMR (CD$_3$COCD$_3$, 300 MHz) δ (ppm) 12.01 (s, 1H), 8.13 (d, 1H), 8.02 (s, 1H), 7.83 (s, 1H), 7.68-6.92 (m, 7H), 6.68 (s, 1H), 6.03 (s, 1H), 5.73 (s, 1H), 4.04 (s, 2H), 3.19 (h, 1H), 1.66 (s, 9H), 1.25 (d, 6H); $^{13}$C NMR (CD$_3$COCD$_3$) δ (ppm) 168.47, 150.44, 148.47, 147.25, 147.01, 142.09, 140.66, 136.13, 135.47, 133.67, 132.52, 131.60, 130.20, 129.77, 129.00, 127.13, 126.02, 125.87, 125.53, 123.02, 119.75, 117.90, 117.76, 37.17, 31.87, 31.56, 28.87, 23.78.

TW-60—N-[2-Chloro-4-(4-bromo-benzenesulfonyl)-phenyl]-2,3,4-trihydroxy-5-(4-tert-butyl-phenethyl)-benzamide $^1$H NMR (CD$_3$COCD$_3$, 300 MHz) δ (ppm) 11.79 (s, 1H), 9.08 (d, 1H), 8.40 (s, 1H), 7.87 (d, 2H), 7.72-7.08 (m, 9H), 6.76 (s, 1H), 6.09 (s, 1H), 5.86 (s, 1H), 2.93 (s, 4H), 1.32 (s, 9H); $^{13}$C NMR (CD$_3$COCD$_3$) δ (ppm) 168.10, 148.80, 148.41, 147.36, 140.87, 140.05, 138.50, 135.03, 132.80, 131.70, 130.10, 129.32, 128.90, 128.80, 128.35, 128.13, 125.23, 123.40, 120.66, 120.54, 117.30, 106.22, 35.20, 34.34, 31.56, 31.36.

TW-61—N-[2-Chloro-4-(4-bromo-benzenesulfonyl)-phenyl]-2,3,4-trihydroxy-5-(2-isopropyl-benzyl)-benzamide $^1$H NMR (CD$_3$COCD$_3$, 300 MHz) δ (ppm) 11.87 (s, 1H), 9.08 (d, 1H), 8.23 (s, 1H), 7.86-6.36 (m, 10H), 6.35 (s, 1H), 6.18 (s, 1H), 5.88 (s, 1H), 4.02 (s, 2H), 3.02 (h, 1H), 1.21 (d, 6H); $^{13}$C NMR (CD$_3$COCD$_3$) δ (ppm) 167.86, 148.40, 147.53, 146.90, 140.85, 140.05, 135.44, 135.03, 132.75, 131.50, 130.74, 129.90, 127.30, 128.87, 128.16, 127.29, 126.00, 125.73, 123.14, 120.40, 119.81, 116.71, 106.21, 31.60, 28.95, 23.94.

TW-62—N-[4-(3-Methyl-phenylsulfamoyl)-phenyl]-2,3,4-trihydroxy-5-(2-isopropyl-benzyl)-benzamide $^1$H NMR (CD$_3$COCD$_3$, 300 MHz) δ (ppm) 12.01 (s, 1H), 7.73-6.71 (m, 12H), 6.54 (s, 1H), 6.43 (s, 1H), 5.93 (s, 1H), 5.62 (s, 1H), 4.04 (s, 2H), 3.12 (h, 1H), 2.29 (s, 3H), 1.22 (d, 6H); $^{13}$C NMR (CD$_3$COCD$_3$) δ (ppm) 168.31, 149.03, 148.72, 146.02, 141.98, 138.29, 137.57, 137.17, 133.85, 132.40, 128.80, 128.51, 127.54, 126.03, 125.19, 124.62, 124.55, 120.64, 120.28, 118.52, 116.78, 107.00, 31.45, 28.91, 23.39, 20.91.

TW-63—N-[4-(2-tert-Butyl-benzenesulfinyl)-phenyl]-2,3,4-trihydroxy-5-(2-isopropyl-benzyl)-benzamide $^1$H NMR (CD$_3$COCD$_3$, 300 MHz) δ (ppm) 11.86 (s, 1H), 8.37 (s, 1H), 7.71 (d, 1H), 7.62-6.95 (m, 12H), 6.34 (s, 1H), 6.20 (s, 1H), 3.98 (s, 2H), 3.16 (h, 1H), 1.57 (s, 9H), 1.23 (d, 6H); $^{13}$C NMR (CD$_3$COCD$_3$) δ (ppm) 168.26, 148.89, 148.23, 147.13, 146.98, 143.78, 140.29, 139.24, 135.32, 131.78, 131.55, 129.73, 129.60, 127.87, 126.90, 126.64, 126.17, 125.73, 125.34, 121.07, 119.38, 118.27, 107.03, 36.46, 32.78, 31.63, 28.77, 23.71.

TW-64—N-[4-(3-Methyl-phenylsulfamoyl)-phenyl]-2,3,4-trihydroxy-5-benzyl-benzamide $^1$H NMR (CD$_3$COCD$_3$, 300 MHz) δ (ppm) 12.21 (s, 1H), 9.83 (s, 1H), 8.91 (s, 1H), 8.31 (s, 1H), 8.01 (s, 1H), 7.87-6.88 (m, 14H), 3.93 (s, 2H), 2.25 (s, 3H); $^{13}$C NMR (CD$_3$COCD$_3$) δ (ppm) 170.47, 150.76, 149.52, 143.11, 142.23, 139.75, 138.80, 135.75, 133.40, 129.80, 129.28, 128.98, 128.95, 126.54, 126.02, 122.14, 121.44, 120.24, 120.11, 118.59, 107.37, 36.14, 21.41.

TW-65—N-[4-(3-Methyl-phenylsulfamoyl)-phenyl]-2,3,4-trihydroxy-benzamide $^1$H NMR (CD$_3$COCD$_3$, 300 MHz) δ (ppm) 12.16 (s, 1H), 9.77 (s, 1H), 8.90 (s, 1H), 8.48 (s, 1H), 7.91-6.86 (m, 10H), 6.45 (d, 1H), 2.23 (s, 3H); $^{13}$C NMR (CD$_3$COCD$_3$) δ (ppm) 170.23, 152.03, 151.16, 143.18, 139.76, 138.82, 135.73, 133.71, 129.82, 126.02, 122.11, 121.38, 119.54, 118.56, 108.20, 108.02, 21.42.

TW-66—N-[4-(4-Chloro-phenylsulfamoyl)-phenyl]-2,3,4-trihydroxy-benzamide $^1$H NMR (CD$_3$COCD$_3$, 300 MHz) δ (ppm) 12.15 (s, 1H), 9.81 (s, 1H), 9.15 (s, 1H), 8.53 (s, 1H), 7.95-7.25 (m, 9H), 6.47 (d, 1H); $^{13}$C NMR (CD$_3$COCD$_3$) δ (ppm) 170.20, 152.00, 151.15, 143.40, 137.77, 135.17, 133.68, 133.00, 130.15, 129.00, 123.14, 122.51, 121.43, 119.56, 108.19.

TW-68—N-[4-(4-Chloro-benzenesulfonyl)-phenyl]-2,3,4-trihydroxy-benzamide $^1$H NMR (CD$_3$COCD$_3$, 300 MHz) δ (ppm) 12.13 (s, 1H), 9.90 (s, 1H), 8.52 (s, 1H), 8.03-7.91 (m, 7H), 7.68 (d, 2H), 7.46 (d, 1H), 6.49 (d, 1H); $^{13}$C NMR (CD$_3$COCD$_3$) δ (ppm) 170.27, 151.99, 151.22, 144.11, 142.18, 139.90, 136.90, 133.68, 130.57, 130.13, 129.66, 121.85, 119.62, 108.16, 108.06.

TW-69—N-[4-(3-Isopropyl-phenylsulfamoyl)-phenyl]-2,3,4-trihydroxy-benzamide $^1$H NMR (CD$_3$COCD$_3$, 300 MHz) δ (ppm) 12.20 (s, 1H), 9.79 (s, 1H), 8.90 (s, 1H), 8.48 (s, 1H), 8.02-7.70 (m, 5H), 7.45 (d, 1H), 7.17-6.98 (m, 4H), 6.47 (d, 1H), 2.90-2.75 (m, 1H), 1.16 (d, 6H); $^{13}$C NMR (CD$_3$COCD$_3$) δ (ppm) 170.21, 152.02, 151.138, 150.76, 143.17, 138.81, 135.64, 133.69, 129.88, 129.02, 123.44, 121.31, 119.67, 119.57, 119.17, 108.16, 108.06, 34.67, 24.14.

TW-70—N-[4-(2-Isopropyl-phenylsulfamoyl)-phenyl]-2,3,4-trihydroxy-benzamide $^1$H NMR (CD$_3$COCD$_3$, 300 MHz) δ (ppm) 12.25 (s, 1H), 9.84 (s, 1H), 8.50 (s, 1H), 8.42 (s, 1H), 7.94 (d, 2H), 7.86 (s, 1H), 7.71-7.11 (m, 7H), 6.48 (d, 1H), 3.38-3.28 (m, 1H), 1.03 (d, 6H); $^{13}$C NMR (CD$_3$COCD$_3$) δ (ppm) 170.23, 152.06, 151.14, 146.34, 143.06, 136.42, 134.19, 133.71, 129.02, 128.29, 128.13, 127.19, 126.81, 121.34, 119.50, 108.16, 108.02, 27.89, 23.95.

TW-71—N-[4-(3-Isopropyl-phenylsulfamoyl)-phenyl]-2,3,4-trihydroxy-5-benzyl-benzamide $^1$H NMR (CD$_3$COCD$_3$, 300 MHz) δ (ppm) 12.23 (s, 1H), 9.83 (s, 1H), 8.90 (s, 1H), 8.31 (s, 1H), 8.01 (s, 1H), 7.85-7.61 (m, 4H), 7.46 (s, 1H), 7.16-6.98 (m, 8H), 3.93 (s, 2H), 2.90-2.75 (m, 1H), 1.16 (d, 6H); $^{13}$C NMR (CD$_3$COCD$_3$) δ (ppm) 170.48, 150.78, 149.51, 143.10, 142.22, 138.81, 135.67, 133.39, 129.87, 129.27, 128.99, 126.53, 123.44, 121.38, 120.21, 120.09, 119.69, 119.19, 107.33, 36.13, 34.66, 24.24.

TW-73—N-[3-(2-Isopropyl-phenylsulfamoyl)-phenyl]-2,3,4-trihydroxy-benzamide $^1$H NMR (CD$_3$COCD$_3$, 300 MHz) δ (ppm) 12.37 (s, 1H), 9.79 (s, 1H), 8.57 (s, 1H), 8.45 (s, 1H), 8.25 (s, 1H), 8.24 (d, 1H), 7.54 (s, 1H), 7.52-7.10 (m, 7H), 6.47 (d, 1H), 2.94 (h, 1H), 1.02 (d, 6H).

TW-74—N-[3-(3-Isopropyl-phenylsulfamoyl)-phenyl]-2,3,4-trihydroxy-benzamide

¹H NMR (CD₃COCD₃, 300 MHz) δ (ppm) 12.33 (s, 1H), 9.77 (s, 1H), 9.02 (s, 1H), 8.41-6.90 (m, 11H), 6.43 (d, 1H), 2.82 (h, 1H), 1.15 (d, 6H); ¹³C NMR (CD₃COCD₃) δ (ppm) 170.23, 152.12, 151.05, 150.78, 141.47, 139.82, 138.64, 133.71, 130.22, 129.89, 125.60, 123.56, 123.41, 120.36, 119.84, 119.40, 119.32, 108.04, 107.97, 34.68, 24.12.

TW-75—N-[4-(3-Isopropyl-phenylsulfamoyl)-phenyl]-2,3,4-trihydroxy-5-(2-isopropyl-benzyl)-benzamide ¹H NMR (CD₃COCD₃, 300 MHz) δ (ppm) 12.17 (s, 1H), 9.79 (s, 1H), 8.88 (s, 1H), 8.31 (s, 1H), 8.01 (s, 1H), 7.84-7.74 (m, 4H), 7.31-6.93 (m, 10H), 4.0 (s, 2H), 3.36 (h, 1H), 2.79 (h, 1H), 1.21 (d, 6H), 0.89 (d, 6H); ¹³C NMR (CD₃COCD₃) δ (ppm) 170.41, 150.76, 149.10, 147.38, 143.09, 138.81, 138.18, 135.67, 129.86, 129.82, 128.98, 127.19, 126.29, 125.70, 123.44, 121.39, 120.39, 119.70, 119.20, 108.41, 34.66, 32.47, 32.18, 24.13, 23.93.

TW-76—N-[4-(2-Isopropyl-phenylsulfamoyl)-phenyl]-2,3,4-trihydroxy-5-(2-isopropyl-benzyl)-benzamide ¹H NMR (CD₃COCD₃, 300 MHz) δ (ppm) 12.08 (s, 1H), 7.89 (s, 1H), 7.69-7.57 (m, 4H), 7.39-7.06 (m, 8H), 6.61 (s, 1H), 6.47 (s, 1H), 6.04 (s, 1H), 5.78 (s, 1H), 4.04 (s, 2H), 3.36 (h, 1H), 2.82 (h, 1H), 1.21 (d, 6H), 1.02 (d, 6H); ¹³C NMR (CD₃COCD₃) δ (ppm) 168.74, 148.84, 147.67, 147.13, 143.18, 141.46, 136.49, 135.08, 132.74, 131.96, 130.19, 128.88, 127.53, 127.49, 126.84, 126.52, 126.20, 125.88, 125.85, 120.42, 119.90, 117.69, 106.88, 31.86, 29.21, 27.79, 24.11, 23.57.

TW-78—N-[4-(−2-tert-Butyl-benzenesulfonyl)-phenyl]-5-naphthalen-1-ylmethyl-benzamide ¹H NMR (CD₃COCD₃, 300 MHz) δ (ppm) 12.21 (s, 1H), 9.87 (s, 1H), 8.46 (s, 1H), 8.24 (d, 1H), 8.08 (s, 1H), 7.95-7.15 (m, 15H), 4.42 (s, 2H), 1.57 (s, 9H); ¹³C NMR (CD₃COCD₃) δ (ppm) 168.41, 151.27, 150.72, 149.64, 143.25, 141.83, 139.36, 137.70, 134.77, 134.03, 133.89, 133.46, 132.97, 129.98, 129.45, 128.93, 127.51, 127.31, 126.77, 126.42, 124.66, 121.61, 120.56, 119.08, 107.65, 37.83, 32.51.

TW-79—N-[2-Methyl-5-(3-isopropyl-phenylsulfamoyl)-phenyl]-2,3,4-trihydroxy-5-(2-isopropyl-benzyl)-benzamide ¹H NMR (CD₃COCD₃, 300 MHz) δ (ppm) 12.10 (s, 1H), 8.51 (s, 1H), 7.50-6.71 (m, 16H), 6.35 (s, 1H), 6.16 (s, 1H), 6.03 (s, 1H), 4.03 (s, 2H), 3.06 (h, 1H), 2.81 (h, 1H), 2.07 (s, 3H), 1.19 (d, 6H), 1.13 (g, 6H); ¹³C NMR (CD₃COCD₃) δ (ppm) 167.97, 150.34, 148.36, 147.56, 146.67, 136.21, 135.80, 135.64, 133.76, 131.59, 130.78, 130.61, 129.15, 127.24, 125.91, 125.65, 123.83, 123.62, 120.73, 120.06, 120.00, 119.24, 116.57, 106.41, 33.88, 31.62, 28.91, 23.93, 23.91, 17.57.

TW-80—N-[2-Methyl-5-(4-chloro-phenylsulfamoyl)-phenyl]-2,3,4-trihydroxy-5-(2-isopropyl-benzyl)-benzamide ¹H NMR (CD₃COCD₃, 300 MHz) δ (ppm) 12.04 (s, 1H), 9.31 (s, 1H), 9.22 (s, 1H), 8.33 (s, 1H), 8.12 (s, 1H), 8.00 (s, 1H), 7.53 (d, 1H), 7.41-7.08 (m, 9H), 4.03 (s, 2H), 3.28 (h, 1H), 2.28 (s, 3H), 1.21 (d, 6H); ¹³C NMR (CD₃COCD₃) δ (ppm) 169.58, 150.03, 149.18, 147.71, 138.68, 138.55, 137.88, 137.73, 137.46, 133.25, 131.88, 130.08, 130.00, 127.43, 126.40, 125.96, 124.91, 124.39, 123.04, 121.49, 120.28, 120.02, 107.66, 32.61, 24.06, 23.29, 18.21.

TW-81—N-[4-(2-Isopropyl-phenylsulfamoyl)-phenyl]-2,3,4-trihydroxy-5-naphthalen-1-ylmethyl-benzamide ¹H NMR (CD₃COCD₃, 300 MHz) δ (ppm) 12.27 (s, 1H), 9.73 (s, 1H), 8.44 (s, 1H), 8.37 (s, 1H), 8.25 (d, 1H), 8.08 (s, 1H), 7.93 (s, 1H), 7.83-7.08 (m, 14H), 4.42 (s, 2H), 3.376 (h, 1H), 1.01 (d, 6H); ¹³C NMR (CD₃COCD₃) δ (ppm) 168.62, 150.73, 149.58, 146.33, 142.93, 137.72, 136.43, 134.76, 134.16, 133.45, 132.97, 129.44, 128.96, 128.28, 128.12, 127.82, 127.49, 127.17, 126.77, 126.41, 126.39, 121.65, 121.41, 121.31, 120.50, 119.05, 107.64, 32.53, 27.87, 23.93.

TW-82—N-Phenyl-2,3,4-trihydroxy-5-benzyl-benzamide

¹H NMR (CD₃COCD₃, 300 MHz) δ (ppm) 12.61 (s, 1H), 9.58 (s, 1H), 8.17 (s, 1H), 7.92 (s, 1H), 7.71 (d, 2H), 7.48 (s, 1H), 7.39-7.13 (m, 8H), 3.95 (s, 2H); ¹³C NMR (CD₃COCD₃) δ (ppm) 170.30, 150.79, 149.00, 142.38, 139.02, 133.38, 129.50, 129.30, 128.97, 126.50, 125.19, 122.27, 119.89, 119.82, 107.58, 36.17.

TW-83—N-[2-Chloro-5-(4-chloro-benzenesulfonyl)-phenyl]-2,3,4-trihydroxy-5-naphthalen-1-ylmethyl-benzamide ¹H NMR (CD₃COCD₃, 300 MHz) δ (ppm) 11.25 (s, 1H), 9.58 (s, 1H), 8.84 (s, 1H), 8.66 (s, 1H), 8.15-7.16 (m, 16H), 4.43 (s, 2H); ¹³C NMR (CD₃COCD₃) δ (ppm) 168.49, 149.37, 148.95, 141.68, 141.21, 140.42, 137.31, 136.95, 136.87, 134.94, 133.32, 133.08, 131.47, 130.74, 130.39, 129.48, 127.80, 127.75, 126.83, 126.51, 126.46, 124.99, 124.88, 123.24, 123.06, 121.10, 120.34, 108.57, 32.54.

TW-85—N-(3-Benzenesulfonyl)-phenyl-2,3,4-trihydroxy-5-(2-isopropyl-benzyl)-benzamide ¹H NMR (CD₃COCD₃, 300 MHz) δ (ppm) 12.29 (s, 1H), 9.85 (s, 1H), 8.33 (s, 1H), 8.32 (s, 1H), 8.05-6.98 (m, 14H), 4.02 (s, 2H), 3.39-3.30 (m, 1H), 1.22 (d, 6H); ¹³C NMR (CD₃COCD₃) δ (ppm) 170.48, 150.65, 149.45, 147.38, 143.34, 142.80, 140.15, 138.19, 134.30, 133.33, 130.84, 130.41, 129.82, 128.40, 127.18, 126.50, 126.28, 125.69, 123.83, 120.65, 120.22, 119.70, 107.36, 32.47, 23.92, 14.48.

TW-86—N-[2-Ethyl-5-(2-isopropyl-phenylsulfamoyl)-phenyl]-2,3,4-trihydroxy-5-(2-isopropyl-benzyl)-benzamide ¹H NMR (CD₃COCD₃, 300 MHz) δ (ppm) 12.13 (s, 1H), 8.53 (s, 1H), 7.52 (s, 1H), 7.45-6.96 (m, 11H), 6.72 (s, 1H), 6.24 (s 3H), 4.04 (s, 2H), 3.21-3.17 (m, 2H), 2.40 (s, 3H), 1.20-0.94 (m, 15H); ¹³C NMR (CD₃COCD₃) δ (ppm) 168.08, 148.41, 147.65, 146.78, 142.97, 139.33, 137.75, 135.72, 135.02, 132.50, 131.66, 130.80, 128.88, 127.28, 127.04, 126.45, 126.07, 125.91, 125.68, 124.11, 121.29, 120.14, 116.25, 106.38, 31.64, 28.92, 27.37, 24.29, 23.95, 23.22, 13.31.

TW-87—N-[2-Ethyl-(4-chloro-benzenesulfonyl)-phenyl]-2,3,4-trihydroxy-5-(2-isopropyl-benzyl)-benzamide ¹H NMR (CD₃COCD₃, 300 MHz) δ (ppm) 12.09 (s, 1H), 8.64 (s, 1H), 7.92 (d, 2H), 7.68 (d, 1H), 7.50-7.18 (m, 10H), 6.29 (s, 1H), 6.01 (s, 1H), 5.67 (s, 1H), 4.04 (s, 2H), 3.25 (h, 1H), 2.72 (q, 2H), 1.21 (d, 6H), 1.06 (t, 3H); ¹³C NMR (CD₃COCD₃) δ (ppm) 168.04, 148.41, 147.65, 146.36, 140.13, 139.86, 139.65, 135.58, 135.35, 131.53, 130.79, 129.61, 129.55, 129.14, 127.33, 125.91, 125.73, 124.05, 121.58, 120.06, 116.07, 106.29, 31.62, 28.93, 24.29, 23.93, 13.18.

TW-88—N-[2-Ethyl-5-(4-chloro-phenylsulfamoyl)-phenyl]-2,3,4-trihydroxy-5-(2-isopropyl-benzyl)-benzamide ¹H NMR (CD₃COCD₃, 300 MHz) δ (ppm) 12.13 (s, 1H), 8.56 (s, 1H), 7.65-7.05 (m, 13H), 6.31 (s, 1H), 6.22 (s, 1H), 6.11 (s, 1H), 4.03 (s, 2H), 3.03 (h, 1H), 2.72 (q, 2H), 1.20 (d, 6H), 1.06 (t, 3H); ¹³C NMR (CD₃COCD₃) δ (ppm) 168.10, 148.34, 147.63, 146.75, 139.29, 136.98, 135.62, 135.09, 134.90, 131.60, 131.02, 130.77, 129.40, 128.95, 127.30, 125.91, 125.71, 123.94, 123.26, 120.91, 120.21, 116.26, 106.35, 31.62, 30.96, 24.16, 13.08.

TW-89—N-[4-(Pyridine-2-sulfonyl)-phenyl]-2,3,4-trihydroxy-5-benzyl-benzamide ¹H NMR (CD₃COCD₃, 300 MHz) δ (ppm) 12.19 (s, 1H), 9.94 (s, 1H), 8.68 (d, 1H), 8.34-7.15 (m, 15H), 3.94 (s, 2H); ¹³C NMR (CD₃COCD₃) δ (ppm) 170.62, 151.32, 150.83, 149.64, 144.28, 142.23, 139.50, 134.80, 133.43, 130.82, 129.28, 128.99, 128.10, 126.56, 122.54, 121.58, 121.48, 120.31, 120.16, 107.37, 36.14.

TW-90—N-[4-(2-tert-Butylbenzenesulfonyl)-phenyl]-2,3,4-trihydroxy-5-naphthalen-2-yl-benzamide ¹H NMR (CD₃COCD₃, 300 MHz) δ (ppm) 12.38 (s, 1H), 10.08 (s, 1H), 8.37 (s, 1H), 8.28 (s, 1H), 8.08-7.53 (m, 17H), 1.58 (s, 9H); ¹³C NMR (CD₃COCD₃) δ (ppm) 170.61, 151.44, 151.30, 148.96, 143.28, 141.80, 139.49, 134.42, 134.14, 134.04, 133.91, 133.71, 129.99, 128.97, 128.80, 128.54, 128.06, 127.31, 126.90, 126.64, 121.67, 121.58, 121.44, 120.56, 108.05, 37.84, 32.51.

TW-91—N-[2-Chloro-5-(4-chloro-benzenesulfonyl)-phenyl]-2,3,4-trihydroxy-5-naphthalen-2-yl-benzamide ¹H NMR (CD₃COCD₃, 300 MHz) δ (ppm) 11.54 (s, 1H), 10.14 (s, 1H), 8.82 (s, 1H), 8.53 (s, 1H), 8.29 (s, 1H), 8.11-7.49 (m, 14H); ¹³C NMR (CD₃COCD₃) δ (ppm) 168.41, 150.02, 149.09, 141.70, 141.23, 140.50, 137.04, 136.31, 134.46, 133.80, 133.37, 133.04, 131.75, 130.79, 130.45, 128.88, 128.69, 128.61, 128.41, 128.29, 126.93, 126.69, 125.70, 125.10, 122.11, 121.89, 109.11.

TW-92—N-[4-(2-tert-Butyl-benzenesulfonyl)-phenyl]-2,3,4-trihydroxy-5-naphthalen-2-ylmethyl-benzamide ¹H NMR (CD₃COCD₃, 300 MHz) δ (ppm) 12.28 (s, 1H), 9.91 (s, 1H), 8.47-7.27 (m, 18H), 4.32-4.13 (m, 2H), 1.57 (s, 9H); ¹³C NMR (CD₃COCD₃) δ (ppm) 170.52, 151.28, 151.11, 149.85, 143.22, 141.81, 139.40, 139.26, 134.33, 134.02, 133.90, 133.55, 129.98, 129.11, 128.79, 128.52, 127.60, 126.64, 121.65, 120.68, 120.42, 118.40, 107.64, 107.46, 37.83, 37.41, 32.51.

TW-94

¹H NMR (CD₃COCD₃, 300 MHz) δ (ppm) 11.88 (s, 1H), 8.68 (d, 1H), 8.21-8.16 (m, 2H), 7.97-7.25 (m, 10H), 6.87 (s, 1H), 6.10 (s, 1H), 5.82 (s, 1H), 3.97 (s, 2H), 2.23 (s, 3H); ¹³C NMR (CD₃COCD₃) δ (ppm) 168.50, 159.19, 150.88, 148.87, 147.31, 140.59, 140.04, 138.59, 134.58, 132.10, 131.46, 129.53, 129.41, 129.00, 128.45, 127.32, 126.80, 122.54, 120.53, 117.83, 107.05, 35.40, 17.97.

TW-95A

¹H NMR (CD₃COCD₃, 300 MHz) δ (ppm) 10.19 (s, 1H), 8.62-7.25 (m, 19H), 4.43 (s, 2H), 4.04 (s, 3H), 3.95 (s, 3H), 3.89 (s, 3H); ¹³C NMR (CD₃COCD₃) δ (ppm) 167.77, 162.97, 155.81, 151.00, 145.79, 143.35, 142.45, 142.21, 135.88, 135.76, 135.09, 134.46, 134.19, 130.83, 129.32, 129.22, 128.84, 128.74, 127.42, 127.34, 127.20, 127.15, 126.90, 125.96, 125.54, 125.52, 125.37, 125.32, 124.26, 124.01, 123.79, 120.19, 119.84, 62.52, 61.38, 61.33, 32.95.

TW-95

¹H NMR (CD₃COCD₃, 300 MHz) δ (ppm) 12.06 (s, 1H), 9.83 (s, 1H), 8.83-7.33 (m, 23H), 4.22 (s, 2H); ¹³C NMR (CD₃COCD₃) δ (ppm) 174.2, 172.1, 150.65, 144.27, 143.32, 137.68, 136.75, 136.33, 135.22, 134.76, 133.47, 132.95, 131.46, 130.29, 129.89, 129.78, 129.69, 129.47, 129.344, 129.04, 128.95, 128.06, 127.49, 126.81, 126.76, 126.40, 126.30, 126.18, 125.60, 124.79, 124.67, 121.76, 120.63, 119.17, 32.51.

TW-98

¹H NMR (CD₃COCD₃, 300 MHz) δ (ppm) 12.42 (s, 1H), 10.01 (s, 1H), 8.37-7.40 (m, 17H), 1.57 (s, 9H); ¹³C NMR (CD₃COCD₃) δ (ppm) 170.09, 151.20, 150.80, 148.96, 142.87, 138.90, 136.49, 134.11, 133.57, 133.44, 133.14, 132.94, 129.50, 128.44, 128.20, 128.06, 126.83, 126.20, 126.08, 125.80, 121.08, 120.63, 119.88, 107.14, 37.33.

TW-100

¹H NMR (CD₃COCD₃, 300 MHz) δ (ppm) 12.11 (s, 1H), 8.15 (s, 1H), 7.98 (s, 1H), 7.95 (s, 1H), 7.78-7.12 (m, 14H), 6.36 (s, 1H), 5.74 (s, 1H), 1.56 (s, 9H); ¹³C NMR (CD₃COCD₃) δ (ppm) 170.373, 151.65, 151.33, 143.16, 141.79, 141.21, 140.51, 140.30, 139.70, 134.07, 133.94, 130.16, 128.97, 127.33, 125.19, 124.90, 124.08, 122.60, 122.50, 121.93, 121.84, 119.29, 114.51, 108.43, 79.20, 37.85, 32.52.

TW-108

¹H NMR (CD₃COCD₃, 300 MHz) δ (ppm) 12.18 (s, 1H), 10.33 (s, 1H), 8.31-7.43 (m, 17H), 1.60 (s, 9H); ¹³C NMR (CD₃COCD₃) δ (ppm) 151.36, 143.03, 138.32, 134.74, 134.10, 133.98, 133.49, 132.71, 130.03, 129.32, 129.03, 128.97, 128.47, 127.34, 127.29, 126.81, 125.97, 125.89, 121.95, 121.85, 119.14, 117.39, 37.87, 32.52.

TW-109

¹H NMR (CD₃COCD₃, 300 MHz) δ (ppm) 11.71 (s, 1H), 10.09 (s, 1H), 8.76 (s, 1H), 8.56 (s, 1H), 8.08 (s, 1H), 8.20-

7.54 (m, 24H); $^{13}$C NMR (CD$_3$COCD$_3$) δ (ppm) 152.3, 148.90, 141.71, 141.23, 140.52, 134.97, 132.43, 131.81, 130.80, 130.56, 130.47, 130.11, 129.28, 128.57, 127.76, 127.03, 126.76, 126.53, 126.42, 121.42, 108.79.

TW-115

$^1$H NMR (CD$_3$COCD$_3$, 300 MHz) δ (ppm) 12.44 (s, 1H), 10.60 (s, 1H), 9.40 (s, 1H), 8.35 (s, 1H), 8.32-7.44 (m, 15H); $^{13}$C NMR (CD$_3$COCD$_3$) δ (ppm) 170.19, 151.67, 141.38, 138.30, 137.84, 137.21, 135.52, 133.94, 133.48, 132.85, 131.68, 128.85, 128.54, 128.26, 127.17, 126.70, 126.30, 124.07, 123.15, 122.91, 121.50, 120.23, 114.53, 107.17.

TW-121

$^1$H NMR (CDCl$_3$, 300 MHz) δ (ppm) 12.44 (s, 1H), 10.21 (s, 1H), 9.02 (s, 1H), 8.40 (d, 2H), 7.94-7.0 (m, 14H), 3.30 (hex, 1H), 0.95 (d, 6H); $^{13}$C NMR (CDCl$_3$) δ (ppm) 170.30, 151.69, 148.57, 146.37, 142.82, 141.12, 140.23, 136.77, 134.19, 129.05, 128.31, 128.26, 128.17, 127.22, 126.83, 125.18, 124.90, 124.09, 122.61, 122.48, 121.76, 119.21, 114.50, 108.41, 27.91, 23.97.

TW-127

$^1$H NMR (CDCl$_3$, 300 MHz) δ (ppm) 12.10 (s, 1H), 8.06 (s, 1H), 7.81-6.61 (m, 13H), 7.07 (s, 1H), 6.06 (s, 1H), 5.77 (s, 1H), 4.20-4.07 (m, 1H), 4.04 (s, 2H), 3.54 (s, 3H), 3.10-2.95 (m, 1H), 3.05 (q, 2H), 1.23 (d, 6H); $^{13}$C NMR (CDCl$_3$) δ (ppm) 172.18, 169.23, 149.23, 147.95, 147.81, 141.80, 137.00, 135.60, 135.36, 132.38, 130.47, 130.09, 129.34, 129.02, 128.04, 127.80, 126.59, 126.21, 121.08, 120.36, 118.60, 107.37, 61.27, 57.45, 53.35, 40.03, 32.16, 29.60, 23.32.

TW-130

$^1$H NMR (CDCl$_3$, 300 MHz) δ (ppm) 12.41 (s, 1H), 7.15-7.02 (m, 8H), 6.35 (d, 2H), 6.17 (s, 1H), 6.00 (s, 1H), 5.32 (s, 1H), 4.94-4.83 (m, 1H), 4.07-3.94 (m, 2H), 3.43 (s, 1H), 3.20-3.08 (m, 2H); $^{13}$C NMR (CDCl$_3$) δ (ppm) 172.44, 170.25, 148.76, 147.88, 147.02, 136.89, 136.09, 132.05, 130.62, 130.01, 129.74, 129.45, 127.95, 127.61, 126.41, 126.08, 119.88, 117.94, 106.83, 53.80, 53.24, 38.48, 32.29, 29.50, 24.46.

TW-132

$^1$H NMR (CDCl$_3$, 300 MHz) δ (ppm) 12.10 (s, 1H), 8.22 (s, 1H), 7.86-7.05 (m, 8H), 6.68 (s, 1H), 6.21 (s, 1H), 6.01 (s, 1H), 5.27 (d, 1H), 4.03 (s, 2H), 3.95-3.87 (m, 1H), 3.38 (s, 1H), 3.20-3.14 (m, 1H), 1.75-1.68 (m, 2H), 1.26 (d, 6H).

TW-133

$^1$H NMR (CD$_3$COCD$_3$, 300 MHz,) δ (ppm) 12.25 (s, 1H), 9.83 (s, 1H), 8.51 (s, 1H), 8.33 (s, 1H), 7.83-6.98 (m, 15H), 5.14-5.09 (t, 1H), 4.02 (s, 2H), 3.53 (s, 3H), 3.32-3.28 (m, 1H), 1.31 (d, 6H); $^{13}$C NMR (CD$_3$COCD$_3$) δ (ppm) 170.57, 169.96, 150.15, 149.05, 146.92, 142.35, 137.73, 136.46, 136.31, 132.87, 129.34, 129.03, 128.73, 128.31, 127.69, 126.72, 125.83, 125.23, 120.94, 120.84, 119.90, 119.25, 107.06, 60.17, 60.06, 52.37, 32.00, 23.46.

TW-134

$^1$H NMR (CDCl$_3$, 300 MHz) δ (ppm) 12.01 (s, 1H), 7.89-7.23 (m, 13H), 6.86 (s, 1H), 6.50 (s, 1H), 5.45 (s, 1H), 4.01 (s, 2H), 1.56 (s, 9H); $^{13}$C NMR (CDCl$_3$) δ (ppm) 168.37, 151.13, 148.61, 146.90, 140.70, 140.06, 139.09, 133.20, 133.01, 131.78, 129.13, 128.65, 128.51, 128.40, 126.30, 126.19, 120.33, 119.63, 117.81, 106.59, 37.31, 35.12, 32.17.

TW-137

$^1$H NMR (CDCl$_3$, 300 MHz) δ (ppm) 12.06 (s, 1H), 7.87-7.06 (m, 9H), 6.83 (s, 1H), 6.08 (s, 1H), 5.81 (s, 1H), 5.32-5.27 (m, 1H), 4.04 (s, 2H), 3.95-3.78 (m, 1H), 3.70-3.54 (m, 2H), 3.5 (s, 3H), 3.20-3.15 (m, 2H), 1.76-1.56 (m, 1H), 1.00-0.87 (m, 12H); $^{13}$C NMR (CDCl$_3$) δ (ppm) 171.83, 168.37, 148.48, 147.21, 146.85, 140.95, 136.10, 134.88, 131.64, 129.74, 128.52, 127.12, 125.86, 125.51, 120.18, 119.60, 117.42, 106.53, 61.06, 52.40, 31.57, 28.86, 23.77, 22.63, 18.93, 17.32, 14.11.

TW-138

$^1$H NMR (CDCl$_3$, 300 MHz) δ (ppm) 12.30 (s, 1H), 10.61 (s, 1H), 9.61 (s, 1H), 8.39-7.55 (m, 14H); $^{13}$C NMR (CDCl$_3$) δ (ppm) 170.17, 138.34, 137.85, 136.52, 135.71, 133.83, 133.79, 132.61, 131.70, 131.11, 128.92, 128.73, 128.31, 128.26, 127.86, 127.30, 126.93, 126.62, 125.77, 124.12, 123.18, 122.93, 121.18, 120.98, 114.65.

TW-141

$^1$H NMR (CD$_3$COCD$_3$, 300 MHz,) δ (ppm) 12.74 (s, 1H), 10.50 (s, 1H), 9.75 (s, 1H), 9.30 (s, 1H), 8.52-7.14 (m, 13H), 4.42 (s, 2H), 3.57 (t, 2H), 2.91 (s, 2H), 1.66 (s, 9H).

TW-142

$^1$H NMR (CD$_3$COCD$_3$, 300 MHz,) δ (ppm) 11.98 (s, 1H), 8.16 (s, 1H), 8.00-6.34 (m, 16H), 4.04 (s, 2H), 3.87-3.67 (m, 1H), 2.96-2.74 (m, 1H), 2.70 (s, 3H), 1.21 (d, 6H); $^{13}$C NMR (CD$_3$COCD$_3$) δ (ppm) 208.07, 171.70, 171.60, 168.89, 149.03, 147.76, 147.62, 141.92, 136.71, 135.57, 133.80, 132.17, 130.09, 129.40, 129.37, 128.69, 127.76, 127.45, 126.23, 125.87, 120.77, 119.97, 118.47, 107.18, 60.68, 58.46, 38.90, 32.06, 30.11, 28.86, 24.20, 21.48, 14.60.

TW-144

$^1$H NMR (CD$_3$COCD$_3$, 300 MHz,) δ (ppm) 12.07 (s, 1H), 7.88 (s, 1H), 7.70 (d, 2H), 7.57 (d, 2H), 7.39-7.07 (m, 11H), 6.62 (s, 1H), 6.11 (s, 1H), 5.85 (s, 1H), 4.04 (s, 2H), 3.54 (s, 4H), 3.10-2.87 (m, 2H), 0.91 (d, 6H); $^{13}$C NMR (CD$_3$COCD$_3$) δ (ppm) 171.30, 168.43, 148.51, 147.32, 146.90, 141.00, 136.17, 134.83, 131.64, 129.86, 129.38, 128.62, 128.37, 127.32, 127.16, 125.88, 125.55, 120.27, 119.61, 117.44, 106.55, 56.64, 53.44, 39.34, 31.59, 28.89, 23.80, 22.66, 14.14.

TW-147

$^1$H NMR (CD$_3$COCD$_3$, 300 MHz,) δ (ppm) 12.02 (s, 1H), 8.20-6.80 (m, 15H), 4.01 (s, 3H).

TW-148

$^1$H NMR (CD$_3$COCD$_3$, 300 MHz,) δ (ppm) 11.67 (s, 1H), 9.31 (s, 1H), 7.98-7.05 (m, 15H), 3.96 (s, 2H), 3.76-3.64 (m, 2H), 2.48 (d, 2H), 2.21 (t, 2H), 1.57 (s, 9H), 1.31-1.22 (m, 4H); $^{13}$C NMR (CD$_3$COCD$_3$) δ (ppm) 166.61, 154.04, 151.14, 149.04, 140.68, 139.98, 139.61, 139.55, 133.26, 129.15, 128.98, 128.30, 128.255, 128.17, 126.30, 126.12, 121.68, 121.30, 119.51, 115.10, 112.80, 56.71, 46.58, 42.48, 37.20, 32.20, 31.60, 22.66, 14.13.

TW-159

$^1$H NMR (CD$_3$COCD$_3$, 300 MHz,) δ (ppm) 12.84 (s, 1H), 9.08 (s, 1H), 7.97-7.05 (m, 15H), 6.23 (s, 1H), 5.23 (s, 1H), 2.94 (t, 2H), 2.58 (t, 2H), 1.75-1.63 (m, 2H), 1.67 (s, 9H).

TW-160

$^1$H NMR (CD$_3$COCD$_3$, 300 MHz,) δ (ppm) 10.6 (s, 1H), 8.07-7.10 (m, 16H), 2.92 (t, 2H), 2.56 (t, 2H), 1.58 (s, 9H), 1.57-1.45 (m, 4H).

TW-161

$^1$H NMR (CD$_3$COCD$_3$, 300 MHz,) δ (ppm) 12.58 (s, 1H), 10.64 (s, 1H), 8.73 (s, 1H), 8.05-6.83 (m, 16H), 3.18 (t, 2H), 2.87 (t, 2H), 1.57 (s, 9H), 1.54-1.34 (m, 2H); $^{13}$C NMR (CD$_3$COCD$_3$) δ (ppm) 167.94, 150.35, 146.39, 141.66, 140.62, 139.18, 138.64, 133.13, 132.99, 131.02, 129.01, 128.58, 128.27, 128.18, 128.04, 127.96, 126.34, 126.12, 120.98, 119.14, 117.61, 116.50, 114.71, 67.28, 44.30, 34.90, 29.59.

TW-164

$^1$H NMR (CD$_3$COCD$_3$, 300 MHz,) δ (ppm) 10.76 (s, 1H), 8.40 (s, 1H), 7.95 (s, 1H), 7.60-7.12 (m, 10H), 4.19 (s, 2H), 3.68-3.72 (m, 6H), 2.95-2.76 (m, 6H); $^{13}$C NMR (CD$_3$COCD$_3$) δ (ppm) 165.13, 147.75, 137.84, 136.46, 133.85, 133.15, 132.47, 129.54, 127.52, 127.36, 126.97, 124.74, 122.40, 120.99, 119.45, 116.73, 66.14, 55.79, 48.12, 46.78, 44.48, 28.89, 18.95.

TW-166

$^1$H NMR (CD$_3$COCD$_3$, 300 MHz,) δ (ppm) 7.99-7.15 (m, 22H), 3.63 (t, 2H), 2.93 (t, 2H).

TW-167

$^1$H NMR (CD$_3$COCD$_3$, 300 MHz,) δ (ppm) 8.31 (s, 1H), 7.84-6.93 (m, 17H), 3.30-3.24 (m, 8H), 2.89 (s, 4H), 1.31 (s, 9H); $^{13}$C NMR (CD$_3$COCD$_3$) δ (ppm) 168.96, 151.02, 149.44, 147.81, 146.24, 141.62, 138.61, 133.50, 131.41, 129.67, 129.50, 129.16, 128.58, 125.70, 121.33, 121.13, 120.09, 117.38, 116.58, 114.10, 49.56, 46.49, 37.70, 34.81, 31.81, 25.49.

TW-168

$^1$H NMR (CD$_3$COCD$_3$, 300 MHz,) δ (ppm) 11.67 (s, 1H), 10.17 (s, 1H), 8.06-7.00 (m, 15H), 3.72-3.78 (m, 4H), 3.31-3.05 (m, 2H), 2.91-2.84 (m, 4H), 1.29 (s, 9H); $^{13}$C NMR (CD$_3$COCD$_3$) δ (ppm) 169.41, 158.20, 148.78, 148.03, 146.55, 142.90, 139.05, 138.84, 133.09, 131.55, 130.98, 129.22, 129.15, 128.44, 125.46, 121.48, 121.18, 120.36, 117.93, 115.40, 113.88, 108.43, 49.29, 46.19, 39.15, 31.21, 28.86, 24.00, 22.80.

TW-169

$^1$H NMR (CD$_3$COCD$_3$, 300 MHz,) δ (ppm) 11.69 (s, 1H), 8.30 (d, 2H), 8.27 (s, 1H), 7.83 (s, 3H), 7.20 (d, 2H), 6.92 (d, 2H), 6.74 (s, 1H), 6.58 (s, 1H), 5.93 (t, 1H), 4.02-3.96 (m, 4H), 3.10-2.98 (m, 4H), 2.88 (s, 4H), 1.31 (s, 9H); $^{13}$C NMR (CD$_3$COCD$_3$) δ (ppm) 168.93. 161.43, 158.19, 149.40, 147.89, 147.28, 141.49, 138.55, 133.50, 131.51, 131.33, 129.35, 129.20, 128.58, 125.70, 121.10, 120.06, 116.31, 113.91, 110.99, 46.31, 43.16, 39.11, 37.69, 31.79.

TW-170

$^1$H NMR (CD$_3$COCD$_3$, 300 MHz,) δ (ppm) 11.78 (s, 1H), 8.27 (s, 1H), 7.80-7.21 (m, 15H), 6.94 (s, 1H), 5.88 (s, 1H), 3.84-3.74 (m, 2H), 2.90 (s, 4H), 2.53 (d, 2H), 2.31-2.19 (m, 5H), 1.33 (s, 9H); $^{13}$C NMR (CD$_3$COCD$_3$) δ (ppm) 168.99, 149.41, 147.91, 146.25, 141.13, 140.10, 138.63, 133.55, 132.33, 131.34, 129.40, 129.27, 128.72, 128.60, 126.50, 125.71, 121.17, 120.02, 116.34, 113.95, 46.88, 42.98, 37.72, 34.82, 31.82, 31.61.

TW-171

$^1$H NMR (CD$_3$COCD$_3$, 300 MHz,) δ (ppm) 11.06 (s, 1H), 7.85-6.97 (m, 15H), 6.31 (s, 1H), 4.27 (s, 2H), 3.39 (t, 2H), 3.21-3.17 (m, 8H), 2.95 (t, 2H).

TW-172

$^1$H NMR (CD$_3$COCD$_3$, 300 MHz,) δ (ppm) 10.63 (s, 1H), 8.21-7.09 (m, 20H), 4.12-4.03 (m, 2H), 3.65-3.54 (m, 2H), 3.15-2.95 (m, 2H), 2.75 (d, 2H), 1.76-1.56 (m, 3H).

TW-173

$^1$H NMR (CD$_3$COCD$_3$, 300 MHz,) δ (ppm) 10.67 (s, 1H), 8.10-6.67 (m, 21H), 4.28 (s, 2h), 3.50-3.37 (m, 6H), 2.95-2.90 (m, 4H), 2.70-2.65 (m, 3H); $^{13}$C NMR (CD$_3$COCD$_3$) δ (ppm) 168.60, 147.50, 144.02, 139.95, 133.63, 132.40, 132.24, 130.61, 129.42, 129.31, 129.18, 128.91, 128.28, 127.50, 127.03, 126.80, 126.56, 121.58, 118.95, 117.54, 117.28, 115.67, 48.52, 48.01, 45.22, 44.25, 31.36.

TW-174

$^1$H NMR (CD$_3$COCD$_3$, 300 MHz,) δ (ppm) 10.86 (s, 1H), 8.23-6.65 (m, 16H), 4.29 (s, 2H), 3.80-3.54 (m, 7H), 1.74-1.45 (m, 4H), 1.31 (s, 9H).

TW-175

$^1$H NMR (CD$_3$COCD$_3$, 300 MHz,) δ (ppm 10.59 (s, 1H), 9.01 (s, 1H), 8.07-6.36 (m, 18H), 4.20 (s, 2H), 3.79-3.69 (m, 2H), 3.40-3.32 (m, 6H), 1.79-1.58 (m, 3H).

TW-183—3-[2-(4-Tert-butyl-phenyl)-ethyl]-2-hydroxy-5-naphthalene-2-yl-benzoic acid $^1$H NMR (300 MHz, CD$_3$COCD$_3$): δ (ppm) 11.2 (br, 1H), 8.2-6.85 (m, 14H), 2.83-2.42 (m, 4H), 1.15 (s, 9H); $^{13}$C NMR (CD$_3$COCD$_3$): δ (ppm) 181.2, 148.3, 138.87, 137.24, 135.6, 134.85, 133.54, 132.17, 131.19, 130.56, 129.45, 128.92, 128.28, 128.12, 127.98, 127.44, 127.13, 125.99, 125.64, 125.44, 125.34, 125.24, 125.03, 124.65, 123.68, 38.51, 34.66, 32.04, 31.37.

TW-184—N-[-4-(4-Biphenyl-2-yl-ethyl-piperazin-1-yl)-phenyl]-2,3-dihydroxy-5-naphthalene-2-yl-benzamide $^1$H NMR (300 MHz, CD$_3$COCD$_3$): δ (ppm) 8.1 (d, J=3.2 Hz, 1H), 7.95-7.26 (m, 21H), 6.90 (d, J=7.1 Hz, 2H), 3.49 (s, 2H), 3.14 (t, J=5.4 Hz, 4H), 2.53 (t, J=5.3 Hz, 4H); $^{13}$C NMR (CD$_3$COCD$_3$): δ (ppm) 168.3, 149.36, 148.81, 146.313, 142.77, 141.38, 137.49, 135.355, 133.58, 132.48, 132.38, 130.15, 129.67, 129.51, 129.16, 128.58, 128.01, 127.85, 127.65, 127.14, 126.92, 126.87, 126.48, 126.00, 125.32, 125.16, 122.91, 117.55, 115.28, 114.83, 114.55, 59.73, 52.60, 49.20.

TW-189—2-Hydroxy-5-naphthalene-1-yl-3-phenethyl-benzoic acid $^1$H NMR (300 MHz, CD$_3$COCD$_3$): δ (ppm) 11.3 (br, 1H), 8.16 (d, J=2.3 Hz, 1H), 8.05-7.18 (m, 14H), 3.05 (m, 4H); $^{13}$C NMR (CD$_3$COCD$_3$): δ (ppm) 173.38, 160.72, 142.89, 138.20, 135.85, 134.78, 133.41, 132.48, 131.31, 131.00, 129.42, 129.35, 129.15, 128.95, 128.42, 127.78, 127.40, 126.68, 125.82, 125.67, 36.38, 32.78.

TW-190—2-Hydroxy-5-naphthalene-1-yl-3-{2-[4-(4-phenyl-butylsulfamoyl)-phenyl]-ethyl}-benzoic acid $^1$H NMR (300 MHz, CD$_3$COCD$_3$): δ (ppm) 8.22 (s, 1H), 8.13 (s, 1H), 8.03-6.95 (m, 16H), 6.35 (s, 1H), 3.14 (m, 4H), 2.82 (m, 2H), 2.46 (m, 2H), 1.53-1.62 (m, 4H); $^{13}$C NMR (CD$_3$COCD$_3$): δ (ppm) 160.11, 147.23, 142.611, 139.03, 137.64, 134.97, 134.29, 132.88, 130.03, 129.90, 129.58, 129.53, 128.88, 128.70, 128.52, 127.91, 127.33, 126.68, 126.16, 126.00, 125.35, 125.07, 43.16, 43.07, 35.54, 35.39, 31.91, 23.50.

TW-194—4-Chloro-3-(methyl-phenethyl-sulfamoyl)-5-[(naphthalene-2-carbonyl)-amino]-benzoic acid $^1$H NMR (300 MHz, CD$_3$COCD$_3$): δ (ppm) 9.35 (s, 1H), 9.12 (s, 1H), 8.80 (s, 1H), 8.46 (s, 1H), 8.12-7.22 (m, 11H), 3.78 (m, 2H), 3.03 (s, 3H), 2.94 (m, 2H); $^{13}$C NMR (CD$_3$COCD$_3$): δ (ppm) 165.96, 165.47, 138.97, 138.93, 138.28, 135.58, 133.06, 131.78, 130.13, 129.57, 129.28, 128.12, 129.01, 128.77, 128.70, 128.61, 128.52, 128.28, 128.21, 127.43, 126.77, 124.41, 51.59, 34.65, 34.48.

TW-195—4-Chloro-3-(4-fluoro-benzoylamino)-5-(methyl-phenethyl-sulfamoyl)-benzoic acid $^1$H NMR (300 MHz, CD$_3$COCD$_3$): δ (ppm) 9.33 (s, 1H), 8.53 (s, 1H), 8.47 (s, 1H), 8.02 (m, 2H), 7.30-7.11 (m, 7H), 3.62 (t, J=6.8 Hz, 3H), 2.98 (s, 3H), 2.89 (t, J=5.4 Hz, 3H); $^{13}$C NMR (CD$_3$COCD$_3$): δ (ppm) 164.87, 164.10, 130.30, 130.17, 129.10, 128.88, 128.14, 127.39, 126.94, 126.26, 116.66, 116.37, 52.04, 35.15, 34.98.

TW-196—3-[(Benzofuran-2-carbonyl)-amino]-4-chloro-5-(methyl-phenethyl-sulfamoyl)-benzoic acid $^1$H NMR (300 MHz, CD$_3$COCD$_3$): δ (ppm) 10.51 (s, 1H), 8.44 (s, 1H), 8.32 (s, 1H), 7.82-7.16 (m, 9H), 3.62 (t, J=6.8 Hz, 3H), 2.98 (s, 3H), 2.89 (t, J=5.4 Hz, 3H); $^{13}$C NMR (CD$_3$COCD$_3$): δ (ppm) 166.07, 157.82, 155.41, 148.61, 139.10, 139.01, 137.91, 132.36, 131.83, 130.70, 129.55, 129.22, 128.50, 127.86, 127.22, 124.93, 124.03, 112.91, 112.61, 52.00, 35.28, 34.62.

TW-198—3-[(Biphenyl-4-carbonyl)-amino]-4-chloro-5-(methyl-phenethyl-sulfamoyl)-benzoic acid $^1$H NMR (300 MHz, CD$_3$COCD$_3$): δ (ppm) 9.42 (s, 1H), 9.05 (s, 1H), 8.51 (s, 1H), 8.22-7.12 (m, 15H), 3.54 (m, 2H), 3.09 (s, 3H), 2.96 (m, 3H); $^{13}$C NMR (CD$_3$COCD$_3$): δ (ppm) 165.56, 165.43, 145.19, 140.02, 138.93, 138.23, 133.17, 130.04, 129.45, 129.26, 129.12, 128.77, 128.71, 128.62, 128.24, 127.57, 127.50, 126.77, 51.88, 34.63, 34.48.

TW-199—4-Chloro-3-(methyl-phenethyl-sulfamoyl)-5-{4-(4-phenyl-piperdine-1-sulfonyl)-benzoylamino}-benzoic acid $^1$H NMR (300 MHz, CD$_3$COCD$_3$): δ (ppm) 9.67 (s, 1H), 8.95 (s, 1H), 8.51 (s, 1H), 8.51 (d, J=8.1 Hz, 2lH), 8.02 (d, J=7.5 Hz, 2H), 7.32-7.19 (m, 10H), 3.9 (m, 2H), 3.58 (m, 2H), 3.31 (s, 3H), 2.96 (m, 2H), 2.43 (m, 4H), 1.84 (m, 4H); $^{13}$C NMR (CD$_3$COCD$_3$): δ (ppm) 165.20, 165.00, 145.73, 140.18, 139.18, 138.92, 138.31, 137.97, 137.86, 130.01, 129.97, 129.47, 129.12, 129.02, 128.82, 128.88, 128.47, 127.11, 126.78, 126.75, 51.92, 47.18, 41.74, 34.78, 34.65, 34.52, 32.86.

TW-200—3-(4-Benzoyl-benzoylamino)-4-chloro-5-(methyl-phenethyl-sulfamoyl)benzoic acid $^1$H NMR (300 MHz, CD$_3$COCD$_3$): δ (ppm) 9.56 (s, 1H), 9.00 (s, 1H), 8.53 (s, 1H), 8.32-7.65 (m, 9H), 7.32-6.93 (m, 5H), 3.55 (m, 2H), 3.02 (s, 3H), 2.89 (m, 2H); $^{13}$C NMR (CD$_3$COCD$_3$): δ (ppm) 181.3, 138.94, 137.45, 133.30, 130.25, 129.80, 129.13, 128.96, 128.28, 128.18, 126.80, 51.89, 34.66, 34.51.

TW-201—3-Benzoylamino-4-chloro-5-(methyl-phenethyl-sulfamoyl)-benzoic acid $^1$H NMR (300 MHz, CD$_3$COCD$_3$): δ (ppm) 9.37 (s, 1H), 9.04 (s, 1H), 8.47 (s, 1H), 8.21-7.13 (m, 10H), 3.63 (m, 2H), 3.02 (s, 3H), 2.89 (m, 2H); $^{13}$C NMR (CD$_3$COCD$_3$): δ (ppm) 165.87, 165.30, 138.93, 138.23, 134.47, 132.75, 129.88, 129.18, 129.11, 128.76, 128.23, 128.00, 126.76, 51.87, 34.62, 34.47.

TW-202—4-Chloro-3-[4-(3,4-dihydro-1H-isoquinoline-2-sulfonyl)-benzoylamino]-5-(methyl-phenethyl-sulfamoyl)-benzoic acid $^1$H NMR (300 MHz, CD$_3$COCD$_3$): δ (ppm) 9.63 (s, 1H), 8.92 (s, 1H), 8.50 (s, 1H), 8.29 (d, J=8.1 Hz, 2H), 8.07 (d, J=8.0 Hz, 2H), 7.34-7.03 (m, 8H), 4.33 (s, 2H), 3.54 (m, 2H), 3.45 (m, 4H), 3.10 (s, 3H), 3.10-3.01 (m, 2H); $^{13}$C NMR (CD$_3$COCD$_3$): δ (ppm) 165.19, 164.96, 140.40, 139.15, 138.91, 138.41, 137.93, 133.57, 132.12, 129.95, 129.20, 129.11, 129.05, 128.77, 128.41, 127.13, 126.77, 126.65, 51.89, 47.87, 44.22, 34.62, 34.49.

TW-203—4-Chloro-3-(methyl-phenethyl-sulfamoyl)-5-{4[methyl-(3-phenyl-propyl)-sulfamoyl]-benzoylamino}-benzoic acid $^1$H NMR (300 MHz, CD$_3$COCD$_3$): δ (ppm) 9.63 (s, 1H), 8.82 (s, 1H), 8.49 (s, 1H), 8.23 (d, J=7.5 Hz, 2H), 7.93 (d, J=7.6 Hz, 2H), 7.34-6.90 (m, 10H), 3.42-3.02 (m, 8H), 2.74 (s, 3H), 2.65 (s, 3H), 1.90-1.78 (m, 2H); $^{13}$C NMR (CD$_3$COCD$_3$): δ (ppm) 164.32, 142.05, 141.17, 139.00, 138.02, 137.73, 129.17, 129.05, 128.77, 127.99, 126.68, 126.12, 51.86, 50.06, 34.88, 34.66, 32.87, 30.12.

TW-204—4-Chloro-3-(4-methoxy-benzoylamino)-5-(methyl-phenethyl-sulfamoyl)-benzoic acid $^1$H NMR (300 MHz, CD$_3$COCD$_3$): δ (ppm) 9.20 (s, 1H), 9.06 (s, 1H), 8.46 (s, 1H), 8.06 (d, J=7.5 Hz, 2H), 7.34-7.02

(m, 7H), 3.91 (s, 3H), 3.57 (m, 2H), 3.02 (s, 3H), 2.95 (m, 2H); $^{13}$C NMR (CD$_3$COCD$_3$): δ (ppm) 165.31, 163.53, 138.92, 138.42, 129.97, 129.77, 128.76, 127.87, 126.76, 126.43, 114.37, 55.47, 51.86, 34.62, 34.45.

TW-205—3-[(Adamantane-1-carbonyl)-amino]-4-chloro-5-(methyl-phenethyl-sulfamoyl)-benzoic acid $^1$H NMR (300 MHz, CD$_3$COCD$_3$): δ (ppm) 9.0 (s, 1H), 8.41 (m, 2H), 7.44-7.23 (m, 5H), 3.52 (m, 2H), 3.01 (s, 3H), 2.89 (m, 2H), 2.04 (s, 10H), 1.74 (s, 3H); $^{13}$C NMR (CD$_3$COCD$_3$): δ (ppm) 176.13, 165.36, 138.88, 138.65, 138.12, 129.80, 129.08, 128.70, 128.00, 127.44, 127.21, 126.76, 51.77, 42.29, 39.17, 36.55, 34.54, 34.37.

TM-1230—2-[5-(3,4-Dihydro-1H-isoquinoline-2-sulfonyl)-2,3,4-trihydroxy-benzoyl]-1,2,3,4-tetrahydro-isoquinoline-7-sulfonic acid (3-benzoyl-phenyl)-amide $^1$H NMR (CDCl$_3$, 300 MHz) δ 10.4 (s, 1H), 8.52 (s, 1H), 8.00-6.97 (m, 17H), 6.68 (1H), 6.28 (s, 1H), 4.85-4.63 (m, 2H), 4.28 (s, 1H), 3.79 (m, 3H), 3.38 (s, 1H), 3.22-3.09 (m, 2H), 2.95-2.87 (m, 3H); $^1$H NMR (CO(CD$_3$)$_2$, 300 MHz) δ 9.27 (b, 1H), 7.70-7.66 (m, 4.5H), 7.61-7.59 (m, 2.5H), 7.56-7.47 (m, 7H), 7.38 (m, 3H), 7.29 (s, 0.5H), 7.12 (b, 2H), 6.82 (s, 0.5H), 4.84 (d, 2H), 4.38 (s, 1H), 3.83 (m, 2H), 3.02 (m, 1H), 2.90 (m, 3H); $^{13}$C NMR (CO(CD$_3$)$_2$, 75 MHz) δ 195.8, 169.1, 167.5, 150.5, 148.2, 141.3, 139.2, 138.8, 138.5, 138.0, 135.2, 133.4, 130.5, 130.3, 129.7, 129.2, 127.4, 126.4, 125.8, 125.3, 122.2, 115.8, 48.0, 44.5, 39.7.

TM-1231—2,3,4-Trihydroxy-5-isopropyl-N-naphthalen-2-yl-benzene-sulfonamide $^1$H NMR (CDCl$_3$, 300 MHz) δ 8.55 (s, 1H), 7.74-7.67 (m, 3H), 7.51 (d, 1H), 7.43 (m, 2H), 7.16 (dd, 1H), 7.05 (s, 1H), 6.90 (s, 1H), 5.86 (s, 1H), 5.54 (s, 1H), 3.05 (hept, 1H), 0.99 (d, 6H); $^{13}$C NMR (CDCl$_3$, 75 MHz) δ 147.1, 141.4, 133.8, 133.4, 131.9, 131.5, 129.8, 128.7, 128.0, 127.9, 127.1, 126.3, 122.4, 121.0, 117.1, 112.9, 26.9, 22.4.

TM-1232—2,3,4-Trihydroxy-5-isopropyl-N-methyl-N-naphthalen-2-yl-benzenesulfonamide $^1$H NMR (CDCl$_3$, 300 MHz) δ 8.48 (s, 1H), 7.83 (m, 1H), 7.80 (d, 1H), 7.74 (m, 1H), 7.53 (d, 1H), 7.51-7.48 (m, 2H), 7.27 (dd, 1H), 6.63 (s, 1H), 5.91 (b, 1H), 5.51 (b, 1H), 3.26 (s, 3H), 3.14 (hept, 1H), 1.02 (d, 6H); $^{13}$C NMR (CDCl$_3$, 75 MHz) δ 146.9, 141.7, 138.9, 133.5, 132.7, 131.4, 129.2, 128.26, 128.2, 128.0, 127.0, 126.96, 125.6, 125.4, 117.5, 110.8, 38.5, 26.9, 22.5.

TM-1233—N-Ethyl-2,3,4-trihydroxy-5-isopropyl-N-naphthalen-2-yl-benzene-sulfonamide $^1$H NMR (CDCl$_3$, 300 MHz) δ 8.48 (s, 1H), 7.82-7.72 (m, 3H), 7.55 (s, 1H), 7.48 (m, 2H), 7.13 (dd, 1H), 6.76 (s, 1H), 5.88 (s, 1H), 5.48 (b, 1H), 3.66 (q, 2H), 3.17 (hept, 1H), 1.10-1.06 (m, 9H); $^{13}$C NMR (CDCl$_3$, 75 MHz) δ 146.9, 141.4, 135.8, 133.5, 133.0, 131.5, 129.3, 128.4, 128.3, 128.2, 127.9, 127.1, 126.9, 126.6, 117.2, 112.8, 45.8, 26.9, 22.6, 14.1.

TM-1234—2,3,4-Trihydroxy-5-isopropyl-N-naphthalen-2-yl-N-propyl-benzenesulfonamide $^1$H NMR (CDCl$_3$, 300 MHz) δ 8.55 (s, 1H), 7.80-7.71 (m, 3H), 7.59 (s, 1H), 7.49-7.44 (m, 2H), 7.16 (dd, 1H), 6.77 (s, 1H), 6.18 (b, 1H), 5.89 (b, 1H), 3.58 (t, 2H), 3.19 (hept, 1H), 1.44 (hex, 2H), 1.09 (d, 6H), 0.90 (t, 3H); $^{13}$C NMR (CDCl$_3$, 75 MHz) δ 146.9, 141.5, 136.1, 133.5, 133.0, 131.4, 129.2, 128.24, 128.19, 127.9, 127.0, 126.8, 126.4, 117.2, 112.7, 52.5, 26.9, 22.5, 21.6.

TM-1235—2,3,4-Trihydroxy-5,N-diisopropyl-N-naphthalen-2-yl-benzene-sulfonamide $^1$H NMR (CDCl$_3$, 300 MHz) δ 8.58 (b, 1H), 7.85-7.75 (m, 3H), 7.54 (s, 1H), 7.52-7.47 (m, 2H), 7.12 (dd, 1H), 7.00 (s, 1H), 5.93 (b, 1H), 5.58 (b, 1H), 4.65 (hept, 1H), 3.24 (hept, 1H), 1.18 (d, 6H), 1.11 (d, 6H); $^{13}$C NMR (CDCl$_3$, 75 MHz) δ 146.5, 141.2, 133.4, 133.3, 132.1, 131.8, 131.4, 129.9, 129.0, 128.4, 127.9, 127.4, 126.8, 116.9, 115.6, 52.1, 27.0, 22.7, 22.3.

TM-1236—2,3,4-Trihydroxy-N-isobutyl-5-isopropyl-N-naphthalen-2-yl-benzenesulfonamide $^1$H NMR (CDCl$_3$, 300 MHz) δ 8.53 (s, 1H), 7.83-7.73 (m, 3H), 7.59 (s, 1H), 7.50-7.47 (m, 2H), 7.18 (dd, 1H), 6.73 (s, 1H), 5.94 (b, 1H), 5.55 (b, 1H), 3.39 (d, 2H), 3.18 (m, 1H), 1.63 (m, 1H), 1.09 (d, 6H), 0.92 (d, 6H); $^{13}$C NMR (CDCl$_3$, 75 MHz) δ 146.7, 141.5, 136.6, 133.6, 133.0, 131.4, 129.3, 128.3, 128.2, 128.1, 128.0, 127.1, 126.9, 126.4, 117.2, 112.8, 58.3, 27.1, 27.0, 22.6, 20.2.

TM-1237—2,3,4-Trihydroxy-5-isopropyl-N-phenethyl-benzenesulfonamide $^1$H NMR (CDCl$_3$, 300 MHz) δ 8.70 (b, 1H), 7.30-7.20 (m, 3H), 7.06 (d, 2H), 6.96 (s, 1H), 5.92 (b, 1H), 5.65 (b, 1H), 4.49 (t, 1H), 3.27-3.16 (m, 3H), 2.76 (t, 2H), 1.21 (d, 6H); $^{13}$C NMR (CDCl$_3$, 75 MHz) δ 147.2, 141.5, 137.7, 131.8, 129.0, 128.9, 128.8, 127.1, 116.6, 113.8, 44.3, 35.6, 27.2, 22.5.

TM-1238—N-Ethyl-2,3,4-trihydroxy-5-isopropyl-N-phenethyl-benzene-sulfonamide $^1$H NMR (CDCl$_3$, 300 MHz) δ 9.00, 7.31-7.23 (m, 3H), 7.18-7.14 (m, 2H), 6.95 (s, 1H), 5.94 (b, 1H), 5.70 (b, 1H), 3.36 (t, 2H), 3.26 (t, 2H), 3.18 (m, 1H), 2.84 (t, 2H), 1.20 (d, 6H), 1.11 (t, 3H); $^{13}$C NMR (CDCl$_3$, 75 MHz) δ 146.6, 141.4, 138.5, 131.6, 129.0, 128.9, 128.6, 126.9, 116.2, 114.4, 49.0, 43.2, 35.7, 27.2, 22.6, 13.9.

TM-1239—2-[5-(3,4-Dihydro-1H-isoquinoline-2-sulfonyl)-2,3,4-trihydroxy-benzoyl]-1,2,3,4-tetrahydro-isoquinoline-7-sulfonic acid [2-(4-tert-butyl-phenyl)-ethyl]-amide $^1$H NMR (CO(CD$_3$)$_2$, 300 MHz) δ 10.13 (b, 1H), 9.06 (b, 1H), 8.50 (b, 1H), 7.72-7.70 (m, 2H), 7.41 (m, 3H), 7.30 (m, 2H), 7.14-7.07 (m, 5H), 6.45 (t, 1H), 4.92 (s, 2H), 4.39 (s, 2H), 3.86 (m, 2H), 3.52 (t, 2H), 3.11 (m, 2H), 2.93 (m, 4H), 2.74 (m, 2H), 1.27 (s, 9H); $^{13}$C NMR (CO(CD$_3$)$_2$, 75 MHz) δ 169.2, 167.5, 150.8, 149.7, 147.0, 140.4, 139.8, 136.4, 135.3, 134.2, 132.8, 130.4, 129.6, 129.2, 127.4, 127.2, 126.0, 121.4, 48.0, 45.4, 44.5, 36.1, 31.6, 31.6.

TM-1240—2-[2,3,4-Trihydroxy-5-(4-phenyl-butyl-sulfamoyl)-benzoyl]-1,2,3,4-tetrahydro-isoquinoline-7-sulfonic acid phenethyl-amide $^1$H NMR (CDCl$_3$, 300 MHz) δ 10.14 (b, 1H), 8.30 (b, 1H), 7.59 (d, 1H), 7.55 (s, 1H), 7.38 (s, 1H), 7.25-7.19 (m, 6H), 7.15 (m, 1H), 7.08-7.06 (m, 4H), 6.55 (b, 1H), 5.24 (t, 1H), 5.01 (t, 1H), 4.76 (s, 2H), 3.81 (m, 2H), 3.15 (m, 2H), 2.98 (m, 2H), 2.88 (m, 2H), 2.76 (m, 2H), 2.52 (m, 2H), 1.57-1.48 (m, 4H); $^{13}$C NMR (CDCl$_3$, 75 MHz) δ 169.9, 150.7, 145.4, 142.0, 139.7, 138.5, 138.1, 134.1, 133.6, 129.8, 129.1, 129.0, 128.6, 127.0, 126.2, 126.0, 125.4, 120.6, 116.2, 111.2, 44.7, 43.4, 36.2, 35.5, 29.2, 28.5.

TM-1241—2-{2,3,4-Trihydroxy-5-[methyl-(4-phenyl-butyl)-sulfamoyl]-benzoyl}-1,2,3,4-tetrahydroisoquinoline-7-sulfonic acid methyl-phenethyl-amide $^1$H NMR (CDCl$_3$, 300 MHz) δ 9.78 (b, 1H), 8.78 (b, 1H), 7.56 (d, 1H), 7.47 (s, 1H), 7.28-7.23 (m, 6H), 7.18-7.13 (m, 6H), 6.32 (b, 1H), 4.81 (s, 2H), 3.85 (m, 2H), 3.26 (m, 2H), 3.06-3.00 (m, 4H), 2.85 (t, 2H), 2.74 (s, 3H), 2.70 (s, 3H), 2.61 (t, 2H), 1.64-1.56 (m, 4H); $^{13}$C NMR (CDCl$_3$, 75 MHz) δ 169.7, 150.4, 145.7, 142.0, 139.5, 138.4, 136.6, 133.9, 133.8, 129.9, 129.0, 128.8, 128.6, 126.8, 126.1, 126.0, 125.6, 120.0, 113.6, 111.5, 52.0, 50.0, 35.5, 35.4, 35.1, 34.7, 29.2, 28.3, 27.2, 14.4.

TM-1242—2-{5-[Ethyl-(4-phenyl-butyl)-sulfamoyl]-2,3,4-trihydroxy-benzoyl}-1,2,3,4-tetrahydroisoquinoline-7-sulfonic acid ethyl-phenethyl-amide $^1$H NMR (CDCl$_3$, 300 MHz) δ 10.10 (b, 1H), 8.90 (b, 1H), 7.61 (d, 1H), 7.52 (s, 1H), 7.34-7.23 (m, 8H), 7.18-7.12 (m, 6H), 4.82 (s, 2H), 3.87 (m, 2H), 3.35 (m, 2H), 3.26-3.16 (m, 6H), 3.02 (m, 2H), 2.88 (m, 2H), 2.61 (m, 2H), 1.60 (m, 4H), 1.15-1.06 (m, 6H); $^{13}$C NMR (CDCl$_3$, 75 MHz) δ 169.7, 150.1, 145.5, 142.0, 139.3, 138.7, 138.6, 133.7, 129.8, 129.0, 128.8, 128.6, 126.8, 126.1, 125.7, 125.3, 119.8, 116.0, 111.6, 49.3, 47.6, 43.3, 42.9, 36.1, 35.5, 29.1, 28.4, 28.2, 14.3, 14.1.

TM-1243—6-(2,3,4-Trihydroxy-5-isopropyl-benzenesulfonylamino)-naphthalene-2-carboxylic acid $^1$H NMR (CO(CD$_3$)$_2$, 300 MHz) δ 9.43 (b, 1H), 8.56 (s, 1H), 8.20 (b, 1H), 8.02-7.98 (m, 2H), 7.87 (d, 1H), 7.76 (s, 1H), 7.51 (dd, 1H), 7.08 (s, 1H), 3.13 (m, 1H), 1.06 (d, 6H); $^{13}$C NMR (CO(CD$_3$)$_2$, 75 MHz) δ 167.6, 149.4, 143.6, 138.6, 136.9, 133.3, 131.5, 130.6, 128.5, 128.2, 127.0, 122.3, 117.7, 117.3, 114.7, 27.3, 22.3.

TM-1244—6-[Ethyl-(2,3,4-trihydroxy-5-isopropyl-benzenesulfonyl)-amino]-naphthalene-2-carboxylic acid ethyl ester $^1$H NMR (CDCl$_3$, 300 MHz) δ 8.60 (s, 1H), 8.47 (s, 1H), 8.09 (d, 1H), 7.91 (d, 1H), 7.79 (d, 1H), 7.62 (s, 1H), 7.23 (d, 1H), 6.73 (s, 1H), 5.91 (s, 1H), 5.49 (s, 1H), 4.45 (q, 2H), 3.69 (q, 2H), 3.18 (hept, 1H), 1.45 (t, 3H), 1.13-1.08 (m, 9H); $^{13}$C NMR (CDCl$_3$, 75 MHz) δ 166.8, 147.0, 141.5, 138.1, 135.6, 132.0, 131.5, 130.8, 130.6, 128.8, 128.4, 127.4, 126.3, 117.1, 112.5, 61.6, 45.7, 26.9, 22.6, 14.6, 14.1.

TM-1245—6-(2,3,4-Trihydroxy-5-isopropyl-benzenesulfonylamino)-naphthalene-2-carboxylic acid phenethyl-amide $^1$H NMR (CD$_3$OD, 300 MHz) δ 8.15 (s, 1H), 7.78-7.69 (m, 3H), 7.53 (s, 1H), 7.29 (dd, 1H), 7.23 (m, 4H), 7.15 (m, 1H), 6.94 (s, 1H), 3.58 (t, 2H), 3.03 (m, 1H), 2.89 (t, 2H), 0.98 (d, 6H).

TM-1246—6-(2,3,4-Trihydroxy-5-isopropyl-benzenesulfonylamino)-naphthalene-2-carboxylic acid (3-phenyl-propyl)-amide $^1$H NMR (CO(CD$_3$)$_2$, 300 MHz) δ 9.41 (s, 1H), 8.63 (s, 1H), 8.34 (s, 1H), 8.21 (s, 2H), 7.99 (t, 1H), 7.93 (d, 1H), 7.86 (d, 1H), 7.80 (d, 1H), 7.73 (s, 1H), 7.47 (dd, 1H), 7.24 (m, 4H), 7.15 (m, 1H), 7.08 (s, 1H), 3.48 (m, 2H), 3.10 (m, 1H), 2.71 (t, 2H), 1.95 (pent, 2H), 1.05 (d, 6H); $^{13}$C NMR (CO(CD$_3$)$_2$, 75 MHz) δ 167.6, 149.3, 143.6, 142.9, 137.9, 135.9, 133.3, 132.4, 130.9, 130.7, 129.2, 129.1, 128.2, 128.0, 127.99, 126.6, 125.7, 122.3, 117.7, 117.6, 114.8, 40.2, 33.9, 32.2, 27.2, 22.7.

TM-1247—6-(2,3,4-Trihydroxy-5-isopropyl-benzenesulfonylamino)-naphthalene-2-carboxylic acid (4-phenyl-butyl)-amide $^1$H NMR (CO(CD$_3$)$_2$, 300 MHz) δ 9.32 (s, 1H), 8.59 (s, 1H), 8.34 (s, 1H), 8.10 (dd, 1H), 7.92-7.80 (m, 4H), 7.72 (d, 1H), 7.45 (dd, 1H), 7.25-7.20 (m, 4H), 7.15 (m, 1H), 7.04 (s, 1H), 3.47 (m, 2H), 3.11 (m, 1H), 2.66 (t, 2H), 1.70 (m, 4H), 1.04 (d, 6H); $^{13}$C NMR (CO(CD$_3$)$_2$, 75 MHz) δ 167.5, 149.3, 143.6, 143.3, 137.8, 135.8, 133.2, 132.5, 130.9, 130.7, 129.2, 129.0, 128.2, 128.1, 128.0, 126.4, 125.7, 122.4, 117.7, 114.7, 40.4, 36.1, 27.2, 22.7.

TM-1248—2-(2,3,4-Trihydroxy-5-phenylsulfamoyl-benzoyl)-1,2,3,4-tetrahydro-isoquinoline-7-sulfonic acid phenethyl-amide $^1$H NMR (CDCl$_3$, 300 MHz) δ 10.25 (b, 1H), 8.15 (b, 1H), 7.57 (m, 2H), 7.48 (s, 1H), 7.20-7.05 (m, 12H), 6.50 (b, 1H), 5.30 (m, 1H), 4.61 (s, 2H), 3.64 (m, 2H), 3.17 (m, 2H), 2.88 (m, 2H), 2.76 (m, 2H); $^{13}$C NMR (CDCl$_3$, 75 MHz) δ 168.9, 148.1, 146.4, 134.2, 133.8, 131.6, 131.1, 129.0, 127.8, 127.7, 126.9, 126.7, 125.6, 121.0, 118.6, 113.7, 106.9, 27.4, 22.6.

TM-1249—2-{2,3,4-Trihydroxy-5-[methyl-(4-phenyl-butyl)-sulfamoyl]-benzoyl}-1,2,3,4-tetrahydroisoquinoline-7-sulfonic acid phenethyl-amide $^1$H NMR (CO(CD$_3$)$_2$, 300 MHz) δ 10.39 (b, 1H), 8.56 (b, 1H), 7.63 (d, 1H), 7.50 (s, 1H), 7.36 (s, 1H), 7.25-7.16 (m, 6H), 7.19 (m, 1H), 7.08-7.02 (m, 4H), 6.68 (b, 1H), 5.40 (t, 1H), 4.76 (s, 2H), 3.81 (m, 2H), 3.15 (m, 2H), 2.98 (m, 2H), 2.88 (m, 2H), 2.76 (m, 2H), 2.52 (m, 2H), 2.32 (s, 3H), 1.57-1.48 (m, 4H); $^{13}$C NMR (CO(CD$_3$)$_2$, 75 MHz) δ 169.9, 150.7, 145.4, 142.0, 139.7, 138.5, 138.1, 134.1, 133.6, 129.8, 129.1, 129.0, 128.6, 127.0, 126.2, 126.0, 125.4, 120.6, 116.2, 111.2, 44.7, 43.4, 36.2, 35.5, 29.2, 28.5.

TM-1250—2,3,4-Trihydroxy-5-isopropyl-N-naphthalen-2-yl-benzamide $^1$H NMR (CDCl$_3$, 300 MHz) δ 12.40 (s, 1H), 8.09 (d, 1H), 8.01 (s, 1H), 7.81-7.75 (m, 3H), 7.54 (dd, 1H), 7.44 (m, 2H), 6.91 (s, 1H), 6.01 (b, 2OH), 3.24 (m, 1H), 1.27 (d, 6H); $^{13}$C NMR (CDCl$_3$, 75 MHz) δ 168.9, 148.1, 146.4, 134.2, 133.8, 131.6, 131.1, 129.0, 127.8, 127.7, 126.9, 126.7, 125.6, 121.0, 118.6, 113.7, 106.9, 27.4, 22.6.

TM-1251—2-{5-[Ethyl-(3-phenyl-propyl)-sulfamoyl]-2,3,4-trihydroxy-benzoyl}-1,2,3,4-tetrahydroisoquinoline-7-sulfonic acid phenethyl-amide $^1$H NMR (CO(CD$_3$)$_2$, 300 MHz) δ 10.53 (b, 1H), 8.45 (b, 1H), 7.66 (d, 1H), 7.64 (s, 1H), 7.39 (d, 1H), 7.35 (s, 1H), 7.24-7.13 (m, 11H), 6.49 (t, 1H), 4.88 (s, 2H), 3.86 (t, 2H), 3.36-3.28 (m, 4H), 3.15 (m, 2H), 3.04 (m, 2H), 2.77 (t, 2H), 2.61 (t, 2H), 1.87 (pent, 2H), 1.11 (t, 3H); $^{13}$C NMR (CO(CD$_3$)$_2$, 75 MHz) δ 169.4, 150.6, 146.7, 142.5, 140.4, 139.9, 139.7, 135.3, 134.5, 130.4, 129.6, 129.2, 129.1, 127.1, 126.6, 126.0, 125.8, 120.9, 117.6, 113.4, 55.0, 47.8, 45.4, 45.3, 43.9, 43.3, 36.6, 33.5, 31.2, 14.5.

TM-1252—2-{2,3,4-Trihydroxy-5-[(3-phenyl-propyl)-propyl-sulfamoyl]-benzoyl}-1,2,3,4-tetrahydro-isoquinoline-7-sulfonic acid phenethyl-amide $^1$H NMR (CO(CD$_3$)$_2$, 300 MHz) δ 9.25 (b, 2OH), 7.66 (d, 1H), 7.64 (s, 1H), 7.38 (d, 1H), 7.36 (s, 1H), 7.23-7.10 (m, 11H), 6.52 (b, 1H), 4.87 (s, 2H), 3.85 (m, 2H), 3.31-3.20 (m, 4H), 3.17 (t, 2H), 3.02 (m, 2H), 2.77 (t, 2H), 2.59 (t, 2H), 1.86 (m, 2H), 1.55 (m, 2H), 0.84 (t, 3H); $^{13}$C NMR (CO(CD$_3$)$_2$, 75 MHz) δ 169.4, 150.6, 146.7, 142.4, 140.4, 139.9, 139.6, 135.2, 134.5, 130.4, 129.58, 129.18, 129.14, 129.12, 127.1, 126.6, 125.9, 125.8, 120.9, 117.5, 113.5, 50.6, 48.4, 45.4, 36.6, 33.5, 22.6, 11.4.

TM-1253—6-(2-Hydroxy-5-isopropyl-benzenesulfonylamino)-naphthalene-2-carboxylic acid (3-phenyl-propyl)-amide $^1$H NMR (CO(CD$_3$)$_2$, 300 MHz) δ 8.32 (s, 1H), 7.96 (t, 1H), 7.93 (dd, 1H), 7.84 (d, 1H), 7.77 (d, 1H), 7.74 (d, 1H), 7.65 (d, 1H), 7.53 (dd, 1H), 7.29-7.22 (m, 6H), 7.19-7.13 (m, 2H), 6.90 (d, 1H), 3.47 (m, 2H), 2.78 (m, 1H), 2.71 (m, 2H), 1.95 (m, 2H), 1.10 (d, 6H); $^{13}$C NMR (CO(CD$_3$)$_2$, 75 MHz) δ 167.4, 154.0, 142.9, 140.7, 138.0, 135.9, 133.9, 132.3, 130.8, 130.5, 129.2, 129.1, 128.1, 128.0, 127.9, 126.6, 125.7, 124.7, 121.9, 118.2, 116.7, 40.2, 33.9, 33.7, 32.1, 24.1.

TM-1254—6-[Methyl-(2,3,4-trihydroxy-5-isopropyl-benzenesulfonyl)-amino]-naphthalene-2-carboxylic acid phenethyl-propyl-amide $^1$H NMR (CDCl$_3$, 300 MHz) δ 8.38 (s, 1H), 7.75-7.66 (m, 2.5H), 7.50 (s, 1H), 7.42-7.31 (m, 4.5H), 7.21 (m, 2H), 6.88 (s, 1H), 6.53 (d, 1H), 6.30 (d, 1H), 6.24 (s, 1H), 3.77 (m, 1H), 3.60 (m, 1H), 3.49 (m, 1H), 3.23 (s, 3H), 3.14-3.05 (m, 3H), 2.78 (m, 1H), 1.78 (m, 1H), 1.50 (m, 1H), 1.03 (m, 1.5H), 0.96 (d, 6H), 0.67 (m, 1.5H); $^{13}$C NMR (CDCl$_3$, 75 MHz) δ 171.8, 147.1, 141.8, 139.6, 139.0, 137.7, 134.7, 133.1, 131.6, 131.4, 129.2, 128.9, 128.6, 128.2, 127.7, 126.7, 126.5, 125.8, 125.6, 124.9, 124.7, 117.0, 110.2, 53.4, 51.4, 50.5, 46.8, 46.4, 38.0, 34.9, 33.7, 26.5, 22.2.

TM-1255—6-[Methyl-(2,3,4-trihydroxy-5-isopropyl-benzenesulfonyl)-amino]-naphthalene-2-carboxylic acid cyclohexylmethyl-amide $^1$H NMR (CDCl$_3$, 300 MHz) δ 8.38 (s, 1H), 8.21 (s, 1H), 7.83-7.75 (m, 3H), 7.54 (d, 1H), 7.33 (dd, 1H), 6.60 (s, 1H), 6.48 (t, 1H), 6.15 (s, 1H), 6.03 (s, 1H), 3.34 (t, 2H), 3.26 (s, 3H), 3.14 (m, 1H), 1.83-1.66 (m, 7H), 1.21 (m, 2H), 1.06-0.95 (m, 8H); $^{13}$C NMR (CDCl$_3$, 75 MHz) δ 167.5, 147.0, 141.6, 140.2, 134.4, 132.6, 131.5, 131.3, 129.8, 128.4, 127.9, 126.9, 125.9, 124.8, 124.3, 117.0, 110.2, 53.4, 46.4, 38.0, 30.9, 26.6, 26.3, 25.8, 22.6.

TM-1256—6-[Propyl-(2,3,4-trihydroxy-5-isopropyl-benzenesulfonyl)-amino]-naphthalene-2-carboxylic acid (3-phenyl-propyl)-amide $^1$H NMR (CDCl$_3$, 300 MHz) δ 8.37 (b, 1H), 8.10 (s, 1H) 7.84 (m, 2H), 7.74 (m, 2H), 7.59 (s, 1H), 7.35-7.21 (m, 6H), 6.72 (s, 1H), 6.19 (t, 1H), 5.85 (b, 2H), 3.61-3.54 (m, 4H), 3.19 (m, 1H), 2.03 (m, 2H), 1.46 (m, 2H), 1.09 (d, 6H), 0.92 (t, 3H); $^{13}$C NMR (CDCl$_3$, 75 MHz) δ 167.3, 146.8, 141.5, 141.4, 137.6, 134.5, 132.6, 131.8, 131.3, 129.9, 128.6, 128.4, 128.0, 127.6, 127.1, 126.9, 126.1, 124.3, 116.8, 112.3, 52.1, 40.1, 33.6, 31.0, 26.7, 22.3, 21.4, 11.0.

TM-1257—2,3,4-Trihydroxy-N-(4-hydroxy-naphthalen-2-yl)-5-isopropyl-benzenesulfonamide $^1$H NMR (CDCl$_3$, 300 MHz) δ 8.69 (s, 1H), 8.16 (d, 1H), 7.45-7.37 (m, 3H), 7.09 (m, 1H), 6.81 (s, 2H), 6.26 (s, 1H), 6.12 (s, 1H), 5.69 (s, 1H), 2.97 (m, 1H), 0.92 (d, 6H).

TM-1258—6-[Methyl-(2,3,4-trihydroxy-5-isopropyl-benzenesulfonyl)-amino]-naphthalene-2-carboxylic acid methyl-phenethyl-amide $^1$H NMR (CDCl$_3$, 300 MHz) δ 8.34 (s, 1H), 7.76-7.69 (m, 1.4H), 7.62 (d, 1H), 7.48 (d, 1H), 7.40-7.27 (m, 4H), 7.22 (m, 2H), 7.13 (d, 0.6H), 6.92 (s, 1H), 6.72 (s, 1H), 6.51 (s, 1H), 6.44 (s, 1H), 3.80 (t, 1H), 3.51 (t, 1H), 3.21 (s, 3H), 3.19 (s, 1.4H), 3.09 (m, 1H), 3.04 (m, 1H), 2.88-2.81 (m, 2.6H), 0.95 (d, 6H); $^{13}$C NMR (CDCl$_3$, 75 MHz) δ 172.1, 147.3, 141.8, 139.6, 138.6, 137.5, 134.0, 133.8, 133.2, 133.0, 131.4, 129.1, 128.8, 128.6, 128.5, 128.0, 127.5, 126.7, 126.5, 126.3, 125.8, 124.7, 124.4, 116.9, 110.1, 52.8, 49.5, 38.3, 37.9, 34.3, 33.2, 33.0, 26.4, 22.1, 22.0.

TM-1259—6-[Methyl-(2,3,4-trihydroxy-5-isopropyl-benzenesulfonyl)-amino]-naphthalene-2-carboxylic acid benzyl-phenethyl-amide $^1$H NMR (CDCl$_3$, 300 MHz) δ 8.37 (d, 1H), 7.82 (s, 0.5H), 7.69 (d, 2H), 7.50-7.20 (m, 11.5H), 7.10 (s, 1H), 6.85 (s, 1H), 6.54 (s, 1H), 6.14 (s, 1H), 6.09 (s, 1H), 4.89 (s, 1H), 4.33 (s, 1H), 3.73 (m, 1H), 3.42 (m, 1H), 3.23 (s, 3H), 3.11-3.02 (m, 2H), 2.76 (m, 1H), 0.96 (d, 6H); $^{13}$C NMR (CDCl$_3$, 75 MHz) δ 172.1, 147.0, 141.6, 139.6, 138.9, 137.6, 137.0, 136.4, 134.2, 133.2, 131.5, 131.3, 129.2, 128.8, 128.6, 128.2, 127.7, 126.8, 126.6, 126.5, 126.1, 125.8, 124.9, 124.6, 124.5, 117.0, 110.2, 53.4, 49.6, 47.5, 46.8, 38.0, 34.4, 33.4, 26.5, 22.1.

TM-1260—6-[Methyl-(2,3,4-trihydroxy-5-isopropyl-benzenesulfonyl)-amino]-naphthalene-2-carboxylic acid isobutyl-amide $^1$H NMR (CDCl$_3$, 300 MHz) δ 8.35 (s, 1H), 8.22 (s, 1H), 7.78 (m, 3H), 7.54 (d, 1H), 7.33 (dd, 1H), 6.44 (t, 1H), 6.11 (s, 1H), 5.95 (s, 1H), 3.33 (t, 2H), 3.26 (s, 3H), 3.13 (m, 1H), 1.95 (m, 1H), 1.01 (d, 6H), 1.00 (d, 6H); $^{13}$C NMR (CDCl$_3$, 75 MHz) δ 167.5, 147.0, 141.5, 140.2, 134.4, 132.7, 131.5, 131.3, 129.8, 128.4, 127.9, 126.9, 125.9, 124.8, 124.3, 117.0, 110.3, 47.5, 38.0, 28.6, 26.6, 22.2, 20.2.

TM-1261—6-[Propyl-(2,3,4-trihydroxy-5-isopropyl-benzenesulfonyl)-amino]-naphthalene-2-carboxylic acid methyl-phenethyl-amide $^1$H NMR (CDCl$_3$, 300 MHz) δ 8.41 (s, 1H), 7.76 (m, 1H), 7.66 (m, 1H), 7.56 (s, 1H), 7.32-7.20 (m, 7H), 6.94 (s, 1H), 6.71 (s, 1H), 6.13 (s, 1H), 6.04 (s, 1H), 3.83 (m, 1H), 3.57 (m, 3H), 3.16 (m, 3H), 3.04 (m, 1H), 2.89 (m, 2H), 1.44 (m, 2H), 1.08 (d, 6H), 0.91 (t, 3H); $^{13}$C NMR (CDCl$_3$, 75 MHz) δ 146.7, 141.4, 131.3, 129.4, 128.9, 128.7, 127.8, 127.7, 126.9, 116.7, 112.3, 52.1, 26.6, 22.3, 21.4, 11.0; $^1$H NMR (CO(CD$_3$)$_2$, 300 MHz) δ 8.45 (s, 1H), 8.30 (s, 1H), 8.26 (s, 1H), 7.91 (m, 2H), 7.74 (s, 1H), 7.51 (s, 1H), 7.35-7.23 (m, 5H), 7.04 (s, 1H), 6.68 (s, 1H), 3.79 (m, 1H), 3.70 (m, 2H), 3.57 (m, 1H), 3.20 (m, 2H), 2.99 (m, 4H), 1.45 (m, 2H), 1.06 (d, 6H), 0.91 (t, 3H).

TM-1262—N-Butyl-2,3,4-trihydroxy-5-isopropyl-N-naphthalen-2-yl-benzene-sulfonamide $^1$H NMR (CDCl$_3$, 300 MHz) δ 8.47 (s, 1H), 7.83-7.74 (m, 3H), 7.57 (s, 1H), 7.50 (m, 2H), 7.16 (dd, 1H), 6.76 (s, 1H), 5.91 (b, 1H), 5.53 (b, 1H), 3.61 (t, 2H), 3.19 (m, 1H), 1.38-1.32 (m, 4H), 1.10 (d, 6H), 0.85 (t, 3H); $^{13}$C NMR (CDCl$_3$, 75 MHz) δ 146.4, 141.1, 135.9, 133.2, 132.7, 131.1, 129.0, 128.0, 127.9, 127.7, 126.8, 126.6, 126.2, 116.9, 112.5, 50.2, 30.0, 26.7, 22.3, 19.6, 13.5.

TM-1263—6-[Propyl-(2,3,4-trihydroxy-5-isopropyl-benzenesulfonyl)-amino]-naphthalene-2-carboxylic acid phenethyl-propyl-amide $^1$H NMR (CDCl$_3$, 300 MHz) δ 8.46 (s, 1H), 7.77-7.69 (m, 3H), 7.57 (s, 1H), 7.46-7.43 (m, 1H), 7.34 (m, 2H), 7.22 (m, 4H), 6.91 (s, 1H), 6.72 (s, 1H), 5.91 (s, 1H), 5.55 (d, 1H), 3.77 (m, 1H), 3.58 (m, 3H), 3.20 (m, 1H), 3.18 (m, 1H), 3.16 (m, 2H), 3.03 (m, 1H), 1.75 (m, 1H), 1.48 (m, 3H), 1.09 (d, 7.4H), 0.92 (t, 3H), 0.71 (m, 1.6H); $^{13}$C NMR (CDCl$_3$, 75 MHz) δ 171.7, 146.8, 141.5, 139.0, 137.7, 137.0, 135.0, 133.2, 131.9, 131.4, 129.4, 128.9, 128.6, 128.3, 127.8, 127.7, 127.1, 126.7, 126.5, 125.9, 125.6, 124.7, 124.5, 116.8, 112.3, 52.1, 51.4, 50.5, 46.8, 46.4, 34.9, 33.7, 26.6, 22.3, 21.4, 11.0.

TM-1264—6-[Propyl-(2,3,4-trihydroxy-5-isopropyl-benzenesulfonyl)-amino]-naphthalene-2-carboxylic acid (2-biphenyl-4-yl-ethyl)-amide $^1$H NMR (CDCl$_3$, 300 MHz) δ 8.45 (s, 1H), 8.22 (s, 1H), 7.85 (d, 1H), 7.78 (s, 2H), 7.61-7.57 (m, 5H), 7.45 (t, 2H), 7.35-7.33 (m, 3H), 7.22 (dd, 1H), 6.72 (s, 1H), 6.32 (t, 1H), 5.85 (s, 1H), 5.41 (s, 1H), 3.82 (q, 2H), 3.58 (t, 2H), 3.18 (m, 1H), 3.03 (t, 2H), 1.45 (m, 2H), 1.09 (d, 6H), 0.91 (t, 3H); $^{13}$C NMR (CDCl$_3$, 75 MHz) δ 167.2, 147.5, 146.4, 141.1, 140.7, 139.6, 137.9, 137.7, 134.6, 132.7, 131.9, 131.1, 130.0, 129.3, 128.8, 128.6, 128.0, 127.6, 127.5, 127.3, 127.2, 127.0, 127.0, 124.2, 116.8, 112.3, 52.1, 41.3, 35.3, 26.7, 22.3, 21.4, 11.0.

TM-1265—6-[Propyl-(2,3,4-trihydroxy-5-isopropyl-benzenesulfonyl)-amino]-naphthalene-2-carboxylic acid methyl-(3-phenyl-propyl)-amide $^1$H NMR (CDCl$_3$, 300 MHz) δ 8.44 (d, 1H), 7.82 (s, 1H), 7.76 (m, 2H), 7.59 (s, 1H), 7.46 (t, 1H), 7.30 (m, 2H), 7.20 (dd, 1H), 7.10 (m, 2H), 6.99 (m, 1H), 6.74 (s, 1H), 5.96 (s, 1H), 5.69 (s, 1H), 3.64 (m, 1H), 3.58 (t, 2H), 3.31 (t, 1H), 3.18 (m, 1H), 3.13 (m, 2H), 2.96 (m, 1H), 2.75 (m, 1H), 2.44 (m, 1H), 2.05 (m, 1H), 1.90 (m, 1H), 1.46 (m, 2H), 1.10 (d, 6H), 0.93 (t, 3H); $^{13}$C NMR (CDCl$_3$, 75 MHz) δ 146.7, 141.4, 140.4, 137.0, 134.6, 133.3, 131.9, 131.3, 129.4, 128.4, 128.0, 127.8, 127.0, 126.0, 116.7, 112.3, 52.1, 47.5, 37.6, 28.5, 26.6, 22.3, 21.3, 11.0.

TM-1266—6-(2,3,4-Trihydroxy-5-isopropyl-benzenesulfonylamino)-naphthalene-2-carboxylic acid phenethyl-propyl-amide $^1$H NMR (CDCl$_3$, 300 MHz) δ 8.45 (b, 1H), 7.55 (s, 1H), 7.33-7.18 (m, 9H), 7.01 (m, 1H), 6.96 (s, 1H), 6.85 (m, 1H), 6.60 (b, 1H), 6.11 (b, 1H), 3.78 (m, 1H), 3.60 (m, 1H), 3.48 (m, 1H), 3.05 (m, 3H), 2.77 (m, 1H), 1.79 (m, 1H), 1.49 (m, 1H), 0.98 (d, 6H), 0.68 (m, 3H); $^{13}$C NMR (CDCl$_3$, 75 MHz) δ 173.1, 147.6, 141.3, 138.8, 137.5, 135.6, 133.7, 132.5, 129.9, 128.8, 126.8, 124.2, 122.1, 117.8, 114.3, 51.8, 47.2, 34.8, 33.8, 26.7, 22.3, 20.8.

TM-1267—6-(2,3,4-Trihydroxy-5-isopropyl-benzenesulfonylamino)-naphthalene-2-carboxylic acid benzyl-phenethyl-amide $^1$H NMR (CDCl$_3$, 300 MHz) δ 8.43 (s, 1H), 7.72 (s, 1H), 7.62 (s, 1H), 7.39-6.94 (m, 16H), 6.80 (s, 1H), 6.45 (s, 1H), 6.10 (s, 1H), 4.88 (m, 1H), 4.30 (m, 1H), 3.73 (m, 1H), 3.41 (m, 1H), 3.00 (m, 2H), 2.74 (m, 1H), 0.95 (d, 6H); $^{13}$C NMR (CDCl$_3$, 75 MHz) δ 173.0, 147.4, 141.3, 138.5, 137.3, 136.3, 135.7, 135.5, 133.7, 133.5, 131.7, 131.4, 129.7, 129.4, 128.9, 128.6, 128.1, 127.8, 127.5, 126.9, 126.5, 126.2, 125.7, 124.0, 121.9, 117.6, 113.9, 53.7, 49.9, 47.9, 47.0, 34.3, 33.2, 26.5, 22.1.

TM-1269—2-(2,3,4-Trihydroxy-5-isopropyl-benzoyl)-1,2,3,4-tetrahydro-isoquinoline-7-sulfonic acid phenethyl-amide $^1$H NMR (CDCl$_3$, 300 MHz) δ 10.2 (b, 1H), 7.63 (dd, 1H), 7.52 (s, 1H), 7.31-7.19 (m, 4H), 7.07 (m, 2H), 6.78 (s, 1H), 5.90 (b, 2H), 4.86 (s, 2H), 4.56 (t, 1H), 3.92 (t, 2H), 3.25 (m, 1H), 3.22 (m, 2H), 3.06 (t, 2H), 2.78 (t, 2H), 1.24 (d, 6H); $^{13}$C NMR (CDCl$_3$, 75 MHz) δ 172.2, 145.5, 145.1, 139.6, 138.2, 137.7, 134.2, 131.9, 129.7, 128.8, 128.7, 126.8, 126.4, 125.5, 125.2, 116.8, 109.1, 47.8, 44.3, 35.9, 31.7, 29.1, 26.8, 22.7.

TM-1271—Acetic acid 2,3-diacetoxy-6-(3,4-dihydro-1H-isoquinoline-2-sulfonyl)-4-{7-[2-(4-nitro-phenyl)-ethylsulfamoyl]-3,4-dihydro-1H-isoquinoline-2-carbonyl}-phenyl ester $^1$H NMR (CDCl$_3$, 300 MHz) δ 8.08 (t, 2H), 7.87 (s, 0.5H), 7.78 (s, 0.5H), 7.69-7.62 (m, 1.5H), 7.54 (s, 0.5H), 7.31-7.24 (m, 4H), 7.20-7.14 (m, 3H), 7.12 (m, 1H), 7.04 (m, 1H), 4.93-4.85 (m, 2H), 4.63 (s, 1H), 4.38 (m, 2H), 3.68 (m, 2H), 3.51 (m, 2H), 3.25 (m, 2H), 3.00 (m, 2H), 2.92 (m, 4H), 2.40 (s, 3H), 2.30, 2.38 (s, 3H), 2.23, 2.09 (s, 3H).

TM-1276—2-[2,3,4-Trihydroxy-5-(3-phenyl-propylsulfamoyl)-benzoyl]-1,2,3,4-tetrahydro-isoquinoline-7-sulfonic acid [2-(4-nitro-phenyl)-ethyl]-amide $^1$H NMR (CO(CD$_3$)$_2$, 300 MHz) δ 9.00 (b, 3OH), 8.08 (m, 2H), 7.61 (m, 2H), 7.38 (m, 4H), 7.12 (m, 4H), 6.61 (m, 1H), 4.90 (s, 2H), 4.38 (s, 2H), 3.86 (m, 2H), 3.52 (m, 2H), 3.26 (m, 2H), 3.03 (m, 2H), 2.94 (m, 4H); $^{13}$C NMR (CO(CD$_3$)$_2$, 75 MHz) δ 169.1, 150.5, 147.8, 147.3, 146.9, 140.3, 139.6, 135.0, 134.5, 134.0, 132.6, 130.8, 130.4, 129.5, 127.4, 127.1, 127.0, 125.8, 125.7, 124.0, 121.3, 114.0, 113.9, 60.5, 48.0, 44.5, 44.0, 36.2.

TM-1277—Acetic acid 2,3-diacetoxy-6-{7-[2-(4-nitro-phenyl)-ethylsulfamoyl]-3,4-dihydro-1H-isoquinoline-2-carbonyl}-4-(3-phenyl-propylsulfamoyl)-phenyl ester $^1$H NMR (CDCl$_3$, 300 MHz) δ 8.08 (m, 2H), 7.87 (s, 0.6H), 7.79 (s, 0.5H), 7.69-7.62 (m, 1.8H), 7.54 (s, 0.5H), 7.31-7.24 (m, 3H), 7.20-7.09 (m, 3.4H), 7.05-7.01 (m, 1.2H), 4.93-4.74 (m, 3H), 4.63 (s, 1H), 4.38 (s, 2H), 3.68 (m, 2H), 3.51 (m, 2H), 3.25 (m, 2H), 3.00-2.87 (m, 4H), 2.40 (s, 3H), 2.30 (s, 1.5H), 2.28 (s, 1.5H), 2.23 (s, 2H), 2.09 (s, 1H).

TM-1278—2,3,4-Trihydroxy-5-[methyl-(3-phenyl-propyl)-sulfamoyl]-benzoic acid methyl ester $^1$H NMR (CDCl$_3$, 300 MHz) δ 11.44 (b, 1H), 7.86 (s, 1H), 7.23-7.21 (m, 2H), 7.16 (m, 1H), 7.07 (d, 2H), 4.12 (s, 3H), 2.94 (t, 2H), 2.60 (t, 2H), 1.79 (m, 2H).

TM-1282—2-(5-Benzylsulfamoyl-2,3,4-trihydroxy-benzoyl)-1,2,3,4-tetrahydro-isoquinoline-7-sulfonic acid phenethyl-amide $^1$H NMR (CO(CD$_3$)$_2$, 300 MHz) δ 10.29 (b, 1H), 9.16 (s, 1H), 8.39 (s, 1H), 7.65 (m, 2H), 7.41 (m, 2H), 7.31 (m, 3H), 7.21-7.13 (m, 7H), 6.91 (t, 1H), 6.48 (t, 1H), 4.89 (s, 2H), 4.18 (d, 2H), 3.88 (t, 2H), 3.15 (q, 2H), 3.07 (t, 2H), 2.77 (t, 2H); $^{13}$C NMR (CO(CD$_3$)$_2$, 75 MHz) δ 169.8, 151.0, 146.6, 140.4, 139.9, 139.6, 138.3, 135.3, 134.4, 130.4, 129.6, 129.2, 129.1, 128.6, 128.1, 127.1, 126.0, 125.8, 120.7, 117.9, 112.8, 47.7, 45.4, 45.3.

Example 2

Fluorescence Polarization Binding Assay

In Vitro Bcl-2 Binding Assay

A 21-residue Bid BH3 peptide (QEDIIRNIAR-HLAQVGDSMDR) (SEQ ID NO:1) labeled at the N-terminus with 6-carboxyfluorescein succinimidyl ester (FAM) was used as the fluorescent tag (Flu-Bid-21). It was shown that this fluorescent peptide has high binding affinity with a K$_d$ of 15.74 nM. Bcl-2 used in this assay is a recombinant His-fused soluble protein.

A 5 μl sample of the test compound dissolved in DMSO and preincubated Bcl-2 protein (0.120 μM) with Flu-Bid-21 peptide (0.010 μM) in assay buffer (100 mM potassium phosphate, pH 7.5; 100 μg/ml bovine gamma globulin; 0.02% sodium azide, purchased from Invitrogen Corporation, Life Technologies), are added in Dynex 96-well, black, round-bottom plates (Fisher Scientific) to produce a final volume of 125 μl. For each assay the bound peptide control containing Bcl-2 and Flu-Bid-21 peptide (equivalent to 0% inhibition), and free peptide control containing only free Flu-Bid-21 (equivalent to 100% inhibition), are included on each assay plate. The polarization values in milipolarization units (mP) are measured at excitation wavelength at 485 nm and an emission wavelength at 530 nm, after 4 hours incubation when the binding reached equilibrium, using the Ultra plate reader (Tecan U.S. Inc., Research Triangle Park, N.C.). IC$_{50}$, the inhibitor concentration at which 50% of bound peptide is displaced, is determined from the plot using nonlinear least-squares analysis and curve fitting using GraphPad Prism® software. The unlabeled Bid peptide is used as the positive control. The K$_i$ values were calculated using our developed equation for FP assay (Nikolovska-Coleska et al., *Anal. Biochem.*, 2004, in press). The program for calculating a K$_i$ value is available free of charge via the Internet at http://sw16.im.med.umich.edu/software/calc_ki/.

In Vitro Bcl-XL Binding Assay

For determination of the binding affinity to Bcl-XL protein a human Bcl-xL recombinant His-tagged protein without the C-terminus hydrophobic tail and the Bak-16mer BH3 peptide labeled with 6-carboxyfluorescein succinimidyl ester (FAM) were used. This peptide has shown binding affinity of K$_d$=9.79 nM. The competitive binding assay was performed in the same way as for Bcl-2 protein using a preincubated complex with 60 nM Bcl-xL and 5 nM Flu-Bak peptide in assay buffer containing 50 mM Tris-Bis, pH 7.4; 0.01% bovine gamma globulin.

The compounds described in Example 1 were tested for their binding affinity to Bcl-2 using the fluorescence polarization assay. The following compounds had 1.0 μM or lower IC$_{50}$ values for Bcl-2: TM-1216, 197, 1213, 1203, 1207, 1208, 1209, 1210, 1211, 1205, 1206, 190, 192, 121, and 122, and TW-37, 38, 45, 46, 47, 60, 61, 159, 164, 165, 166, 169, and 172. The following compounds had higher than 1.0 μM IC$_{50}$ values for Bcl-2: TM-174, 175, 176, 178, 1214, 1215, 194, 195, 196, 198, 193, 1212, 199, 1200, 1202, 1217, 1201, 105, 106, 107, 108, 129, and 142 and TW-1, 2, 3, 4, 5, 6, 7, 8, 9, 10, 11, 12, 13, 14, 24, 25, 27, 28, 21, 16, 17, 20, 22, 23, 34, 35, 39, 41, 42, 55, 52, 53, 56, 160, 161, 162, 163, 167, 170, 173, and 174. The following compounds had 1.0 μM or lower IC$_{50}$ values for Bcl-xL: TM-171. The following compounds had higher than 1.0 μM IC$_{50}$ values for Bcl-xL: TM-174, 175, 176, 178, 1214, 1215, 194, 1216, 195, 198, 193, 190, 192, 1201, 105, 106, 107, 129, 142, 159, 1210, 199, 1200, 1202, 1217, 1205, 1206, 162, 163, 133, 165, 167, 168, 169, 183, 180, 196, 197, 1213, 1203, 108, 121, 122, 140, 141, 157, 1207, 1208, 1209, 1211, 1212, and 179.

Example 3

Confirmation of TW-37 Binding to Bcl-2 by NMR

The binding of TW-37 to Bcl-2 was determined using $^{15}$N Heteronuclear Single Quantum Coherence Spectroscopy (HSQC) NMR methods.

The protein samples for NMR studies were uniformly labeled with $^{15}$N for screening and uniformly double labeled with $^{15}$N and $^{13}$C for structure characterization according to the methods described in M. Jansson et al., *J. Biomol. NMR*, 7:131-141 (1996), and M. L. Cai et al., *J. Biomol. NMR*, 11:97-102 (1998).

Since the NMR experiments were performed at pH 7.2 in a pulse field gradient (PFG), HSQC with water flip back was used to maximize signal intensity (S. Grzesiek and A. Bax, *J. Am. Chem. Soc.*, 115:12593-12594 (1993); and G. S. Sheppard et al., Abstracts of Papers of the Amer. Chem. Soc., 213:81 (1997)) and to minimize destruction from the water signal. HSQC spectra of Bcl-2 were recorded prior to (free Bcl-2) and after the addition of the concentrated inhibitor solution. The two spectra were compared to identify the chemical shifts induced by the additions of the inhibitor. Data processing was conducted using nmrPipe, pipp and nmrDraw software (See, D. S. Garrett et al., *J. Magn. Reson. Ser., B* 95:214-220 (1991); and F. Delaglio et al., *J. Biomol. NMR*, 6:277-293 (1995)). Shifted peaks were cross-referenced to the assignment table to reveal the residues affected by the presence of gossypol compounds. The residues affected by the binding of TW-37 are shown in FIG. 1, which shows that TW-37 binds to the BH3 binding site in Bcl-2.

Example 4

Inhibition of Cell Growth by TW-37 in Human Cancer Cells

To test the effect of compounds of the present invention on inhibition of cell growth in human cancer cells, TW-37 was administered to five different cancer cell lines. LnCap, PC-3, and DU145c prostate cancer cell lines and 2LMP and MCF-10A breast cancer cell line were each seeded in 96-well plates with increasing concentrations of TW-37. The cells were then incubated at 37° C. with 5% $CO_2$ for 5 days, followed by detection of cell viability with MTT. Untreated cells were used as 100% growth. TW-37 inhibited the cell growth of each of the cell lines, with an $IC_{50}$ in the range of about 1-5 μM (FIG. 2). These data indicate that TW-37 is capable of inhibiting cell growth in human cancer cells.

Additional compounds of the present invention were tested for their effect on cell growth of PC-3 cells. PC-3 cells were grown as above and increasing concentrations of compounds were added. Cell viability was then assayed using WST (FIG. 3). The results show that all of the tested compounds had the ability to inhibit the growth of prostate cancer cells, with most compounds having an $IC_{50}$ in the range of about 0.5-10 μM.

Compounds of the present invention were also tested for their effect on cell growth of MDA-MB-231 (2LMP) cells. Cells were grown as above and increasing concentrations of compounds were added. Cell viability was then assayed using WST. The results show that all of the tested compounds had the ability to inhibit the growth of prostate cancer cells, with most compounds having an $IC_{50}$ in the range of about 0.1-20 μM. Those compounds within this range are: TM-103, 104, 105, 106, 107, 108, 109, 110, 111, 121, 122, 125, 126, 127, 128, 129, 130, 132, 133, 134, 135, 136, 137, 140, 141, 142, 144, 145, 146, 147, 148, 149, 150, 152, 153, 154, 155, 156, 165, 166, 167, 168, 169, 170, and 171. Those compounds above 20 μM are: TM-124 and 143.

Example 5

TW-37 Induces Apoptosis in Prostate Cancer PC-3 Cells

PC-3 cells in 6-well plates were treated with TW-37 for 45 hours and apoptosis was analyzed by Annexin V-FITC staining and flow cytometry. The results show that increasing concentrations of TW-37 induced increasing levels of apoptosis in PC-3 cells, with 2.5 μM TW-37 resulting in about 35% apoptotic cells (FIG. 4). These results show that TW-37 is capable of inducing apoptosis in cancer cells.

Example 6

TW-37 Activates Caspase-3 in Prostate Cancer PC-3 Cells

To test if the induction of apoptosis in prostate cancer cells is mediated by the caspase pathway, PC-3 cells and PrEC (human normal prostate epithelial cells) were treated with TW-37 for 48 hours, then stained with CaspGlow Red Active Capsase-3 Staining Kit (BioVision, Inc.), in which rhodamine-DEVD-FMK (SEQ ID NO:1) binds covalently to active caspase-3 in apoptotic cells. The specific caspase-3 inhibitor Z-DEVD-FMK (1 μg/ml) was added in parallel tubes to inhibit caspase-3 activation. The cells were analyzed by flow cytometry in the red channel and the results are shown as percent of cells having active caspase-3 (FIG. 5). The results show that treatment of PC-3 cells with TW-37 results in the activation of caspase-3 within the cells, with 5 μM TW-37 resulting in about 60% of the cells having activated caspase-3 (FIG. 5). Addition of the caspase inhibitor Z-DEVD-FMK blocked the activation of caspase-3. TW-37 had no effect on normal prostate epithelial cells. These results show that the apoptosis induced by caspase-3 in human cancer cells is mediated by the caspase pathway, and that the effect is specific for cancer cells.

Example 7

TW-37 Enhances Cisplatin-Induced Apoptosis in Breast Cancer MDA-231 Cells

The ability of compounds having formula I to increase apoptosis of cancer cells induced by chemotherapeutic drugs was tested using a combination of TW-37 and cisplatin (CDDP). CDDP is a DNA damaging agent and can effectively induce apoptosis in MDA-231 breasted cancer cells and is also a clinically used chemotherapeutic drug for cancer.

MDA-231 cells were treated with CDDP and TW-37 alone or in combination for 42 hours and cell survival was analyzed. Exposure to CDDP resulted in decreased cell survival with an $IC_{50}$ of around 0.75 μM (FIG. 6). The addition of 0.2 μM or 0.3 μM TW-37 enhanced the CDDP induced cell death, with 0.3 μM TW-37 lowering the $IC_{50}$ of CDDP by about half (FIG. 6). The results show that TW-37 is effective to potentiate the activity of CDDP in inducing cell death in MDA-231 cells.

Example 8

Inhibition by TW-37 of Tumor Growth in Xenograft Model or Prostate Cancer in Nude Mice To test the ability of TW-37 to control tumor growth in vivo a nude mouse xenograft model was used. The maximal tolerated dose (MTD) of TW-37 was determined using 4-6 week old female Balb/c mice with i.v. q.d.×5 for three weeks. The MTD of TW-37 was determined to be 80 mg/kg under this schedule. TAXOTERE (TXT) and cisplatin (CDDP) were used as positive controls. For the PC-3 tumor model, $5 \times 10^6$ PC-3 cells were injected into the flanks of NCr-nu male nude mice on both sides. The quarter-MTD and half-MTD doses, i.e., 20 and 40 mg/kg, i.v. q.d.×5 for 3 weeks was tested. When tumors grew to approximately 50-60 mm³, mice were randomized to (1) Control group; (2) TW-37 treatment group (20 mg/kg, i.v. q.d.5×3 weeks); (3) TW-37 treatment group (40 mg/kg, i.v. q.d.5×3 weeks); (4) TXT group (7.5 mg/kg i.v. once a week for 3 weeks); (5) CDDP group: (5 mg/kg i.v.). The tumor sizes were measured 2 times a week and calculated as: Tumor Volume=$(A \times B^2)/2$ where A and B are the tumor length and width (in mm), respectively. The results are shown in FIG. 7. The results show that TW-37 is capable of significantly inhibiting tumor growth in vivo, with 40 mg/ml TW-37 being as potent as TAXOTERE.

TAXOTERE and cisplatin both have toxic side effects when used for cancer treatment. To compare the toxic side effects of TW-37 with these known anti-cancer agents, the body weights of the animals used in the above study were monitored to assess bodyweight loss as a sign of toxicity. The results are shown in FIG. 8. The results show that TAXOTERE caused a mild loss in body weight over the 35 days of treatment while cisplatin caused a significant loss of body weight by three weeks of treatment which returned almost to control levels by five weeks. TW-37 had little effect on body weight throughout the experiment, indicating that TW-37 is not likely to have significant cytotoxic side effects during use.

Example 9

TW-37 Enhances Inhibition of Tumor Growth By TAXOTERE in Xenograft Model or Prostate Cancer in Nude Mice The prostate cancer PC-3 xenograft model was used to test the ability of TW-37 to enhance the activity of TAXOTERE in inhibiting tumor growth. When tumors grew to approximately 50-60 mm$^3$, mice were randomized to (1) Control group (6 mice/12 tumors); (2) TW-37 treatment group (40 mg/kg, i.v. q.d.5×3 weeks, 5 mice/10 tumors); (3) TXT group (7.5 mg/kg i.v. once a week for 3 weeks); (4) Combination group: TW-37 plus TXT (5 mice/10 tumors). The tumor sizes were measured 2 times a week and calculated as: Tumor Volume=(A×B$^2$)/2 where A and B are the tumor length and width (in mm), respectively.

The results are shown in FIG. 9. TW-37 at 40 mg/kg significantly inhibited tumor growth as compared to control ($p<0.001$, two-way ANOVA, n=10). Table 8 summarizes the tumor growth inhibition (T/C) and tumor growth delay (T-C) values calculated as described (Corbett, Transplantable syngeneic rodent tumors. Tumor Models in Cancer Research, ed. B. A. Teicher. 2002, Totowa: Humana Press. Pp. 41-71) (numbers in parenthesis are doses mg/kg body weight). The T/C value is 34.5% for 40 mg/kg TW-37, 55.1% for 7.5 mg/kg TXT and 32.1% for 11 mg/kg TXT. Thus, under the NCI criteria, 40 mg/kg TW-37 and 11 mg/kg TXT are significantly active in this model (T/C<42%), whereas 7.5 mg/kg TXT is not (T/C>42%). 11 mg/kg is near the MTD dose and 7.5 mg/kg is a sub-optimal dose for TXT in this animal model. More significantly, a combination of TW-37 with a sub-optimal dose of TXT (7.5 mg/kg) resulted in T/C=19.6%. Additionally, the combination treatment resulted in complete tumor regression in some animals whereas none were seen with the single drug treatments. Thus, the combination therapy is significantly more effective than either treatment alone ($p<0.0001$, two-way ANOVA, n=10).

TABLE 5

|  | TW-37 | TXT (7.5 mg/kg) | TXT (11 mg/kg) | TXT (7.5 mg/kg) + TW-37 |
|---|---|---|---|---|
| T/C (%) | 34.5 | 55.1 | 32.1 | 19.6 |
| T-C (days) | 37 | 30 | 32 | — |
| Complete tumor regression | 0/10 | 0/10 | 0/10 | 2/10 |

To monitor toxicity, animal body weights were measured and plotted in FIG. 10. As can be seen, TW-37 treated mice showed no obvious body weight loss during the treatment. TXT treatment or combination with TW-37 caused reversible body weight loss that was recovered after the treatment stopped. The combination therapy did not cause more severe toxicity than TXT alone ($p<0.05$, two-way ANOVA).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound selected from the group consisting of:

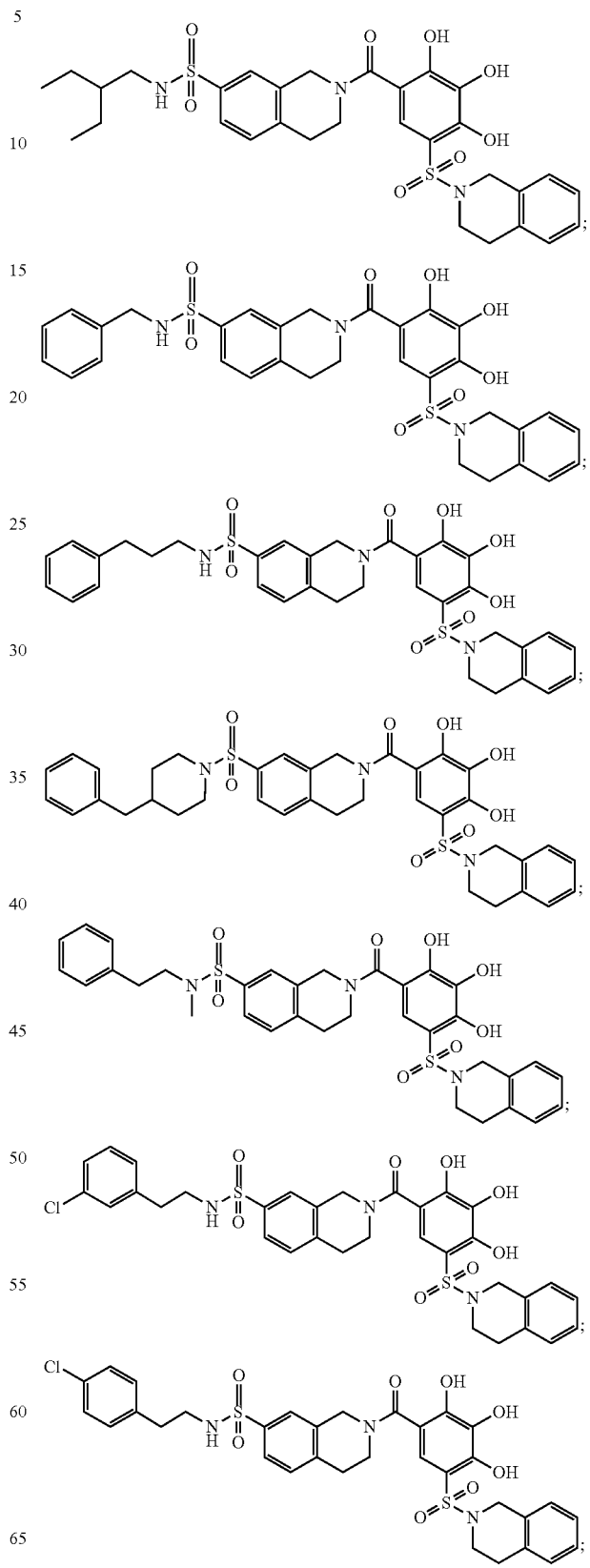

211
-continued
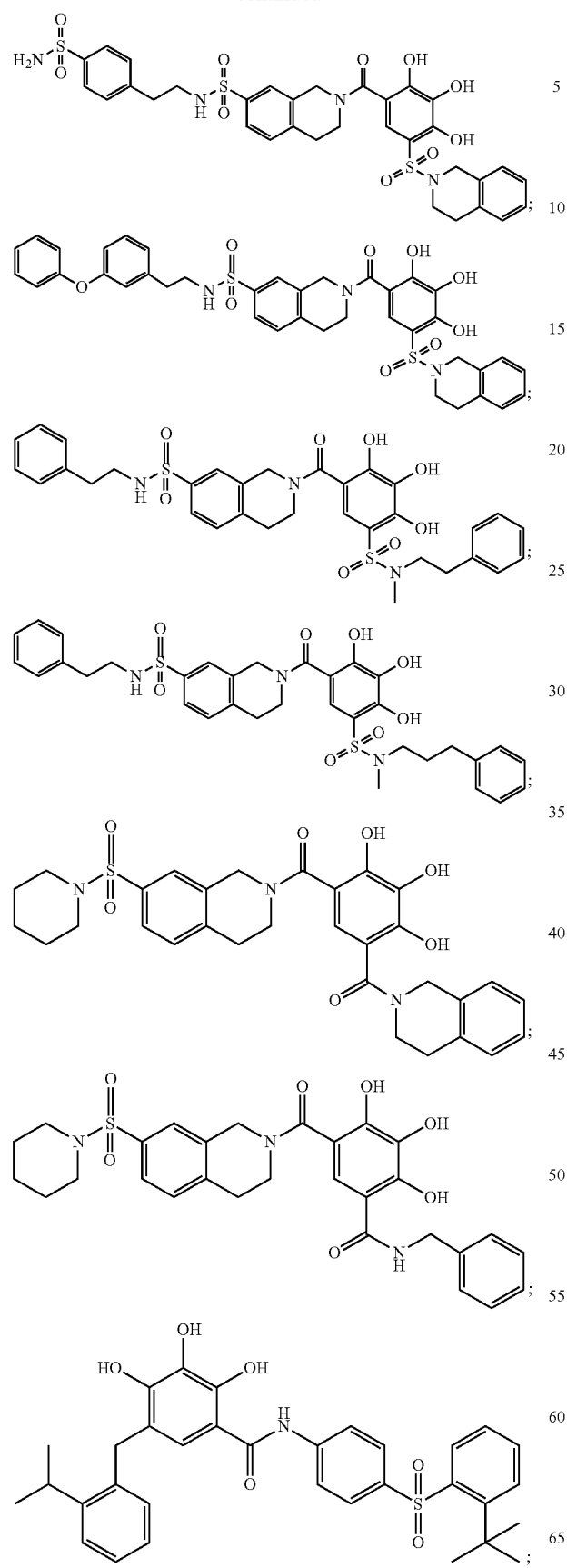
212
-continued
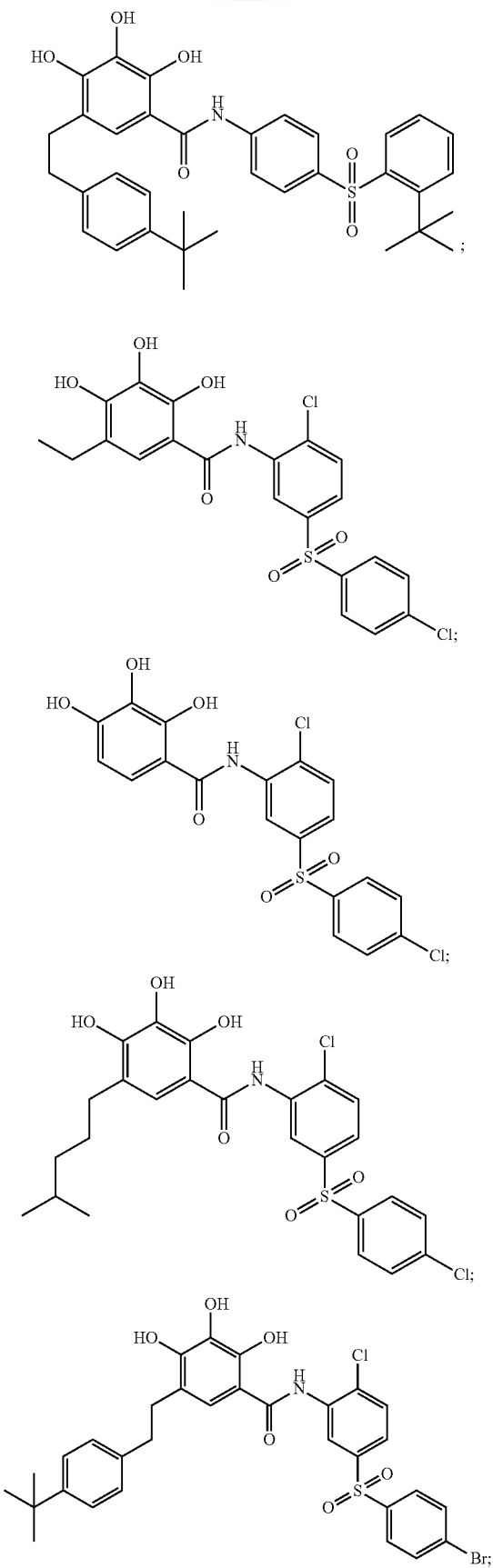

-continued

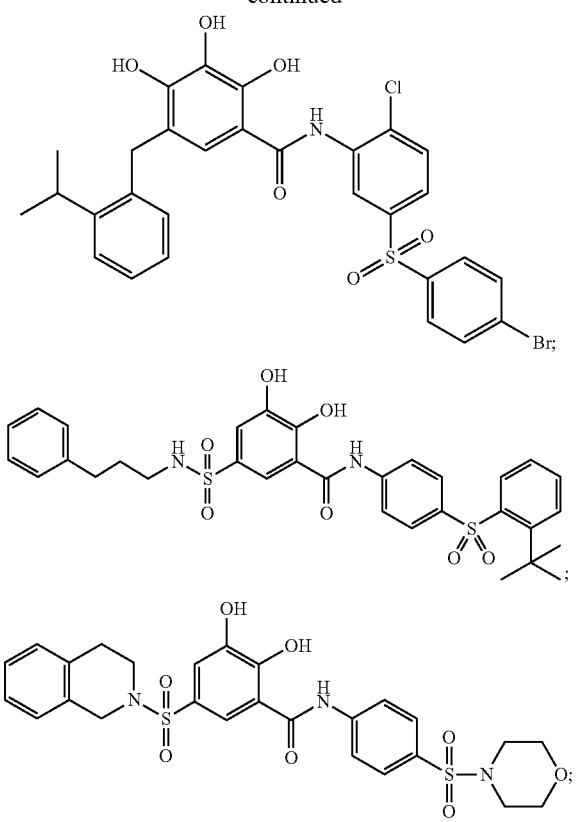

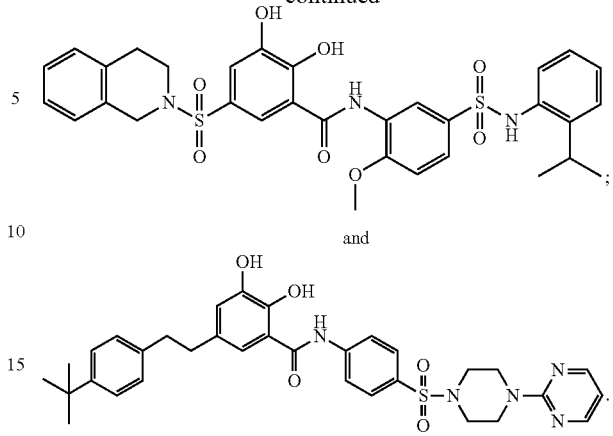

2. A pharmaceutical composition comprising a compound of claim 1 and a pharmaceutically acceptable carrier.

3. A kit comprising a compound of claim 1 and instructions for administering said compound to an animal.

4. The kit of claim 3, further comprising an inducer of apoptosis.

5. The kit of claim 4, wherein said inducer of apoptosis is a chemotherapeutic agent.

6. The kit of claim 3, wherein said instructions are for administering said compound to an animal having a hyperproliferative disease.

7. The kit of claim 6, wherein said hyperproliferative disease is cancer.

* * * * *

UNITED STATES PATENT AND TRADEMARK OFFICE
CERTIFICATE OF CORRECTION

| | | |
|---|---|---|
| PATENT NO. | : 8,557,812 B2 | Page 1 of 1 |
| APPLICATION NO. | : 11/209998 | |
| DATED | : October 15, 2013 | |
| INVENTOR(S) | : Shaomeng Wang et al. | |

It is certified that error appears in the above-identified patent and that said Letters Patent is hereby corrected as shown below:

In the Claim

Claim 1, column 211, lines 35-55, delete

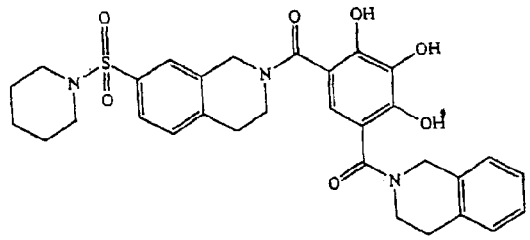 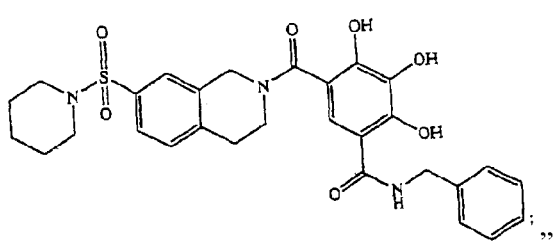

"                                                                                                                ", and insert -- 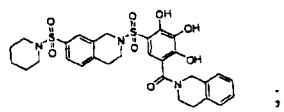 ; 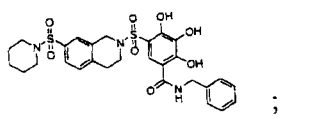 ; --

Signed and Sealed this
Twenty-sixth Day of November, 2013

Margaret A. Focarino
*Commissioner for Patents of the United States Patent and Trademark Office*